(12) United States Patent
Niwa et al.

(10) Patent No.: US 8,273,013 B2
(45) Date of Patent: Sep. 25, 2012

(54) ENDOSCOPE INSERTION ASSISTANT PROBE AND APPLICABLE ENDOSCOPE APPARATUS THEREFOR

(75) Inventors: Hiroshi Niwa, Tokyo (JP); Fumiyuki Onoda, Tokyo (JP)

(73) Assignee: Olympus Corporation, Tokyo (JP)

( * ) Notice: Subject to any disclaimer, the term of this patent is extended or adjusted under 35 U.S.C. 154(b) by 1349 days.

(21) Appl. No.: 11/525,761

(22) Filed: Sep. 22, 2006

(65) Prior Publication Data

US 2007/0015966 A1     Jan. 18, 2007

Related U.S. Application Data

(63) Continuation of application No. PCT/JP2005/006175, filed on Mar. 30, 2005.

(30) Foreign Application Priority Data

Mar. 31, 2004  (JP) ................................. 2004-108360

(51) Int. Cl.
*A61B 1/00* (2006.01)

(52) U.S. Cl. ........ 600/115; 600/114; 600/117; 600/407; 600/424; 600/427

(58) Field of Classification Search .......... 600/114–115, 600/117
See application file for complete search history.

(56) References Cited

U.S. PATENT DOCUMENTS

| 4,862,874 A * | 9/1989 | Kellner .......................... 600/116 |
| 5,103,804 A | 4/1992 | Abele et al. |
| 5,681,260 A * | 10/1997 | Ueda et al. ..................... 600/114 |
| 5,728,044 A * | 3/1998 | Shan .............................. 600/145 |
| 5,957,833 A * | 9/1999 | Shan .............................. 600/117 |
| 6,203,493 B1 * | 3/2001 | Ben-Haim ..................... 600/117 |
| 6,572,535 B2 * | 6/2003 | Watanabe et al. ............. 600/117 |
| 6,689,049 B1 * | 2/2004 | Miyagi et al. ................. 600/117 |
| 6,953,431 B2 * | 10/2005 | Barthel ......................... 600/116 |
| 7,721,742 B2 * | 5/2010 | Kalloo et al. ................. 600/115 |
| 2003/0028096 A1 | 2/2003 | Niwa et al. |
| 2005/0154259 A1 * | 7/2005 | Demarco ...................... 600/114 |

FOREIGN PATENT DOCUMENTS

| DE | 12 48 223 B | 8/1967 |
| JP | 6-217931 | 8/1994 |
| JP | 7-327918 | 12/1995 |
| JP | 2000-262487 | 9/2000 |
| JP | 2001-340462 | 12/2001 |
| JP | 2002-301019 | 10/2002 |
| JP | 2002-345727 | 12/2002 |
| JP | 2003-47586 | 2/2003 |
| JP | 2005-118375 | 5/2005 |

OTHER PUBLICATIONS

Supplementary European Search Report dated Aug. 27, 2009.
English Abstract of Japanese Patent Publication No. 2003-047586, dated Feb. 18, 2003.
English Abstract of Japanese Patent Publication No. 2002-345727, dated Dec. 3, 2002.

* cited by examiner

*Primary Examiner* — Matthew J Kasztejna
(74) *Attorney, Agent, or Firm* — Scully, Scott, Murphy & Presser, P.C.

(57) ABSTRACT

An endoscope insertion assistant probe is inserted into a body cavity prior to insertion of an insertion portion of an endoscope into the body cavity, to assist the insertion of the endoscope, and includes a flexible, elongated probe; and a distal end guiding element that is arranged at a distal end portion of the probe. The distal end guiding element is made of a thin-film resin member and expandable by fluid.

1 Claim, 44 Drawing Sheets

ENDOSCOPE INSERTION ASSISTANT PROBE AND APPLICABLE ENDOSCOPE APPARATUS THEREFOR

CROSS-REFERENCE TO RELATED APPLICATIONS

This application is a continuation of PCT international application Ser. No. PCT/JP2005/006175 filed Mar. 30, 2005 which designates the United States, incorporated herein by reference, and which claims the benefit of priority from Japanese Patent Application No. 2004-108360, filed Mar. 31, 2004, incorporated herein by reference.

BACKGROUND OF THE INVENTION

1. Field of the Invention

The present invention relates to an endoscope insertion assistant probe and an endoscope apparatus to which the endoscope insertion assistant probe can be applied. More specifically, the present invention relates to an endoscope insertion assistant probe which is insertable inside a body cavity prior to an insertion of an insertion portion of an endoscope inside the body cavity for assistance of the insertion of the endoscope, and to an endoscope apparatus to which the endoscope insertion assistant probe can be applied.

2. Description of the Related Art

Conventionally, endoscopes are widely employed in the field of medicine. Since the endoscope has an elongated insertion portion which is insertable into a curved body cavity, an observation of an organ deep inside the body cavity can be carried out without making an incision into a body surface. In addition, when necessary, a treatment instrument can be inserted into a treatment instrument channel provided in the insertion portion of the endoscope, and various procedures and treatments can be carried out with the use of such treatment instrument.

When the conventional endoscope is employed for an observation and examination of an interior of a lower alimentary tract, the insertion portion of the endoscope is inserted from an anus into the curved body cavity, for example. During the examination, an operator of the endoscope cannot obtain information concerning a state of the inserted insertion portion of the endoscope inside the body cavity. For example, the operator cannot know in which portion of the body cavity a distal end portion of the insertion portion of the endoscope is located. Therefore, the operator needs to be highly trained in order to smoothly insert the insertion portion of the endoscope into the body cavity.

To alleviate such inconvenience, various proposals have conventionally been made on a system and a probe that allows for a detection of a shape of an inserted object, for example. The proposed system and the probe allow for detection and display of a shape of the insertion portion of the endoscope or the probe that is inserted into the body cavity. See JP-A No. 2002-345727 (KOKAI) and JP-A No. 2003-47586 (KOKAI), for example.

A conventional probe disclosed in JP-A No. 2002-345727 (KOKAI) allows for a detection of the shape of an inserted object. The probe includes plural coil units that are provided in the insertion portion of the endoscope and each generate or detect a magnetic field, and a signal line that is connected to the coil units. A detecting unit that is arranged outside receives signals sent from the coil units in the insertion portion through the signal line. The shape of the insertion portion at a time of insertion is displayed on a monitor of the detecting unit.

Another conventional probe disclosed in JP-A No. 2003-47586 (KOKAI) also allows for a detection of the shape of the inserted object. The probe is arranged inside a treatment instrument insertion channel that is formed inside the endoscope. The probe includes a magnetic field detecting element, for example. While the probe is arranged in the treatment instrument insertion channel of the endoscope, the insertion portion is inserted into the body cavity. Then, the shape of the insertion portion at the time of insertion is displayed on a monitor of a detecting unit.

SUMMARY OF THE INVENTION

An endoscope insertion assistant probe according to one aspect of the present invention is inserted into a body cavity prior to insertion of an insertion portion of an endoscope into the body cavity, to assist the insertion of the endoscope, and includes a flexible, elongated probe; and a distal end guiding element that is arranged at a distal end portion of the probe. The distal end guiding element is made of a thin-film resin member and expandable by fluid.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of the present invention will be described with reference to the accompanying drawings.

Figure 1:
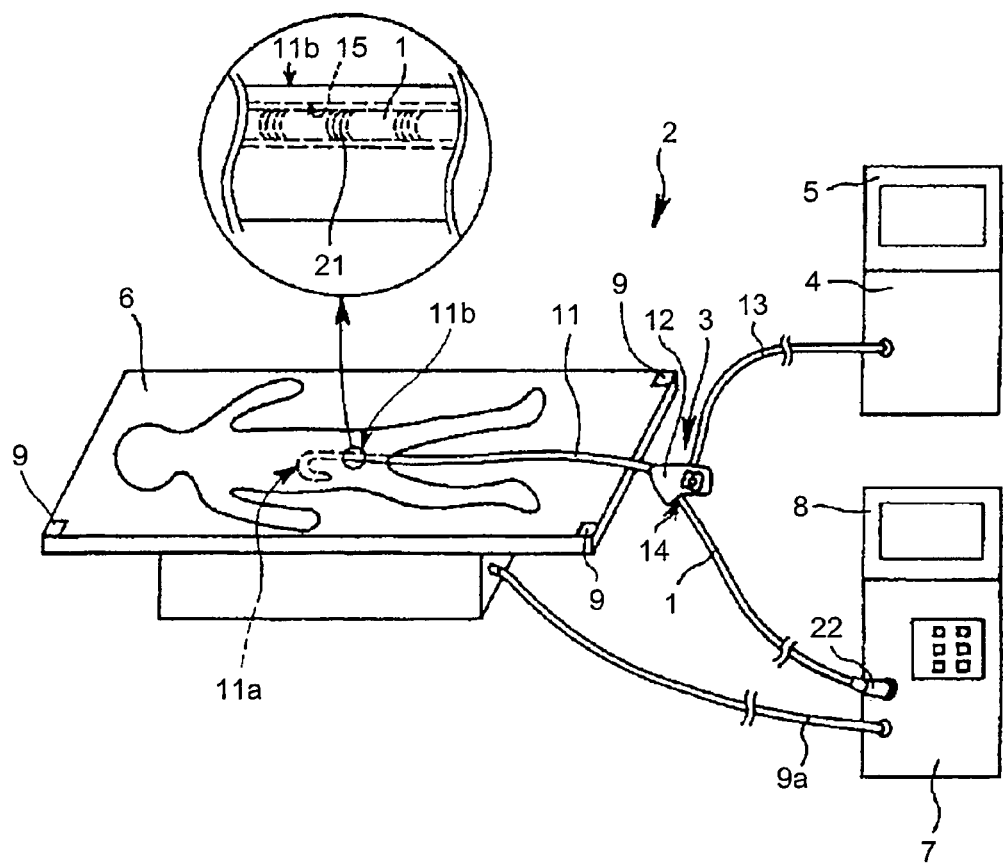
FIG. 1 shows a schematic structure of an inserted shape detecting apparatus system to which an endoscope insertion assistant probe (inserted shape detecting probe) according to a first embodiment of the present invention is applied.
Figure 2:
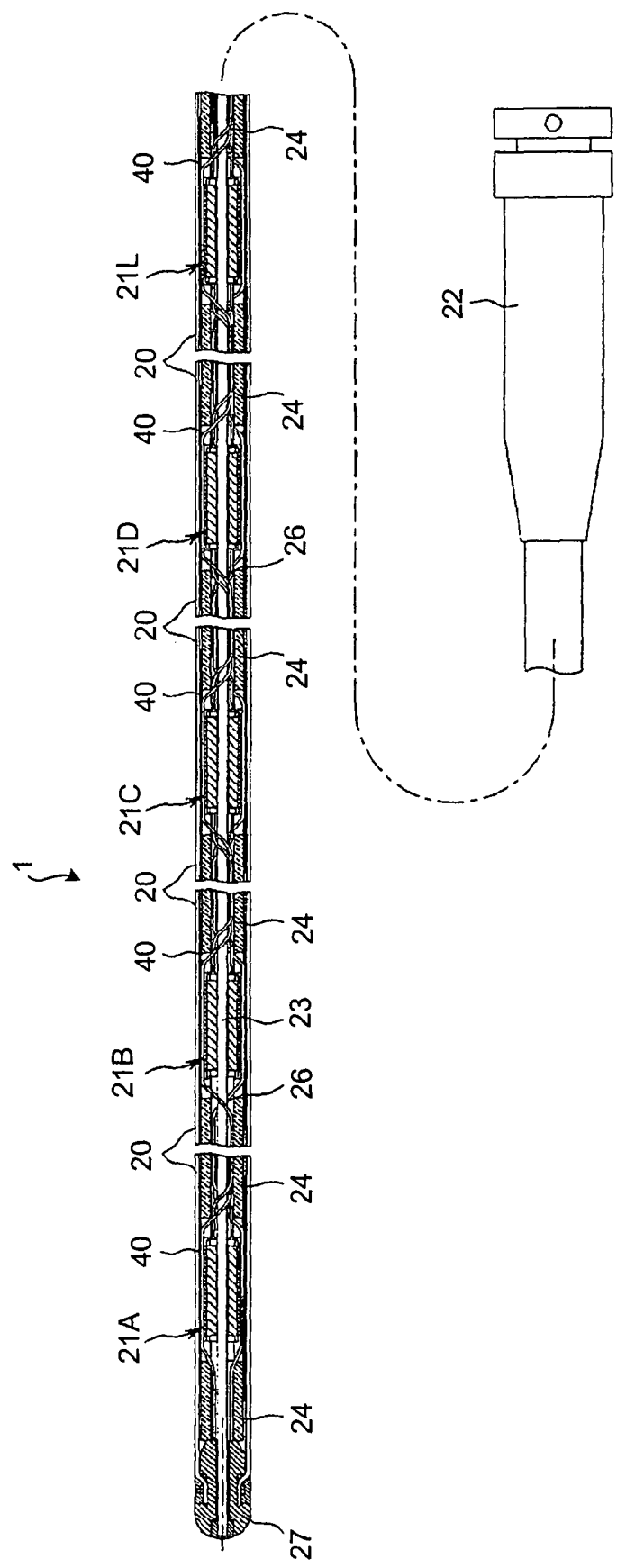
FIG. 2 is a schematic sectional view of an internal structure of the endoscope insertion assistant probe (inserted shape detecting probe) in the inserted shape detecting apparatus system of FIG. 1.

FIG. 1 shows a schematic structure of an endoscope apparatus (inserted shape detecting apparatus system) to which an endoscope insertion assistant probe (inserted shape detecting probe) according to a first embodiment of the present invention is applied. FIG. 2 is a schematic sectional view of an internal structure of the inserted shape detecting probe (endoscope insertion assistant probe) in the inserted shape detecting apparatus system of FIG. 1.

In the embodiments described hereinafter, an inserted shape detecting apparatus system to which the inserted shape detecting probe, which is an endoscope insertion assistant probe, is applied will be described as an example of an endoscope apparatus to which the endoscope insertion assistant probe of the present invention is applied.

Prior to the detailed description of the endoscope insertion assistant probe of the embodiments, a description will be given on the schematic structure of the inserted shape detecting apparatus system to which the endoscope insertion assistant probe is applied with reference to FIG. 1.

An inserted shape detecting apparatus system 2 shown in FIG. 1 includes an inserted shape detecting probe 1 as an embodiment of the endoscope insertion assistant probe. The inserted shape detecting apparatus system 2 primarily includes an endoscope 3 which is inserted from an anus of a subject, for example, into a body cavity or the like of the subject for an observation of an observed region, a video processor 4 which generates a video signal from an imaging signal obtained through imaging by the endoscope 3, a monitor 5 that displays an endoscopic image based on the video signal sent from the video processor 4, an inserted shape detecting bed 6 on which the subject lies and which detects a magnetic field from the inserted shape detecting probe 1, an inserted shape detecting apparatus 7 which drives the inserted shape detecting probe 1 and outputs a video signal, and a monitor 8 that displays a shape of an insertion portion as output from the inserted shape detecting apparatus 7. The video signal output from the inserted shape detecting apparatus 7 is generated from a signal corresponding to the magnetic field detected by the inserted shape detecting bed 6 and represents an image of the inserted shape of the endoscope inside the body cavity.

The endoscope 3 includes an elongated insertion portion 11, an operation portion 12, and an universal cord 13. The insertion portion 11 includes an insertion portion bendable portion 11a which is arranged at a distal end side and is curved at a small curvature radius, and an insertion portion flexible tube portion 11b which is arranged closer to a proximal end side than the insertion portion bendable portion 11a and is curved at a relatively large curvature radius. The insertion portion 11 is inserted into the body cavity. The operation portion 12 is arranged next to the insertion portion 11 at a proximal end side of the insertion portion 11. The operation portion 12 functions also as a gripper. The universal cord 13 extends from a side portion of the operation portion 12 and is connected with an external unit such as the video processor 4.

The inserted shape detecting probe 1 is inserted into a treatment instrument insertion channel 15 from a treatment instrument insertion opening 14 provided in the operation portion 12 of the endoscope 3. The inserted shape detecting probe 1 includes plural source coils 21 which serve as shape detecting elements that generates a magnetic field, for example (see FIG. 2 for details). The inserted shape detecting probe 1 is connected to the inserted shape detecting apparatus 7 via a connector portion 22 which is provided at a proximal end side thereof.

On the other hand, the inserted shape detecting bed 6 includes plural sense coils 9 which serve as magnetic field detecting elements that detect a magnetic field generated by the source coils 21. The inserted shape detecting bed 6 is connected to the inserted shape detecting apparatus 7 via a cable 9a. A detection signal of the sense coil 9 is transmitted to the inserted shape detecting apparatus 7 via the cable 9a.

The inserted shape detecting apparatus 7 is provided, for example, with a source coil driving unit (not shown) that drives the source coils 21, a source coil position analyzer (not shown) that analyzes three-dimensional position coordinates of the source coils 21 based on signals transmitted from the sense coils 9, an inserted shape image generating unit (not shown) that calculates a three-dimensional shape of the insertion portion 11 based on three-dimensional position coordinate information of the source coils 21, converts the three-dimensional shape into a two-dimensional coordinate for monitor display, and generates an image.

Further, the inserted shape detecting apparatus 7 is provided with a fluid supply unit, such as a pump, a driving control circuit for the fluid supply unit, and the like. The fluid supply unit delivers fluid, i.e., gas or liquid inside the inserted shape detecting probe 1 which is connected to the inserted shape detecting apparatus 7 via the connector portion 22.

In the example described as the embodiment, plural shape detecting elements (source coils 9) that generate a magnetic field are arranged in the inserted shape detecting probe 1, whereas plural magnetic field detecting elements (sense coils 9) are arranged in the inserted shape detecting bed 6. The present invention, however, is not limited to the above arrangement. For example, the plural shape detecting elements (sense coils) that detect a magnetic field may be arranged in the inserted shape detecting probe 1, and the plural magnetic field generating elements (source coils) may be arranged in the inserted shape detecting bed 6.

A schematic inner structure of the inserted shape detecting probe 1 will be described below with reference to FIG. 2. As described above, the inserted shape detecting probe 1 in the inserted shape detecting apparatus system shown in FIG. 1 serves as the endoscope insertion assistant probe.

As shown in FIG. 2, the inserted shape detecting probe 1 primarily includes an outer sheath 20 that forms a jacket, plural (twelve in the present embodiment) source coils 21A, 21B, 21C, 21D, . . . , 21L (hereinafter simply referred to as 21A to 21L) that have a hollow structure and a substantially cylindrical shape, a thin elongate core 23 to which the source coils 21A to 21L are adhesively fixed, pipe-like inner sheaths 24 that are arranged in series with respect to the respective source coils 21A to 21L, a heat shrinkable tube 40 that is a coupling and fixing member that covers the source coils 21A to 21L and the inner sheaths 24 that are adjacent to the source coils 21A to 21L to integrally connect the source coils 21A to 21L and the inner sheath 24, and the connector portion 22 that is arranged at a proximal end portion to secure an electric connection between the inserted shape detecting probe 1 and the inserted shape detecting apparatus 7.

Here, the source coils are numbered sequentially from the distal end side of the inserted shape detecting probe 1, i.e., the source coil 21A which is arranged at the distal end side of the inserted shape detecting probe 1 will be referred to as first source coil 21A; the source coil 21B will be referred to as second source coil 21B; 21C as third source coil; 21D as fourth source coil; . . . ; and 21L as twelfth source coil.

The source coils 21A to 21L and the inner sheaths 24 are arranged alternately from the distal end side to the proximal end side of the inserted shape detecting probe 1 as shown in FIG. 2, in an order of the first source coil 21A, the inner sheath 24, the second source coil 21B, the inner sheath 24, the third source coil 21C, and so on. Further, one end portion of each of the source coils 21A to 21L is connected to a signal line 26 that transmits a driving signal sent from the source coil driving unit (not shown) provided in the inserted shape detecting apparatus 7 (see FIG. 1).

Among the source coils 21A to 21L that are fixed to the core 23, the first to the third source coils 21A to 21C are arranged in the bendable portion 11a (see FIG. 1) of the insertion portion. The first to the third source coils 21A to 21C form a group of detecting elements that detect a shape of the bendable portion to obtain shape data of the bendable portion 11a of the insertion portion.

Further, the fourth to the twelfth source coils 21D to 21L are arranged in the flexible tube portion 11b (see FIG. 1) of the insertion portion. The fourth to the twelfth source coils 21D to 21L form a group of detecting elements that detect a shape of the flexible tube portion to obtain shape data of the flexible tube portion 11b of the insertion portion.

The signal lines 26 that are connected to the respective source coils 21A to 21L penetrate through inside the inner sheaths 24 that are arranged at the proximal end sides of the respective source coils 21A to 21L, and extend toward the proximal end side of the inserted shape detecting probe 1. Specifically, the signal line 26 that extends from the first source coil 21A located at the most distal end penetrates inside the outer sheath 20 along circumferences of all the remaining source coils, i.e., from the second source coil 21B adjacent to the first source coil 21A up to the last source coil 21L, and eventually reaches the connector portion 22 at the proximal end side of the inserted shape detecting probe 1. Hence, the number of signal lines 26 that penetrate inside the inner sheath 24 increases from the distal end side to the proximal end side of the inserted shape detecting probe 1.

The signal line 26 that penetrates inside the inner sheath 24 is loosely wound around the core 23 so as to sag by a predetermined amount. Such arrangement prevents bending of the inserted shape detecting probe 1 from applying tension to the signal line 26 and causing damages such as breaking.

A distal end piece 27 is arranged at a most distal end of the outer sheath 20 of the inserted shape detecting probe 1. A distal end side of the distal end piece 27 is formed in a semi-spherical shape.

Figure 3:
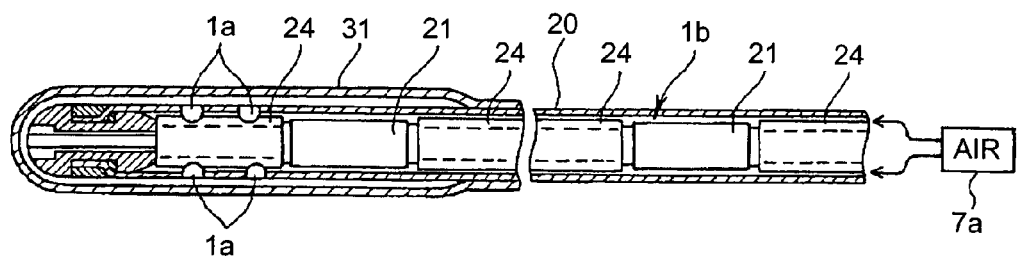
FIG. 3 is an enlarged sectional view of a distal end portion of the endoscope insertion assistant probe (inserted shape detecting probe) of FIG. 2, to which a resin member (balloon) is attached in a contracted state.

Further, a balloon 31 is attached to a portion near the distal end portion of the inserted shape detecting probe 1 having the above-described structure as shown in FIG. 3. The balloon 31 is a flexible, expandable, thin-film-like, resin member that serves as a distal end guiding element. The resin member may be made of a material such as silicone, latex, and polyethylene.

Figure 4:
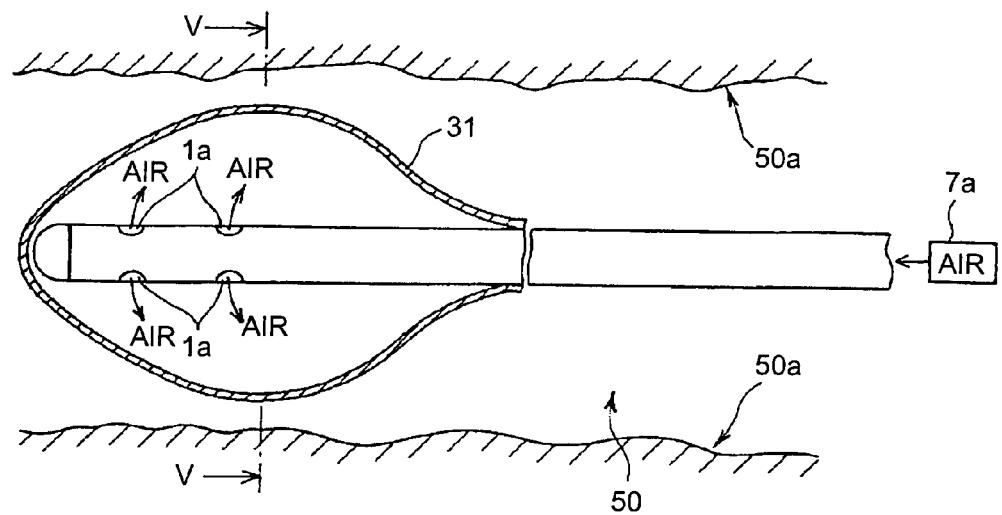
FIG. 4 shows the endoscope insertion assistant probe (inserted shape detecting probe) of FIG. 2, to which the resin member (balloon) is attached in an expanded state, inserted inside an intestinal canal.
Figure 5:
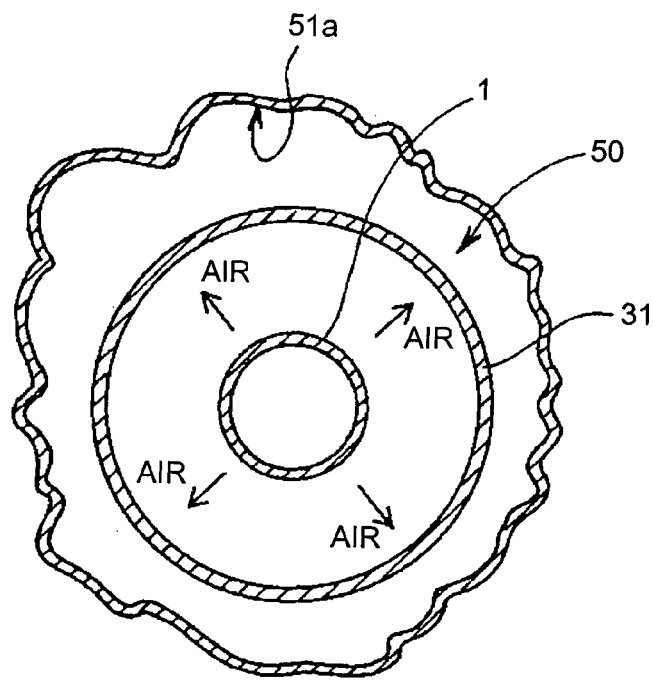
FIG. 5 is a sectional view along line V-V of FIG. 4.

FIGS. 3 and 4 are enlarged sectional views of the distal end portion of the inserted shape detecting probe of FIG. 2, to which the resin member (balloon 31) is attached. In particular, FIG. 3 shows the resin member (balloon 31) in a contracted state. FIGS. 4 and 5 show the inserted shape detecting probe of the present embodiment inserted in an intestinal canal, with the resin member (balloon 31) in an expanded state. FIG. 5 is a sectional view along line V-V of FIG. 4. In FIGS. 3 to 5, structural members inside the inserted shape detecting probe 1 are not shown.

As shown in FIGS. 3 and 4, plural through holes 1a are formed at predetermined positions near the distal end portion of the inserted shape detecting probe 1. These positions are covered by the balloon 31. Further, a slight gap 1b is left between an inner wall surface of the outer sheath 20 of the inserted shape detecting probe 1 and an outer circumferential surface of each of the source coils 21 and the inner sheaths 24. The gap 1b runs continuously from the distal end portion of the inserted shape detecting probe 1 up to the connector portion 22 at the proximal end portion.

When a pump 7a (not shown in FIG. 1; see FIG. 3) which serves as a fluid supply unit of the inserted shape detecting apparatus 7 (FIG. 1) is drive controlled to deliver the fluid, such as gas and liquid, inside the inserted shape detecting probe 1 through the connector portion 22 from a side of the pump 7a, the fluid passes through the gap 1b and reaches the distal end portion of the inserted shape detecting probe 1. Eventually, the fluid is discharged from the plural through holes 1a. The fluid, then, expands the balloon 31. The balloon 31 transforms from the contracted state shown in FIG. 3 to a substantially spherical shape as shown in FIGS. 4 and 5. On the other hand, when the pump 7a of the inserted shape detecting apparatus 7 is drive controlled to suck the fluid inside the inserted shape detecting probe 1 to the side of the pump 7a, the balloon 31 transforms into the contracted state as shown in FIG. 3.

An operation at the use of the inserted shape detecting probe 1 as the endoscope insertion assistant probe of the present embodiment having the above-described structure will be described below.

FIGS. 6 to 13 are explanatory diagrams of the insertion of the endoscope insertion assistant probe into the body cavity in the inserted shape detecting apparatus system which includes the endoscope insertion assistant probe (inserted shape detecting probe 1) of the present embodiment. Specifically, FIGS. 6, 8, 10, and 12 show the endoscope insertion assistant probe (inserted shape detecting probe 1) and the insertion portion of the endoscope, both being inserted into a large intestine and an intestinal canal thereof. FIGS. 7, 9, 11, and 13 show images that are displayed on the display screen of the monitor of the inserted shape detecting apparatus and the image represents an inserted shape of the endoscope insertion assistant probe in a specific state shown in each of FIGS. 6, 8, 10, and 12.

First, the inserted shape detecting probe 1 to which the balloon 31 is attached at the distal end is inserted into and arranged inside the treatment instrument insertion channel 15 from the treatment instrument insertion opening 14 formed in the operation portion 12 of the endoscope 3. The balloon 31 is in the contracted state. The inserted shape detecting probe 1 is arranged so that the distal end portion of the inserted shape detecting probe 1 does not protrude from the most distal end portion of the insertion portion 11. Then, the insertion portion 11 of the endoscope 3 is inserted into the body cavity of the subject.

Specifically, the insertion portion 11 of the endoscope 3 is inserted into a rectum 52 from an anus 51 of the subject (see FIG. 6), for example. After the insertion portion 11 is inserted into the body cavity of the subject by a predetermined amount, the insertion portion 11 of the endoscope is held at the position so as not to move. While the insertion portion 11 is held still, the distal end portion of the inserted shape detecting probe 1 is made to protrude in a forward direction by a predetermined amount from the most distal end portion of the insertion portion 11, so that a portion where the balloon 31 is attached is exposed.

Then, the balloon 31 is expanded. For the expansion of the balloon 31, the drive control of the pump 7a (see FIG. 3) of the inserted shape detecting apparatus 7 (see FIG. 1) is started, whereby the fluid, i.e., gas or liquid, is delivered from the side of the pump 7a to the inside of the inserted shape detecting probe 1. The fluid passes through the gap 1b inside the inserted shape detecting probe 1 to reach the distal end portion of the probe 1, and eventually is discharged from the plural through holes 1a to the outside, i.e., to the inside of the balloon 31. When the balloon 31 expands to a predetermined size, the drive control of the pump 7a (see FIG. 3) is stopped. The predetermined size of the balloon 31 is set so that a diameter of the balloon 31 is smaller than a minimum diameter of a section enclosed by an intestine wall 50a inside the intestinal canal 50, for example, as shown in FIGS. 4 and 5.

Thus, the balloon 31 of the inserted shape detecting probe 1 is brought into an expanded state (state shown in FIGS. 4 and 5). While the balloon 31 is in the expanded state, a negative pressure of a predetermined level is applied to the balloon 31 from the side of the pump 7a so that the fluid in the balloon 31 does not flow back. Thus, the balloon 31 is maintained in a substantially spherical shape.

Then, the operator pushes only the inserted shape detecting probe 1 from a side of the treatment instrument insertion opening 14 of the operation portion 12 while the balloon 31 attached to the distal end portion of the inserted shape detecting probe 1 is expanded. The probe 1 advances inside the rectum 52. During the advancement of the probe 1, the balloon 31 advances accordingly and sometimes comes into contact with an uneven surface of the intestine wall 50a of the intestinal canal 50 of the rectum 52. The balloon 31, however, has a sufficiently large substantially spherical shape in comparison with the size of the unevenness of the intestine wall 50a. Therefore, the balloon 31 is not caught by the unevenness of the intestine wall 50a. Rather, the balloon 31 smoothly moves along the intestine wall 50a and is inserted farther into the rectum as if sliding on tips of the uneven surface of the intestine wall 50a.

When the inserted shape detecting probe 1 reaches a predetermined position inside the rectum 52, the insertion portion 11 is made to advance along the inserted shape detecting probe 1. Here, only the insertion portion 11 is made to advance while the inserted shape detecting probe 1 is held at the position. When the distal end portion of the insertion portion 11 comes close to the region where the balloon 31 of the inserted shape detecting probe 1 is placed, the insertion portion 11 is held at the position again so as not to move. Then, the inserted shape detecting probe 1 alone is made to advance while the insertion portion 11 is held at the position.

Figure 6:
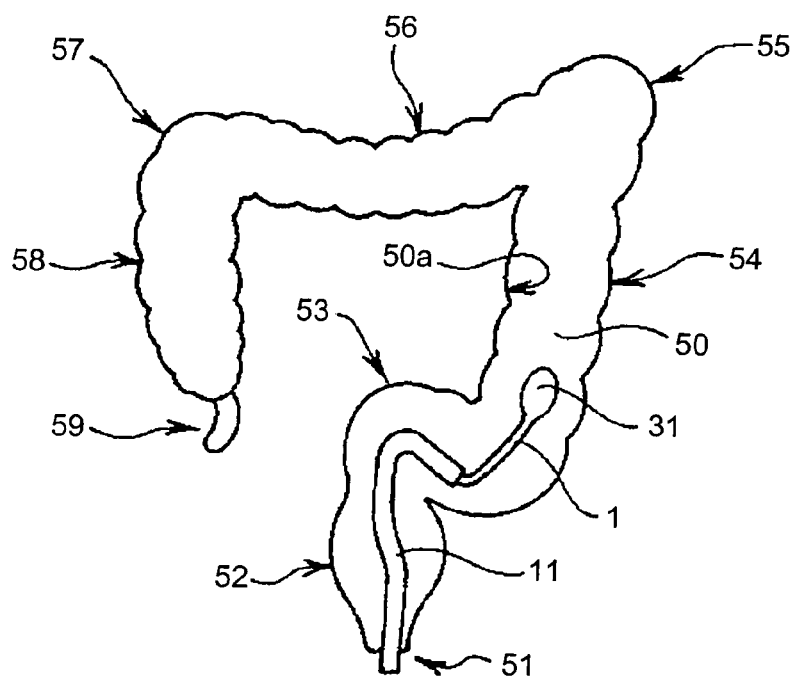
FIG. 6 is an explanatory view illustrating an insertion operation of the inserted shape detecting probe of FIG. 2 inside the body cavity, and shows the inserted shape detecting probe and the insertion portion of the endoscope both inserted inside a large intestine and an intestinal canal thereof.
Figure 7:
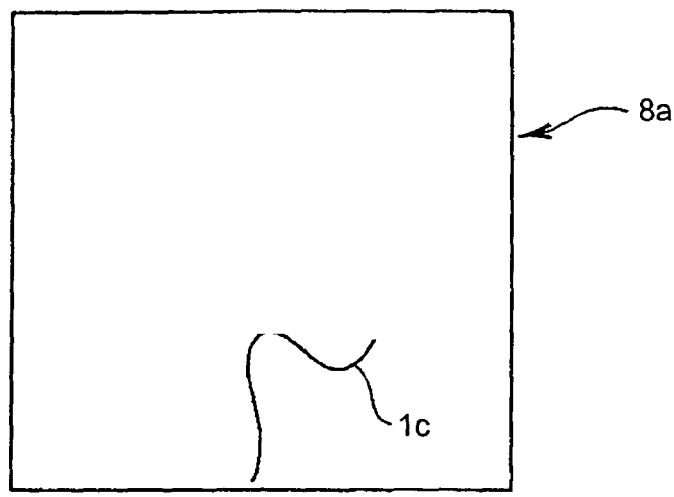
FIG. 7 illustrates how an inserted shape of the inserted shape detecting probe is displayed on a display screen of a monitor of an inserted shape detecting apparatus when the inserted shape detecting probe is at a position shown in FIG. 6.

After passing through the rectum 52, the balloon 31 of the inserted shape detecting probe 1 reaches a curved sigmoid colon 53. The distal end portion of the balloon 31 abuts against a curved portion of the sigmoid colon 53. Since the balloon 31 is substantially spherical, the balloon 31 moves along the curved shape of the sigmoid colon 53 along the intestine wall 50a. The balloon 31 of the inserted shape detecting probe 1 passes through the sigmoid colon 53 and moves through a descending colon 54, to come close to a splenic flexure 55. FIG. 6 shows the inserted shape detecting probe 1 in this state. At this point, the inserted shape detecting apparatus 7 shows an image on the display screen 8a of the monitor 8 as shown in FIG. 7. A line denoted by reference character 1c on the display screen 8a represents the shape of the inserted shape detecting probe 1. The operator can visually confirm the shape of the inserted shape detecting probe 1 at the time by looking at the display screen 8a.

When the inserted shape detecting probe 1 reaches the state shown in FIG. 6, the insertion portion 11 is made to advance along the inserted shape detecting probe 1 again. The operator operates the insertion portion 11 while referring to the display screen 8a of the monitor 8 as shown in FIG. 7.

Figure 8:
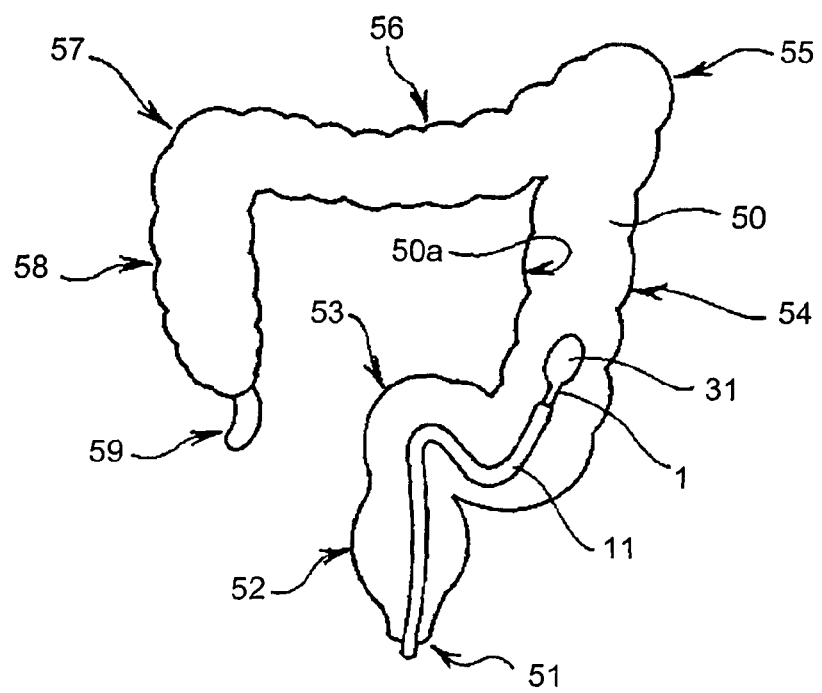
FIG. 8 is an explanatory view illustrating the insertion operation of the inserted shape detecting probe of FIG. 2 inside the body cavity, and shows the inserted shape detecting probe and the insertion portion of the endoscope both inserted inside a large intestine and an intestinal canal thereof.
Figure 9:
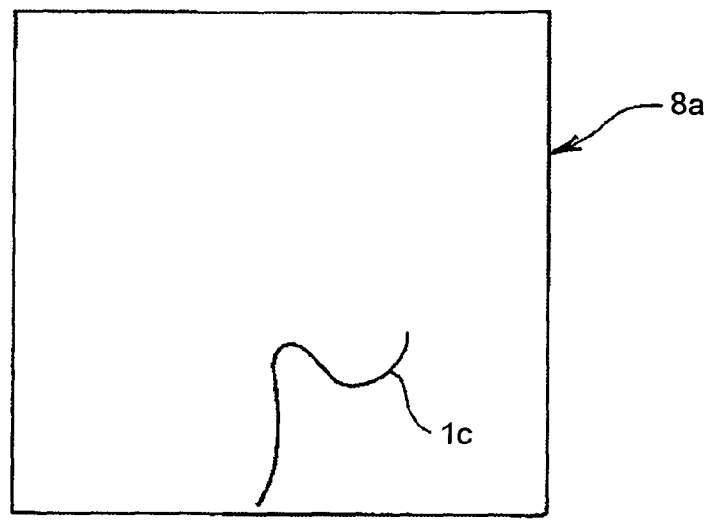
FIG. 9 illustrates how the inserted shape of the inserted shape detecting probe is displayed on the display screen of the monitor of the inserted shape detecting apparatus when the inserted shape detecting probe is at a position shown in FIG. 8.
Figure 10:
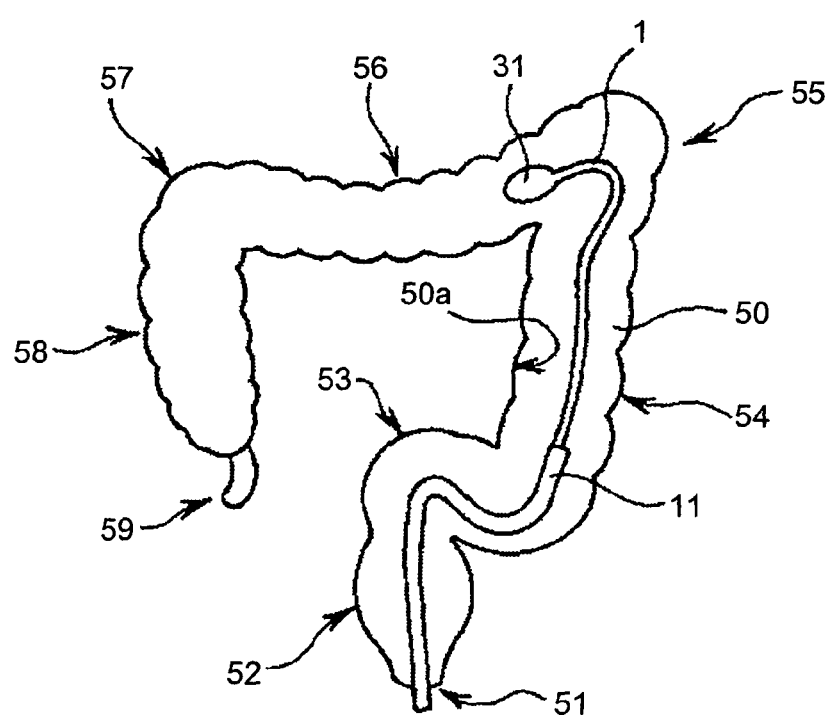
FIG. 10 is an explanatory view illustrating the insertion operation of the inserted shape detecting probe of FIG. 2 inside the body cavity, and shows the inserted shape detecting probe and the insertion portion of the endoscope both inserted inside a large intestine and an intestinal canal thereof.
Figure 11:
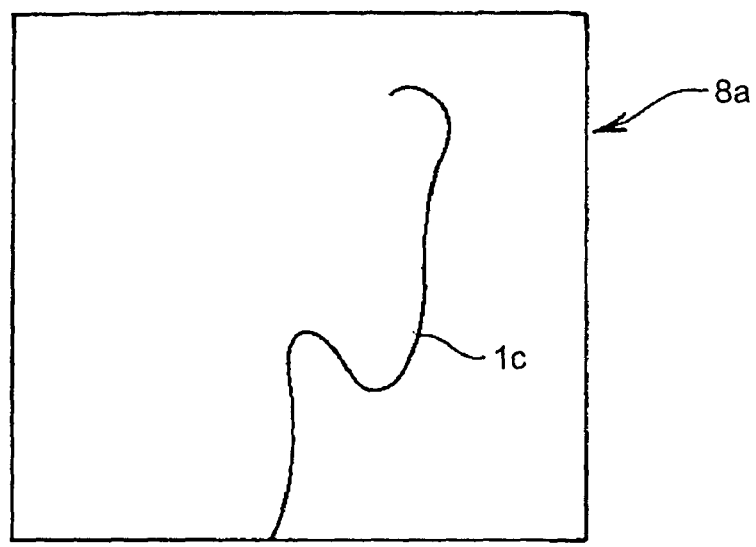
FIG. 11 illustrates how the inserted shape of the inserted shape detecting probe is displayed on the display screen of the monitor of the inserted shape detecting apparatus when the inserted shape detecting probe is at a position shown in FIG. 10.

When the distal end of the insertion portion 11 comes close to the region where the balloon 31 resides, the insertion of the insertion portion 11 is stopped. Then, the inserted shape detecting probe 1 alone is made to advance. Thus, the state shown in FIG. 8 is achieved. At this point, the inserted shape detecting apparatus 7 displays an image on the display screen 8*a* of the monitor 8 as shown in FIG. 9, and the operator can confirm the shape of the inserted shape detecting probe 1 at the time.

Figure 12:
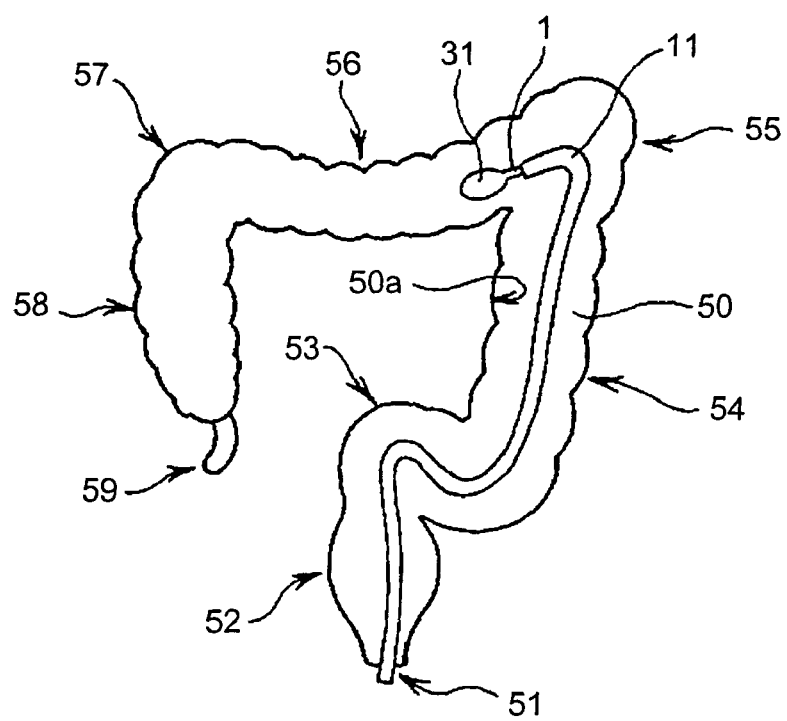
FIG. 12 is an explanatory view illustrating the insertion operation of the inserted shape detecting probe of FIG. 2 inside the body cavity, and shows the inserted shape detecting probe and the insertion portion of the endoscope both inserted inside a large intestine and an intestinal canal thereof.
Figure 13:
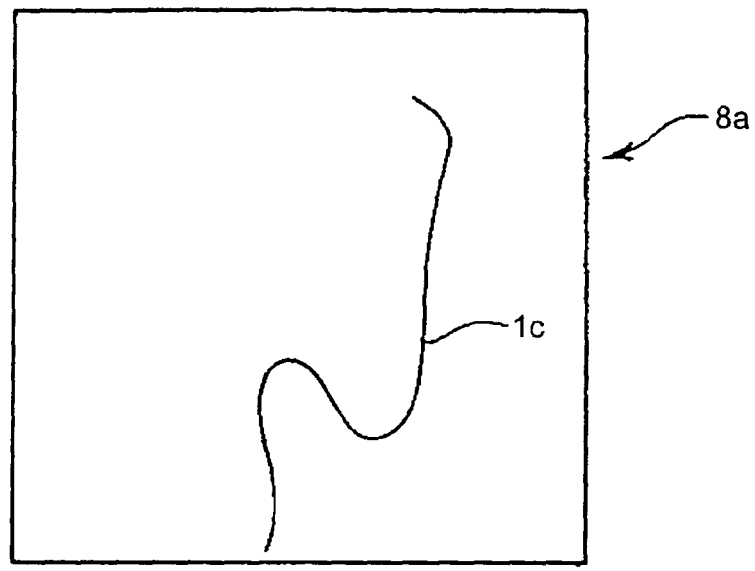
FIG. 13 illustrates how the inserted shape of the inserted shape detecting probe is displayed on the display screen of the monitor of the inserted shape detecting apparatus when the inserted shape detecting probe is at a position shown in FIG. 12.

The inserted shape detecting probe 1 is kept inserted independently while the insertion portion 11 is held at the position. Eventually, the balloon 31 reaches the splenic flexure 55 and passes a curved portion of the splenic flexure 55. As described above, the balloon 31 moves smoothly along the intestine wall 50*a* because of the substantially spherical shape thereof. The travel direction of the inserted shape detecting probe 1 is changed along the shape of the intestine wall 50*a*, and the probe 1 moves in a direction along the intestinal canal 50. When the balloon 31 reaches a region shown in FIG. 10, for example, the insertion portion 11 is made to advance along the probe 1. The operator moves the insertion portion 11 while referring to the display screen 8*a* of the monitor 8 shown in FIG. 11. As shown in FIG. 12, when the distal end portion of the insertion portion 11 reaches the balloon 31 of the inserted shape detecting probe 1 again, the insertion of the balloon 31 of the inserted shape detecting probe 1 is resumed. FIG. 13 shows an image on the display screen 8*a* corresponding to the state shown in FIG. 12.

Subsequently, the operation proceeds as described above with the alternate advancement of the inserted shape detecting probe 1 and the insertion portion 11 toward a direction of insertion. The inserted shape detecting probe 1 and the insertion portion 11 move through a transverse colon 56, a hepatic flexure 57, and an ascending colon 58, until eventually reach a position next to an appendix 59.

While the inserted shape detecting probe 1 and the insertion portion 11 stay at the position described above, the pump 7*a* of the inserted shape detecting apparatus 7 is drive controlled, so that the fluid inside the inserted shape detecting probe 1 is sucked out toward the side of the pump 7*a*. Then, the balloon 31 is turned into the contracted state as shown in FIG. 3. The inserted shape detecting probe 1 is pulled inside the treatment instrument insertion channel 15. At this point, the inserted shape detecting probe 1 may be completely pulled out from the treatment instrument insertion channel 15. Alternatively, the inserted shape detecting probe 1 is pulled so that at least the distal end portion (portion where the balloon 31 is attached) of the inserted shape detecting probe 1 does not stick out from the distal end portion of the insertion portion 11. With such operation, a preparation is completed for the observation and examination with the insertion portion 11 of the endoscope 3.

The inserted shape detecting probe 1 may be employed as the endoscope insertion assistant probe of the present embodiment in a different manner as described below from the manual operation described above.

FIGS. 14 to 21 are explanatory diagrams of another exemplary operation for inserting the endoscope insertion assistant probe inside the body cavity in the inserted shape detecting apparatus system which includes the endoscope insertion assistant probe (inserted shape detecting probe 1) of the present embodiment. FIGS. 14, 16, 18, and 20 show the endoscope insertion assistant probe (inserted shape detecting probe 1) and the insertion portion of the endoscope both inserted into the large intestine and the intestinal canal thereof in a specific state. FIGS. 15, 17, 19, and 21 show images displayed on the display screen of the monitor of the inserted shape detecting apparatus and represent the inserted shape of the endoscope insertion assistant probe (inserted shape detecting probe 1) in the respective states shown in FIGS. 14, 16, 18, and 20.

Here, after the inserted shape detecting probe 1 is inserted inside the body cavity from the anus 51, the balloon 31 is made to advance through the rectum 52, the sigmoid colon 53, the descending colon 54, the splenic flexure 55, the transverse colon 56, the hepatic flexure 57, the ascending colon 58, and is eventually placed at the position next to the appendix 59. The operator inserts the insertion portion 11 up to the position next to the appendix 59 while referring to the display screen 8*a* as a guide. Hereinbelow, an operation which is similar to the manual operation described above will not be described in detail and just briefly mentioned. Different part of the operation will be mainly described in detail below.

Similarly to the manual operation described above, the inserted shape detecting probe 1 is inserted inside the treatment instrument insertion channel 15 from the treatment instrument insertion opening 14 and arranged inside the treatment instrument insertion channel 15. The insertion portion 11 in which the inserted shape detecting probe 1 is placed is inserted into the body cavity of the subject, for example from the anus 51 (see FIG. 4) of the subject into the rectum 52.

After the insertion portion 11 is inserted into the body cavity of the subject by a predetermined amount, the insertion portion 11 is held at the position. The inserted shape detecting probe 1 is pushed further inside until the distal end portion thereof comes to protrude by a predetermined amount from the most distal end portion of the insertion portion 11. The amount of protrusion is set so that the portion where the balloon 31 is attached is exposed, similarly to the manual operation described above.

Then, the pump 7*a* (see FIG. 3) of the inserted shape detecting apparatus 7 (see FIG. 1) is drive controlled, so as to expand the balloon 31.

The inserted shape detecting probe 1 is pushed inside from the side of the treatment instrument insertion opening 14, while the balloon 31 provided at the distal end portion thereof is expanded. The probe 1 then advances inside the rectum 52. The balloon 31 keeps advancing smoothly along the intestine wall 50*a* without being caught by the unevenness of the intestine wall 50*a*.

Figure 14:
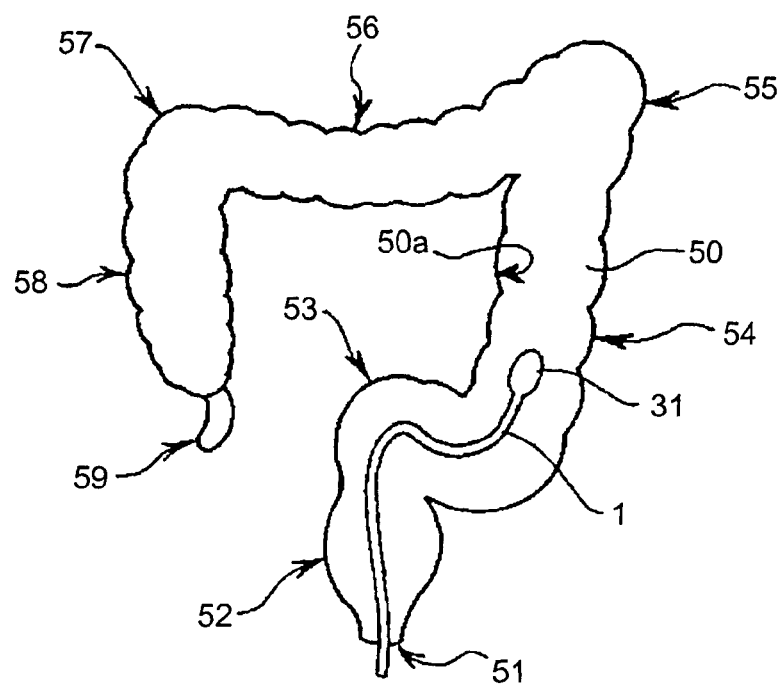
FIG. 14 is an explanatory view illustrating another insertion operation of the inserted shape detecting probe of FIG. 2 inside the body cavity, and shows the inserted shape detecting probe and the insertion portion of the endoscope both inserted inside a large intestine and an intestinal canal thereof.
Figure 15:
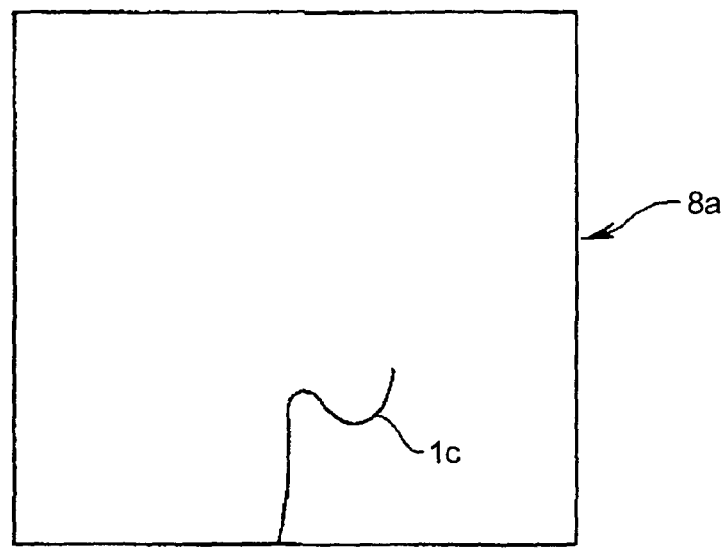
FIG. 15 illustrates how the inserted shape of the inserted shape detecting probe is displayed on the display screen of the monitor of the inserted shape detecting apparatus when the inserted shape detecting probe is at a position shown in FIG. 14.

As the insertion of the inserted shape detecting probe 1 proceeds, the balloon 31 of the inserted shape detecting probe 1 passes through the rectum 52 to reach the sigmoid colon 53. The balloon 31 smoothly passes through the sigmoid colon 53 because of the substantially spherical shape thereof, moves through the descending colon 54, and comes close to the splenic flexure 55. FIG. 14 shows the state at this point. At this point, the inserted shape detecting apparatus 7 displays an image on the display screen 8*a* of the monitor 8 as shown in FIG. 15.

Figure 16:
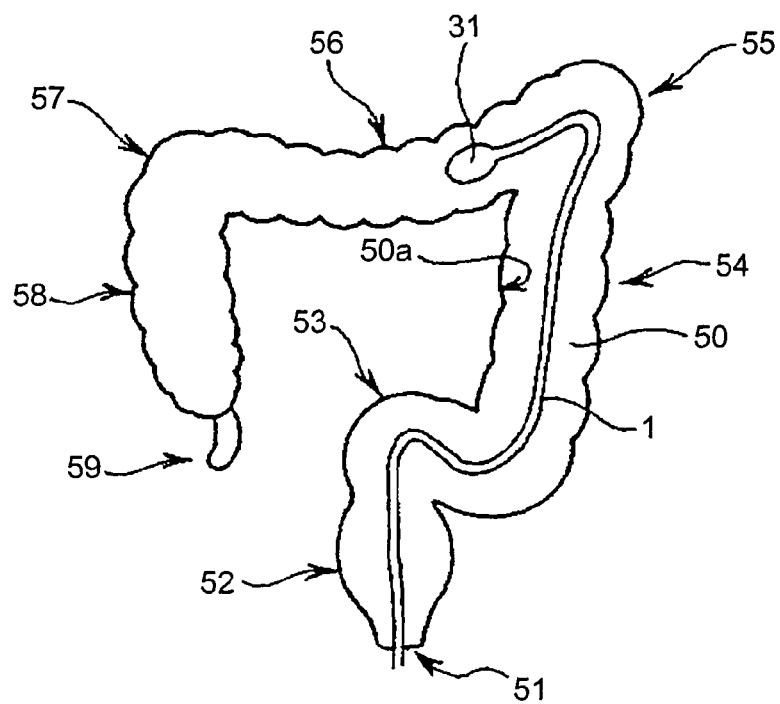
FIG. 16 is an explanatory view illustrating the another insertion operation of the inserted shape detecting probe of FIG. 2 inside the body cavity, and shows the inserted shape detecting probe and the insertion portion of the endoscope both inserted inside a large intestine and an intestinal canal thereof.
Figure 17:
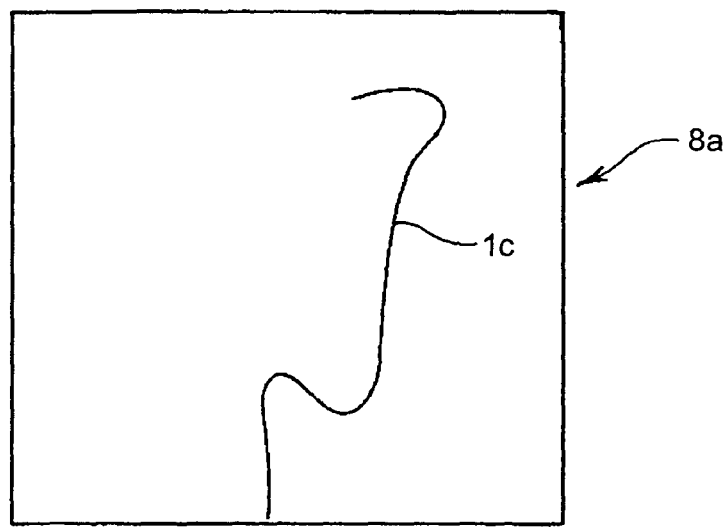
FIG. 17 illustrates how the inserted shape of the inserted shape detecting probe is displayed on the display screen of the monitor of the inserted shape detecting apparatus when the inserted shape detecting probe is at a position shown in FIG. 16.

When the insertion of the inserted shape detecting probe 1 continues after the probe 1 reaches the state of FIG. 14, the balloon 31 of the probe 1 reaches the splenic flexure 55, passes smoothly along the curved portion of the splenic flexure 55, and comes close to the transverse colon 56. Such state is shown in FIG. 16. At this point, an image as shown in FIG. 17 is shown on the display screen 8*a* of the monitor 8.

Figure 18:
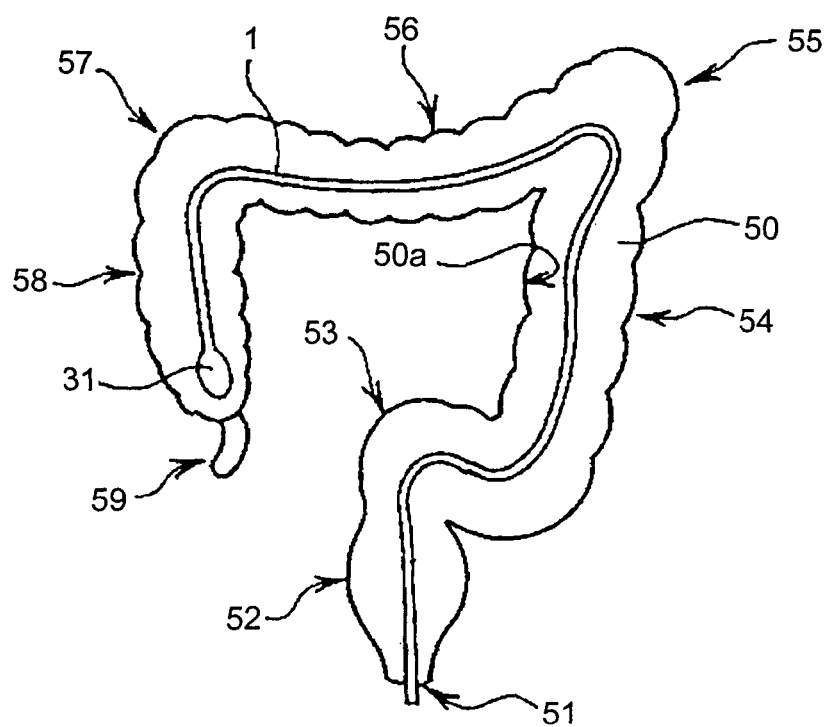
FIG. 18 is an explanatory view illustrating the another insertion operation of the inserted shape detecting probe of FIG. 2 inside the body cavity, and shows the inserted shape detecting probe and the insertion portion of the endoscope both inserted inside a large intestine and an intestinal canal thereof.
Figure 19:
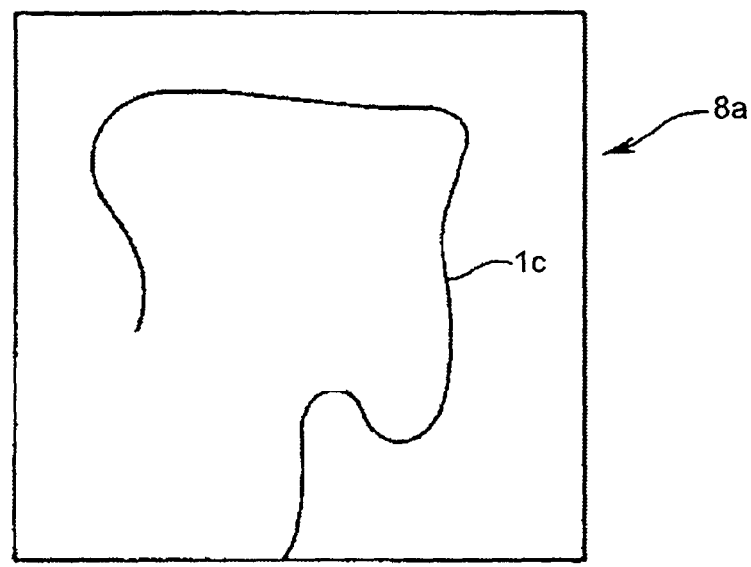
FIG. 19 illustrates how the inserted shape of the inserted shape detecting probe is displayed on the display screen of the monitor of the inserted shape detecting apparatus when the inserted shape detecting probe is at a position shown in FIG. 18.
Figure 20:
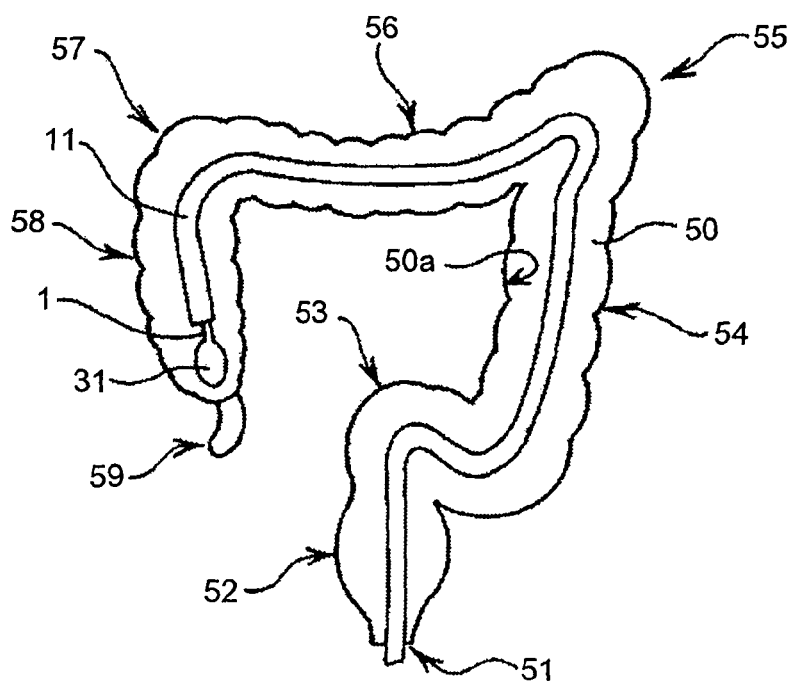
FIG. 20 is an explanatory view illustrating the another insertion operation of the inserted shape detecting probe of FIG. 2 inside the body cavity, and shows the inserted shape detecting probe and the insertion portion of the endoscope both inserted inside a large intestine and an intestinal canal thereof.
Figure 21:
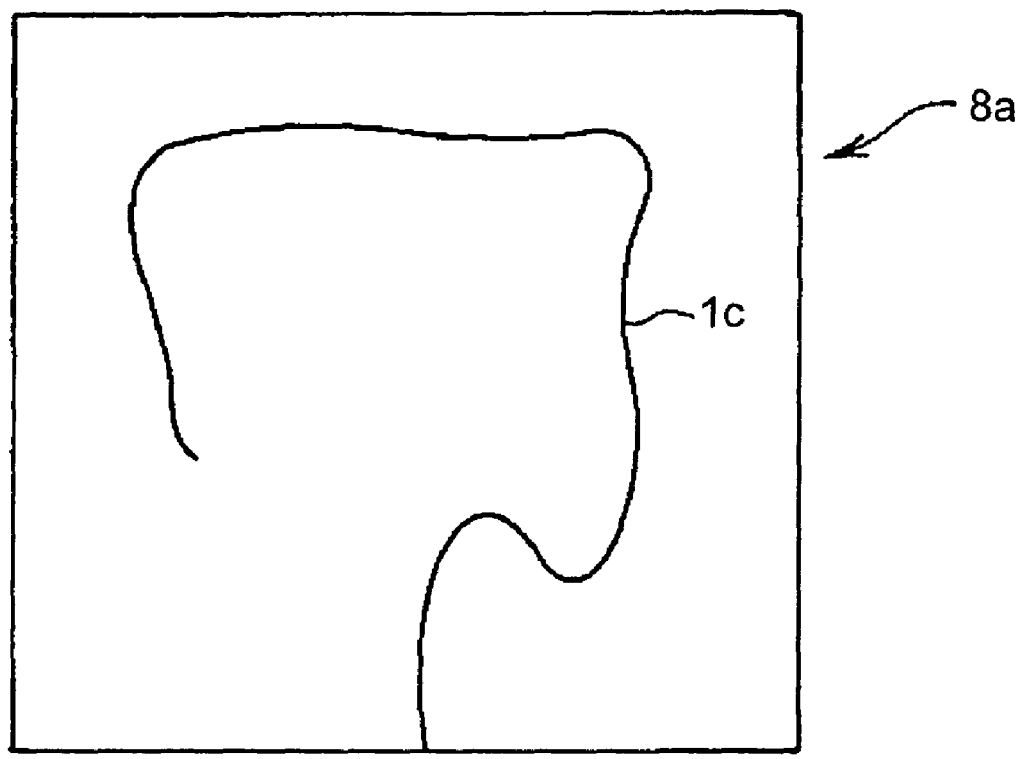
FIG. 21 illustrates how the inserted shape of the inserted shape detecting probe is displayed on the display screen of the monitor of the inserted shape detecting apparatus when the inserted shape detecting probe is at a position shown in FIG. 20.

When the insertion of the inserted shape detecting probe 1 continues further, the balloon 31 of the probe 1 passes through the hepatic flexure 57, advances through the ascending colon 58, and eventually comes next to the appendix 59. FIG. 18 shows the state at this point. Then, an image is displayed on the display screen 8*a* of the monitor 8 as shown in FIG. 19.

At such state, the insertion of the insertion portion 11 is started. The insertion portion 11 is inserted along the inserted shape detecting probe 1 which serves as a guide. Here, the operator can refer to the inserted shape of the inserted shape detecting probe 1 displayed on the display screen 8*a* (see FIG.

19) of the monitor 8. Therefore, the operator can insert the insertion portion 11 up to a desired region inside the body cavity easily and smoothly.

While the inserted shape detecting probe 1 and the insertion portion 11 are arranged at a desired position in the body cavity, for example, at the position next to the appendix 59 as described above, the pump 7a of the inserted shape detecting apparatus 7 is drive controlled, so that the fluid inside the inserted shape detecting probe 1 is sucked to the side of the pump 7a, similarly to the procedure in the above described manual operation. Then, the balloon 31 is turned to the contracted state (see FIG. 3). The inserted shape detecting probe 1 is pulled inside the treatment instrument insertion channel 15. Thus, the preparation is completed for the observation and examination with the insertion portion 11 of the endoscope 3.

According to the first embodiment as described above, the inserted shape detecting apparatus system can be realized, in which; the inserted shape detecting probe 1 is inserted inside the intestinal canal 50 in advance as the endoscope insertion assistant probe; data is obtained from the inserted shape detecting probe 1; an image signal is generated by the inserted shape detecting apparatus 7 based on the obtained data; the inserted shape of the inserted shape detecting probe 1 is displayed on the monitor 8; and the operator can safely and securely insert and advance the insertion portion 11 of the endoscope 3 inside the intestinal canal 50 inside the body cavity while referring to the display of the inserted shape.

Here, the inserted shape detecting probe 1 which is employed as the endoscope insertion assistant probe is structured so that the balloon 31, which is a flexible, expandable, thin-film-like, elastic member, can be attached to the distal end portion thereof. The balloon 31 can be optionally turned into the expanded state of a predetermined size or to the contracted state through the drive control of the pump 7a by the inserted shape detecting apparatus 7, when desired.

The balloon 31 is expanded when the inserted shape detecting probe 1 is inserted inside the intestinal canal 50 inside the body cavity. Therefore, the distal end portion of the inserted shape detecting probe 1, which advances inside the intestinal canal 50, is not caught by the unevenness of the intestine wall 50a. In addition, the distal end portion of the inserted shape detecting probe 1 does not abut against the curved portion of the intestinal canal 50. Therefore, the advancement of the inserted shape detecting probe 1 is not hampered and the inserted shape detecting probe 1 does not damage the intestine wall 50a. Thus, the inserted shape detecting probe 1 can smoothly advance along the curved shape of the intestinal canal 50.

The operator can insert the insertion portion 11 of the endoscope 3 along the inserted shape detecting probe 1 while referring to the inserted shape of the inserted shape detecting probe 1 whose shape is displayed on the display screen 8a of the monitor 8. Therefore, the operator can insert the insertion portion 11 up to a desired region inside the body cavity easily and smoothly.

On the other hand, some endoscopes have an insertion position detecting member in a portion near the distal end of the insertion portion, for example. How the endoscope insertion assistant probe according to the first embodiment described above is employed in the inserted shape detecting apparatus system that includes the endoscope of such type will be described below.

Figure 22:
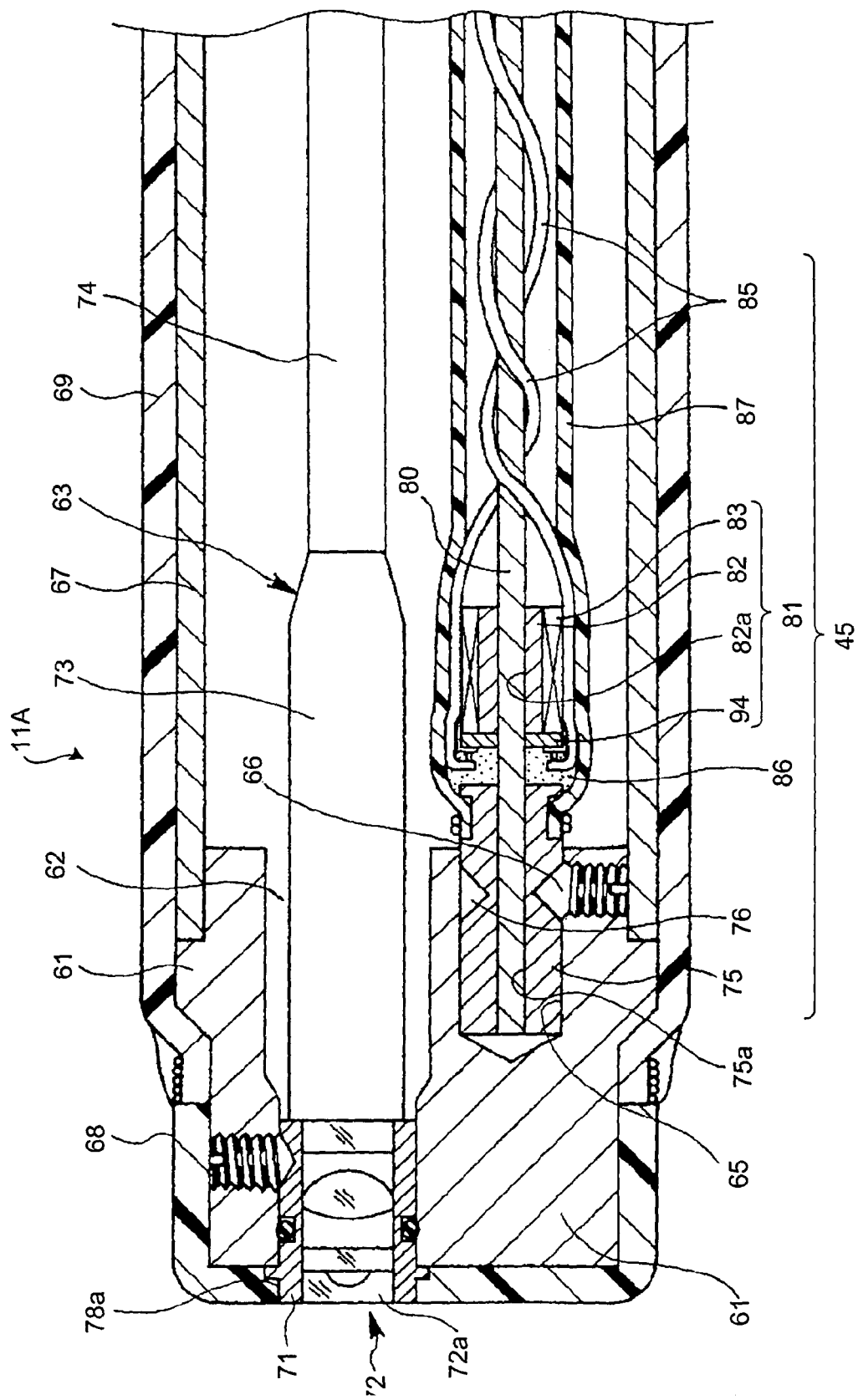
FIG. 22 shows one modification of the first embodiment of the present invention, and is an enlarged sectional view of a relevant portion, in particular, a distal end portion of an insertion portion of an endoscope in an inserted shape detecting apparatus system to which the endoscope insertion assistant probe of the first embodiment is applied.

FIG. 22 shows a modification of the first embodiment of the present invention, and is an enlarged sectional view of a relevant portion, in particular, the distal end portion of the insertion portion of the endoscope in the inserted shape detecting apparatus system to which the endoscope insertion assistant probe of the first embodiment is applied.

The modification is different from the inserted shape detecting apparatus system of the first embodiment described above shown in FIG. 1 only in the shape of the insertion portion of the endoscope. Therefore, elements of the modification which are the same as the elements of the first embodiment will be denoted by the same reference characters and will not be described in detail. Only different elements will be described below.

A distal end portion of an insertion portion 11A of an endoscope of an inserted shape detecting apparatus system of the modification is structured as follows. Specifically, the distal end portion includes a distal end portion main body 61, a cylindrical frame 67, a distal end cover 68, an outer tube 69, and the like. The distal end portion main body 61 includes a hole (not shown) in which an illumination window is to be formed, a hole 62 in which an observation and imaging window is to be formed, an imaging unit 63, a distal end portion position detecting unit 45 which is an insertion position detecting member, and the like. The cylindrical frame 67 is arranged at a back end side of the distal end portion main body 61 around an outer circumference thereof, and houses the imaging unit 63 and the like inside. The distal end cover 68 covers a front end side of the distal end portion main body 61. The outer tube 69 covers a back end side portion of the distal end portion main body 61 and an outer circumference of the cylindrical frame 67.

The imaging unit 63 includes an objective lens system 72 attached to a lens frame 71, an imager 73 having an imaging element such as a charge coupled device (CCD) or the like arranged at a focusing position of the objective lens system 72, for example. A signal cable 74 extends from a back end of the imager 73. A first lens 72a of the objective lens system 72 is bonded to a front end wall of the lens frame 71. The lens frame 71 fits into a hole 78a formed in the distal end cover 68 and is secured to the distal end cover 68 thereby.

The signal cable 74 extends from the insertion portion 11A and the operation portion 12 of the endoscope 3 (see FIG. 1) through the universal cord 13 up to the video processor 4, thereby securing an electric connection between the imaging unit 63 and the video processor 4.

On the other hand, a depression 65 is formed on a back end surface of the distal end portion main body 61. A distal end portion of the distal end portion position detecting unit 45 that detects the position of the distal end portion of the insertion portion 11A is secured in the depression 65 by a screw 66.

On a distal end of the distal end portion position detecting unit 45, a pin 75 is provided. The pin 75 has a V groove 76 formed around an entire circumference of a cylindrical surface thereof. The pin 75 is put into the depression 65 of the distal end portion main body 61, and sequentially, a conical tip end of the screw 66 comes into the V groove 76 of the pin 75. Thus, the distal end portion position detecting unit 45 is securely fixed to the distal end portion main body 61.

The distal end portion position detecting unit 45 includes a supporting member 80 which is provided along an entire length of the distal end portion position detecting unit 45. The pin 75 is fixed at a distal end of the supporting member 80. A coil unit 81 is secured to the supporting member 80 at a back side of the pin 75.

The coil unit 81 includes a coil 83. The coil 83 is made of a conductive wire wound around a core 82 predetermined times. The core 82 is formed from a magnetic material with a high permeability, such as ferrite or permalloy.

A board 94 is bonded to one end of the coil 83 of the coil unit 81. More specifically, the board 94 is bonded to the core 82 at a proximal end side of the coil 83 in the coil unit 81, and the conductive wire of the coil 83 is connected to the board 84.

The pin 75 has a through hole 75a through which the supporting member 80 is arranged. The core 82 has a through hole 82a through which the supporting member 80 is arranged. The supporting member 80 penetrates through the through holes 75a and 82a, and is connected and fixed thereto by adhesive, soldering, or the like at a predetermined position.

A space between the pin 75 and the coil unit 81 is filled with a filler 86 such as silicone, so that a direct contact of the two (pin 75 and coil unit 81) is prevented while a slight deformation of the space is allowed between the two (pin 75 and coil unit 81).

At a back end portion of the pin 75, a distal end of an outer tube 87 is secured. The outer tube 87 covers an outer surface side of the coil unit 81, the signal line 85, the supporting member 80, and the like. The outer tube 87 is arranged in close contact with the outer surfaces of the coil unit 81, the signal line 85, the supporting member 80, and the like. A proximal end portion of the outer tube 87 extends up to the operation portion 12 (see FIG. 1).

Further, on the distal end surface of the insertion portion 11A, holes for channels such as a gas and liquid delivery channel and the treatment instrument insertion channel are formed, though not shown in FIG. 22.

The insertion portion 11A of the endoscope applied to the modification includes the distal end portion position detecting unit 45 and the like that are insertion position detecting members near the distal end portion and has the above-described structure. The structures of the inserted shape detecting apparatus system and the endoscope insertion assistant probe employed therefor are the same as the structures of the first embodiment, if not specified otherwise above.

An operation of the endoscope insertion assistant probe in the inserted shape detecting apparatus system of the modification will be described below.

FIGS. 23 to 30 are explanatory diagrams illustrating an operation according to the modification of the first embodiment of the present invention. Specifically, FIGS. 23, 25, 27, and 29 each show the endoscope insertion assistant probe (inserted shape detecting probe 1) and the endoscope insertion portion both inserted into the large intestine and the intestinal canal thereof in a specific state. FIGS. 24, 26, 28, and 30 show images displayed on the display screen of the monitor of the inserted shape detecting apparatus as an representation of the inserted shape of the endoscope insertion assistant probe (inserted shape detecting probe 1) in the respective state shown in FIGS. 23, 25, 27, and 29.

FIGS. 23, 25, 27, and 29 correspond to FIGS. 6, 8, 10, and 12 of the first embodiment, and FIGS. 24, 26, 28, and 30 correspond to FIGS. 7, 9, 11, and 13 of the first embodiment.

The operation of the modification is substantially similar to the operation of the first embodiment. Only difference is that the position of the distal end portion of the insertion portion 11A is detected based on the presence of the distal end portion position detecting unit 45 at the insertion of the endoscope insertion portion 11A into the body cavity, and that position information of the distal end portion is displayed on the display screen of the monitor 8. The same operation as that of the first embodiment will be only briefly described below, and only the different feature will be described in detail.

Similarly to the operation of the first embodiment described above, the inserted shape detecting probe 1 is inserted inside the treatment instrument insertion channel 15 from the treatment instrument insertion opening 14. Then, the insertion portion 11A is inserted inside the body cavity of the subject, for example, from the anus 51 (see FIG. 23) of the subject into the rectum 52, while the inserted shape detecting probe 1 stays inside the insertion portion 11A.

When the insertion portion 11A is inserted inside the body cavity of the subject by a predetermined amount, the insertion portion 11A is held at the position. Then, the inserted shape detecting probe 1 is pushed inside, so that the distal end portion of the probe 1 protrudes from the most distal end portion of the insertion portion 11A by a predetermined amount. The predetermined amount here is set, similarly to the manual operation described above, so that the portion to which the balloon 31 is attached is exposed.

Then, the pump 7a (see FIG. 3) of the inserted shape detecting apparatus 7 (see FIG. 1) is drive controlled to expand the balloon 31.

Thereafter, the inserted shape detecting probe 1 is pushed inside from the side of the treatment instrument insertion opening 14 while the balloon 31 attached to the distal end portion of the inserted shape detecting probe 1 is in the expanded state. Then, the probe 1 advances inside the rectum 52. The balloon 31 moves smoothly along the intestine wall 50a without being caught by the unevenness of the intestine wall 50a.

Further, as the insertion of the inserted shape detecting probe 1 continues, the balloon 31 of the inserted shape detecting probe 1 passes through the rectum 52 to reach the sigmoid colon 53. The balloon 31 passes smoothly through the sigmoid colon 53 because of the substantially spherical shape thereof, passes through the descending colon 54, and comes close to the splenic flexure 55.

Figure 23:
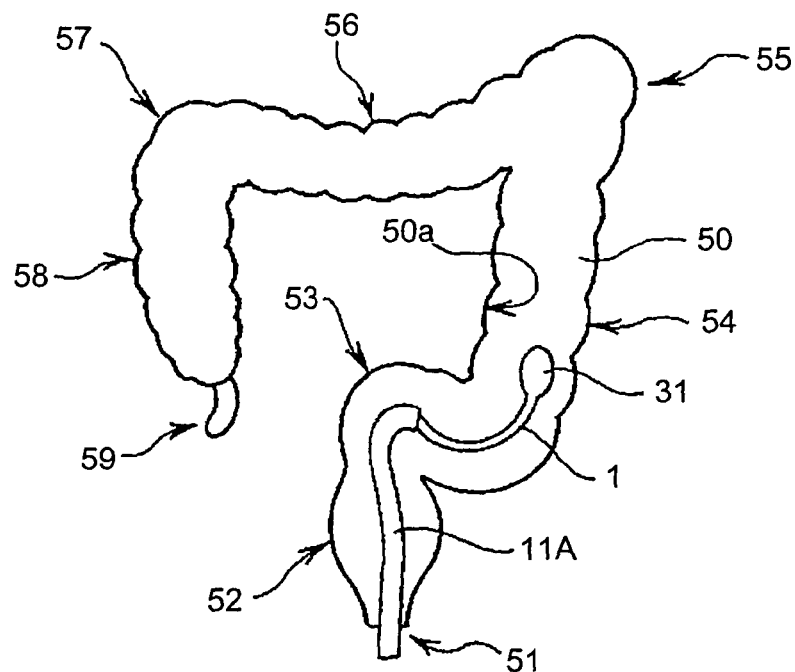
FIG. 23 illustrates an operation of the modification of the first embodiment of the present invention, and shows the inserted shape detecting probe and the insertion portion of the endoscope both inserted inside the large intestine and the intestinal canal thereof.
Figure 24:
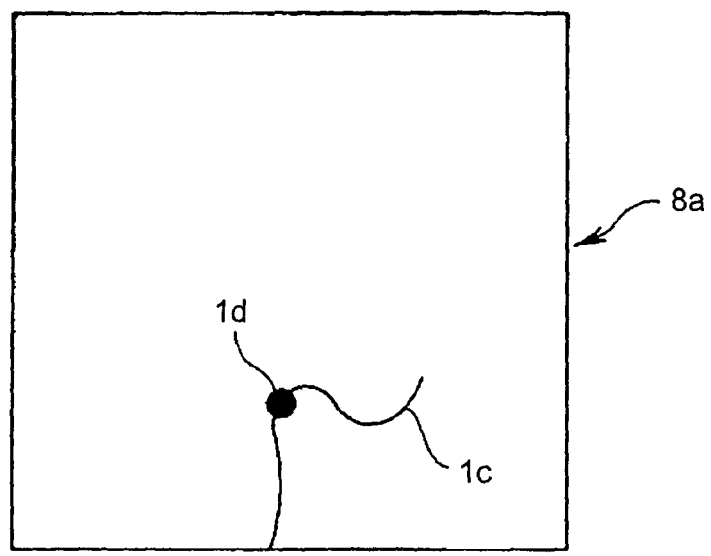
FIG. 24 illustrates how the inserted shape of the inserted shape detecting probe is displayed on the display screen of the monitor of the inserted shape detecting apparatus when the inserted shape detecting probe is at a position shown in FIG. 23.

FIG. 23 shows the state at the point. At this point, the inserted shape detecting apparatus 7 displays an image on the display screen 8a of the monitor 8 as shown in FIG. 24. A line denoted by reference character 1c on the display screen 8a of FIG. 24 represents the shape of the inserted shape detecting probe 1. Thus, the operator can visually confirm the shape of the inserted shape detecting probe 1 at the time.

After the state shown in FIG. 23 is realized, the insertion portion 11A is made to advance further along the inserted shape detecting probe 1. The operator moves the insertion portion 11A while referring to the display screen 8a of the monitor 8 as shown in FIG. 24. Here, along with the insertion of the insertion portion 11A, a dot denoted by reference character 1d appears on the display screen 8a of the monitor 8 of FIG. 24. The dot denoted by 1d represents the position of the distal end portion position detecting unit 45 arranged at the distal end portion of the insertion portion 11A. The operator can easily and visually confirm the position of the distal end portion of the insertion portion 11A with respect to the shape of the inserted shape detecting probe 1 by referring to the display screen 8a of the monitor 8. Thus, the operation of the insertion of the insertion portion 11A becomes easier.

Figure 25:
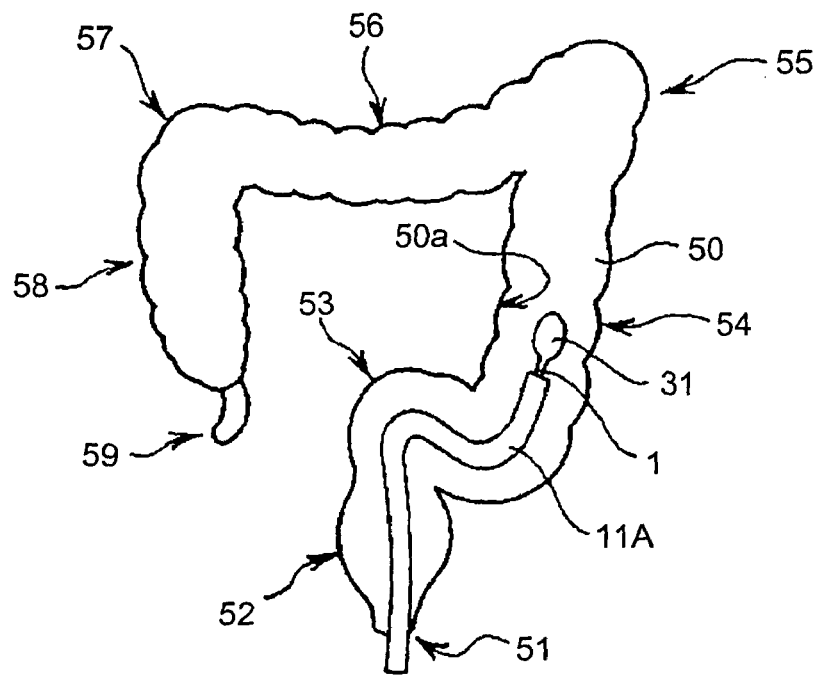
FIG. 25 illustrates an operation of the modification of the first embodiment of the present invention, and shows the inserted shape detecting probe and the insertion portion of the endoscope both inserted inside the large intestine and the intestinal canal thereof.
Figure 26:
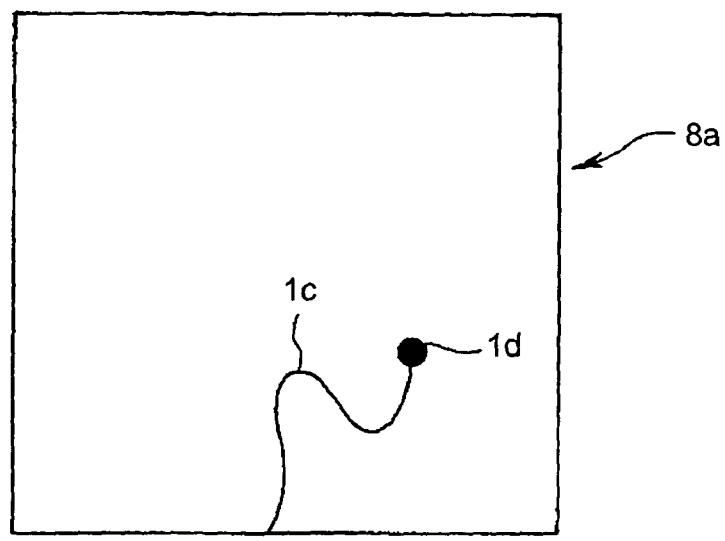
FIG. 26 illustrates how the inserted shape of the inserted shape detecting probe is displayed on the display screen of the monitor of the inserted shape detecting apparatus when the inserted shape detecting probe is at a position shown in FIG. 25.
Figure 27:
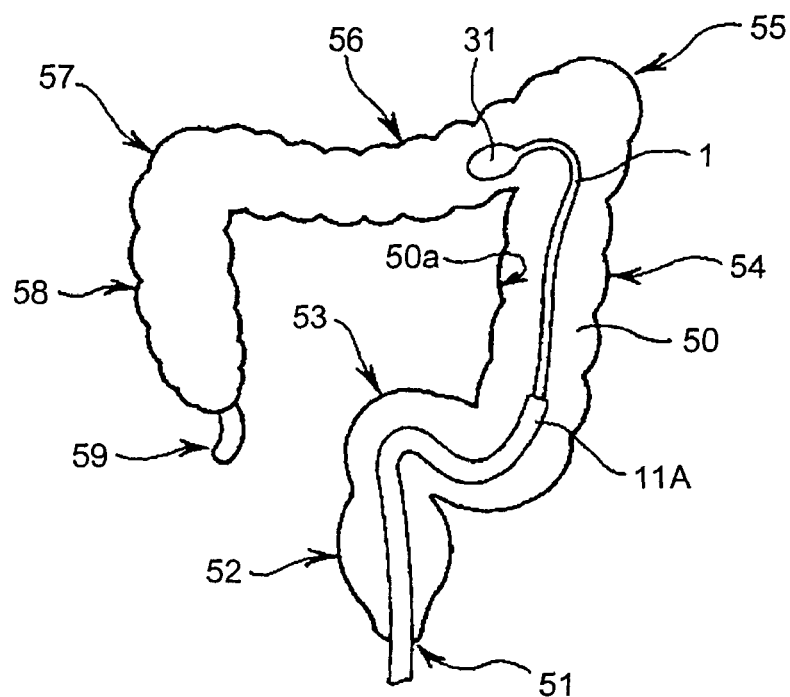
FIG. 27 illustrates an operation of the modification of the first embodiment of the present invention, and shows the inserted shape detecting probe and the insertion portion of the endoscope both inserted inside the large intestine and the intestinal canal thereof.
Figure 28:
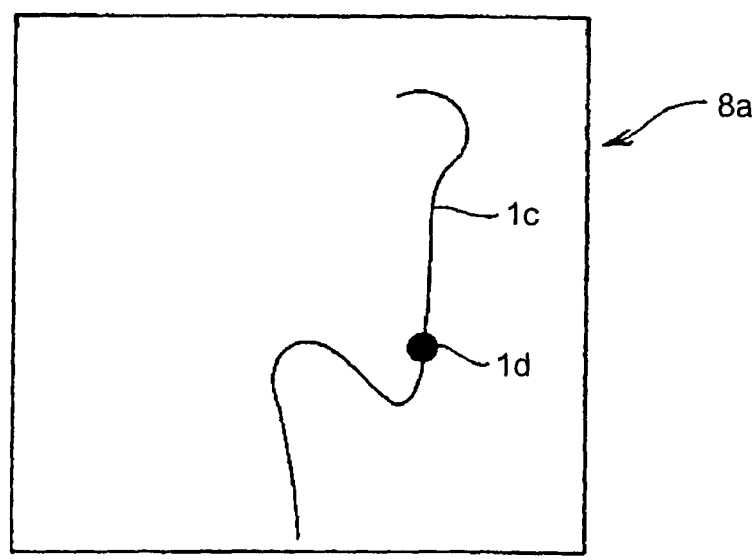
FIG. 28 illustrates how the inserted shape of the inserted shape detecting probe is displayed on the display screen of the monitor of the inserted shape detecting apparatus when the inserted shape detecting probe is at a position shown in FIG. 27.

When the distal end of the insertion portion 11A comes close to the position of the balloon 31, the insertion of the insertion portion 11A is stopped. Subsequently, only the inserted shape detecting probe 1 is made to advance. Then, a state shown in FIG. 25 is realized. At this point, the inserted shape detecting apparatus 7 displays an image on the display screen 8a of the monitor 8 as shown in FIG. 26. The operator can confirm the shape of the inserted shape detecting probe 1 and the position of the distal end portion of the insertion portion 11A at the time.

When the insertion of the inserted shape detecting probe 1 alone continues while the insertion portion 11A is held at the position, the balloon 31 reaches the splenic flexure 55 and passes through the curved portion of the splenic flexure 55. Here, the balloon 31 moves smoothly along the intestine wall 50a because of the substantially spherical shape thereof.

Figure 29:
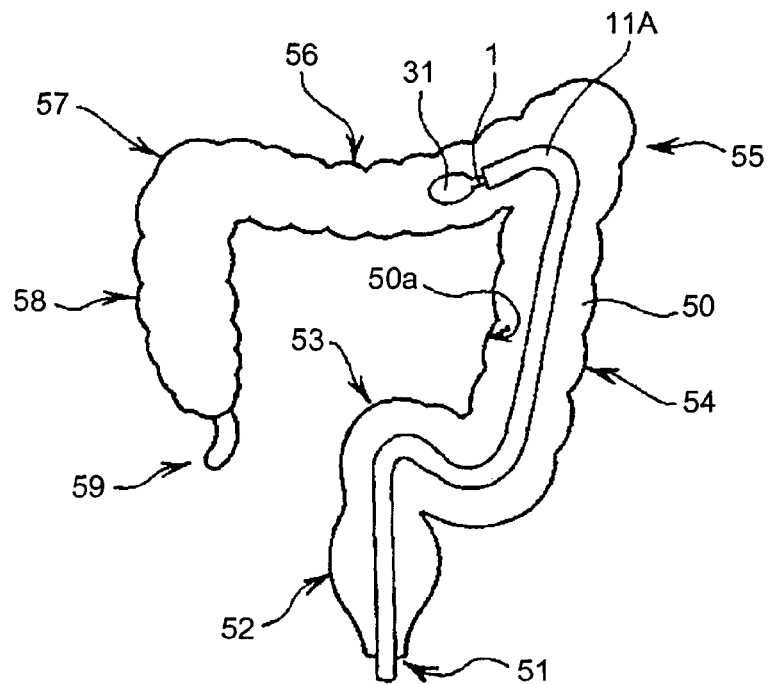
FIG. 29 illustrates an operation of the modification of the first embodiment of the present invention, and shows the inserted shape detecting probe and the insertion portion of the endoscope both inserted inside the large intestine and the intestinal canal thereof.
Figure 30:
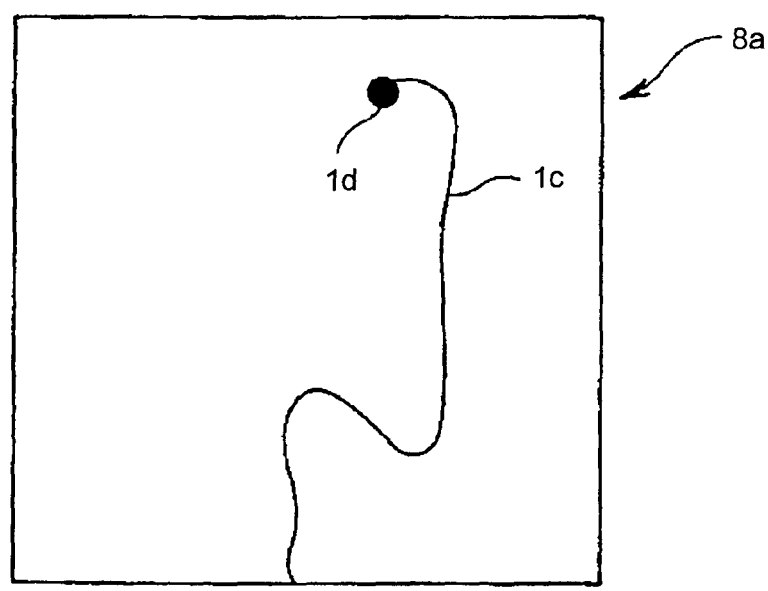
FIG. 30 illustrates how the inserted shape of the inserted shape detecting probe is displayed on the display screen of the monitor of the inserted shape detecting apparatus when the inserted shape detecting probe is at a position shown in FIG. 29.

Along with the advancement of the balloon 31, the travel direction of the inserted shape detecting probe 1 changes, and the probe 1 moves in a direction along the intestinal canal 50. When the balloon 31 reaches a region shown in FIG. 27, for example, the insertion portion 11A is made to advance along the probe 1. The operator moves the insertion portion 11A while referring to the display screen 8a of the monitor 8 of FIG. 28. When the distal end portion of the insertion portion 11A comes close to the balloon 31 of the inserted shape detecting probe 1 as shown in FIG. 29, the insertion of the balloon 31 of the inserted shape detecting probe 1 is started again. FIG. 30 shows an image on the display screen 8a corresponding to the state shown in FIG. 29.

Subsequently, the operation proceeds as described above with the alternate advancement of the inserted shape detecting probe 1 and the insertion portion 11A toward the direction of insertion. The inserted shape detecting probe 1 and the insertion portion 11A move through the transverse colon 56, the hepatic flexure 57, and the ascending colon 58, until eventually reach the position next to the appendix 59. Since the operator can confirm and refer to the inserted shape of the inserted shape detecting probe 1 and the position of the distal end portion of the insertion portion 11A as displayed on the display screen 8a of the monitor 8, the operator can advance the insertion portion 11A up to a desired region inside the body cavity easily and smoothly.

When the inserted shape detecting probe 1 and the insertion portion 11A are eventually arranged in a desired position inside the body cavity, e.g., at the position next the appendix 59 as described above, the pump 7a of the inserted shape detecting apparatus 7 is drive controlled, so that the fluid inside the inserted shape detecting probe 1 is sucked to the side of the pump 7a. Then, the balloon 31 is turned into the contracted state (see FIG. 3). Then, the inserted shape detecting probe 1 is pulled inside the treatment instrument insertion channel 15. Thus, the preparation is completed for the observation and examination with the insertion portion 11A of the endoscope 3.

The operation of the modification can be performed differently as described below from the manual operation described above similarly to the operation of the first embodiment.

FIGS. 31 to 38 are explanatory diagrams illustrating another manner of the operation according to the modification of the first embodiment of the present invention. Specifically, FIGS. 31, 33, 35, and 37 show the endoscope insertion assistant probe (inserted shape detecting probe 1) and the insertion portion of the endoscope both inserted into the large intestine and the intestinal canal thereof in a specific state. FIGS. 32, 34, 36, and 38 show images displayed on the display screen of the monitor of the inserted shape detecting apparatus as representations of the inserted shape of the endoscope insertion assistant probe (inserted shape detecting probe 1) at the respective states shown in FIGS. 31, 33, 35, and 37.

The another manner of the operation of the modification is substantially similar to the another manner of the operation of the first embodiment described above (see FIGS. 14 to 21). The difference lies in that when the endoscope insertion portion 11A is inserted inside the body cavity, the position of the distal end portion of the insertion portion 11A is detected based on the presence of the distal end portion position detecting unit 45, and positional information is displayed on the display screen of the monitor 8. Hereinbelow, the same operation as the another manner of the first embodiment will be only briefly described and a different operation alone will be described in detail.

After the inserted shape detecting probe 1 is inserted inside the body cavity from the anus 51, the balloon 31 moves through the rectum 52, the sigmoid colon 53, the descending colon 54, the splenic flexure 55, the transverse colon 56, the hepatic flexure 57, and the ascending colon 58, to finally reach the position next to the appendix 59. The operator inserts the insertion portion 11A up to the position next to the appendix 59 while referring to the display screen 8a which shows the inserted shape of the inserted shape detecting probe 1 as a guide.

Similarly to the above described manual operation, the insertion portion 11A is inserted inside the body cavity of the subject, e.g. from the anus 51 of the subject (see FIG. 31) to the rectum 52 while the inserted shape detecting probe 1 is placed inside the treatment instrument insertion channel 15. After the distal end portion of the inserted shape detecting probe 1 is made to protrude from the most distal end portion of the insertion portion 11A, the balloon 31 is expanded according to a predetermined procedure.

Figure 31:
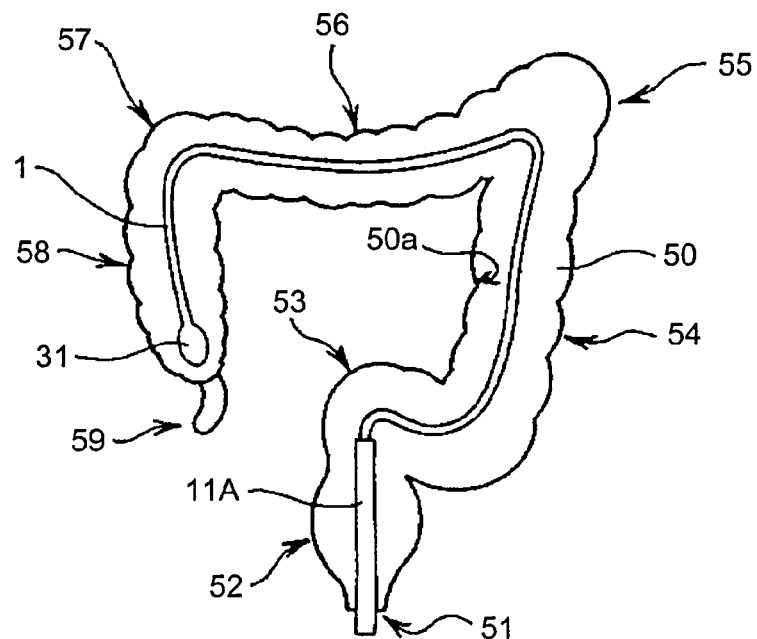
FIG. 31 illustrates another operation of the modification of the first embodiment of the present invention, and shows the inserted shape detecting probe and the insertion portion of the endoscope both inserted inside the large intestine and the intestinal canal thereof.
Figure 32:
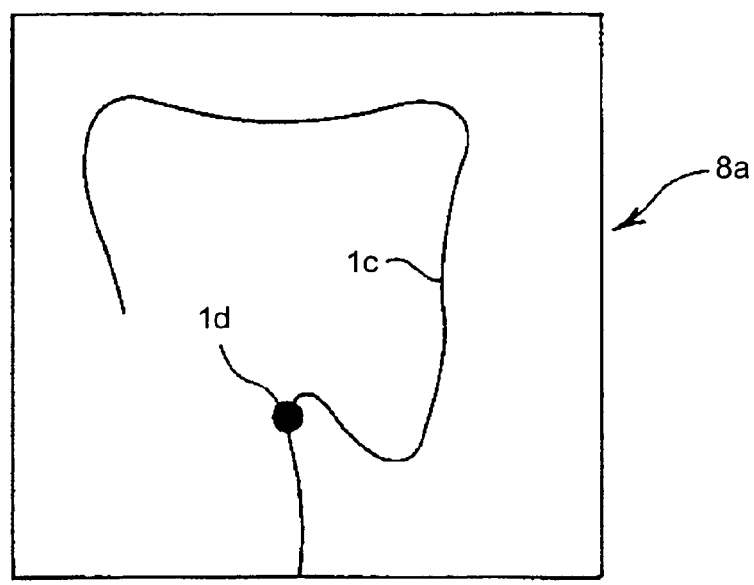
FIG. 32 illustrates how the inserted shape of the inserted shape detecting probe is displayed on the display screen of the monitor of the inserted shape detecting apparatus when the inserted shape detecting probe is at a position shown in FIG. 31.

Then, only the inserted shape detecting probe 1 is pushed inside from the treatment instrument insertion opening 14 side and made to advance. The expanded balloon 31 is attached to the distal end portion of the probe 1. The balloon 31 of the inserted shape detecting probe 1 advances smoothly through the rectum 52, the sigmoid colon 53, the descending colon 54, the splenic flexure 55, the transverse colon 56, the hepatic flexure 57, and the ascending colon 58, until eventually reaches the position next to the appendix 59. The state at this point is shown in FIG. 31. An image as shown in FIG. 32 is displayed on the display screen 8a of the monitor 8 at this point. Here, it can be seen that the inserted shape detecting probe 1 is arranged inside the intestinal canal 50 as shown by reference character 1c of FIG. 32, and that the distal end portion of the insertion portion 11A is arranged at a position denoted by reference character 1d inside the rectum 52.

While the inserted shape detecting probe 1 is arranged as described above, the insertion of the insertion portion 11A starts. The operator inserts the insertion portion 11A along the inserted shape detecting probe 1 as a guide. Since the operator can refer to the inserted shape of the inserted shape detecting probe 1 as displayed on the display screen 8a (see FIG. 32) of the monitor 8, the operator can insert the insertion portion 11A easily and smoothly up to a desired position inside the body cavity.

Figure 33:
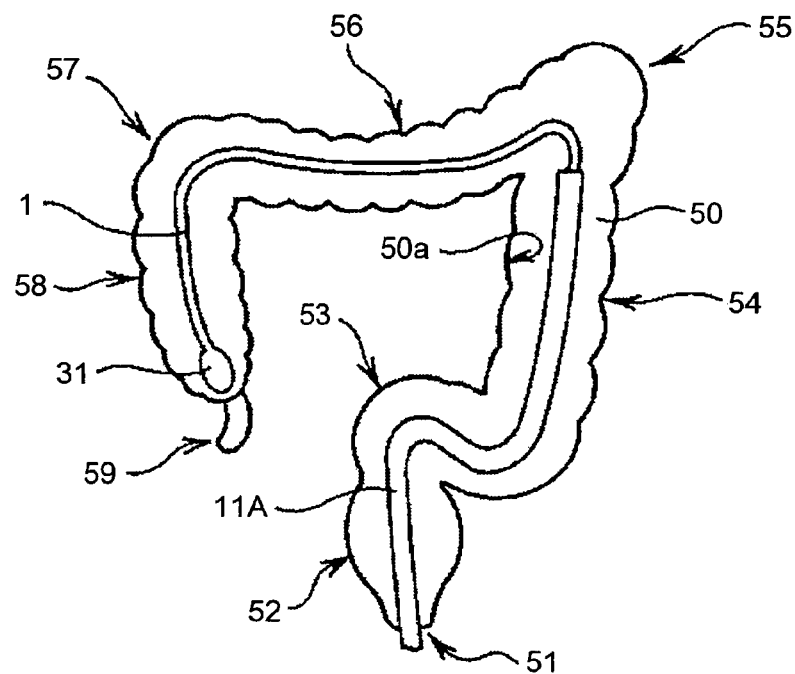
FIG. 33 illustrates the another operation of the modification of the first embodiment of the present invention, and shows the inserted shape detecting probe and the insertion portion of the endoscope both inserted inside the large intestine and the intestinal canal thereof.
Figure 34:
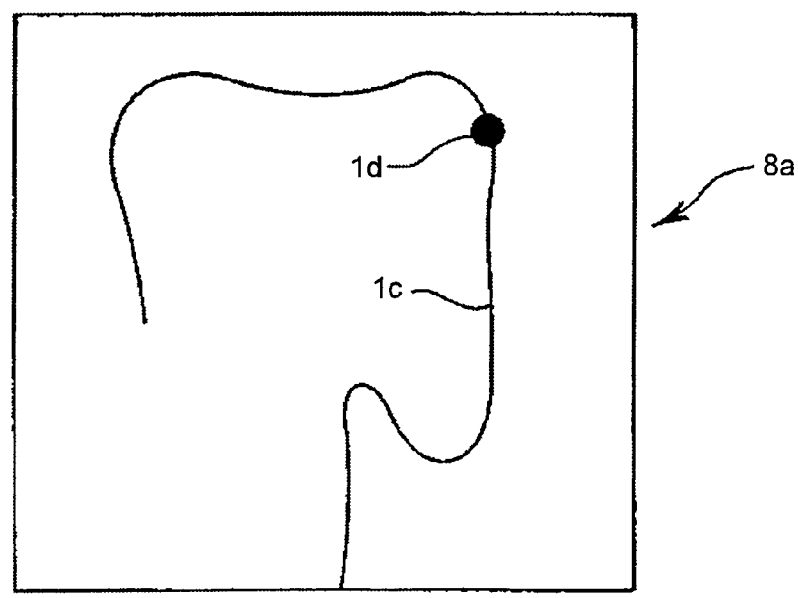
FIG. 34 illustrates how the inserted shape of the inserted shape detecting probe is displayed on the display screen of the monitor of the inserted shape detecting apparatus when the inserted shape detecting probe is at a position shown in FIG. 33.
Figure 35:
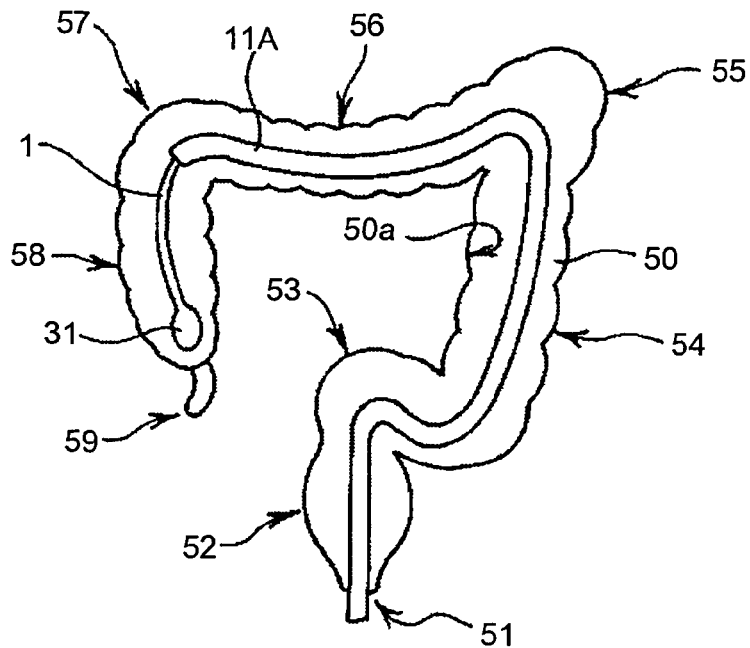
FIG. 35 illustrates the another operation of the modification of the first embodiment of the present invention, and shows the inserted shape detecting probe and the insertion portion of the endoscope both inserted inside the large intestine and the intestinal canal thereof.
Figure 36:
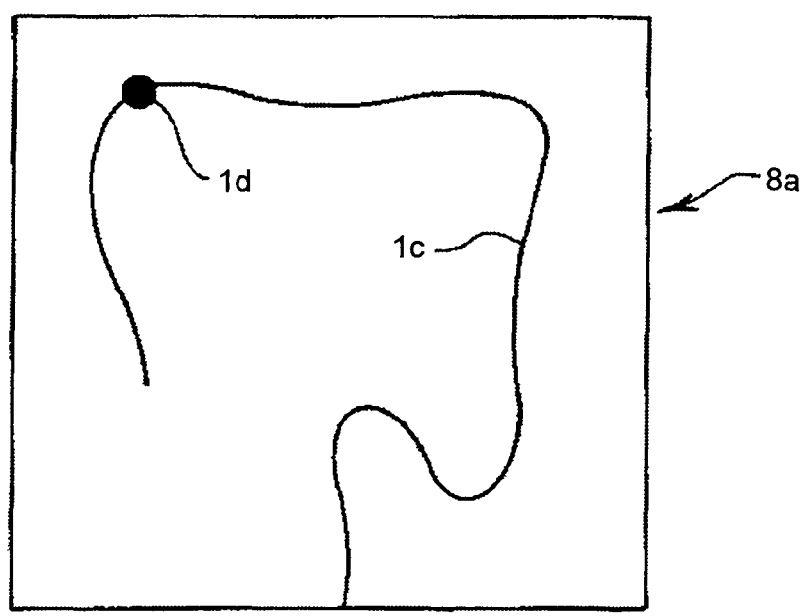
FIG. 36 illustrates how the inserted shape of the inserted shape detecting probe is displayed on the display screen of the monitor of the inserted shape detecting apparatus when the inserted shape detecting probe is at a position shown in FIG. 35.
Figure 37:
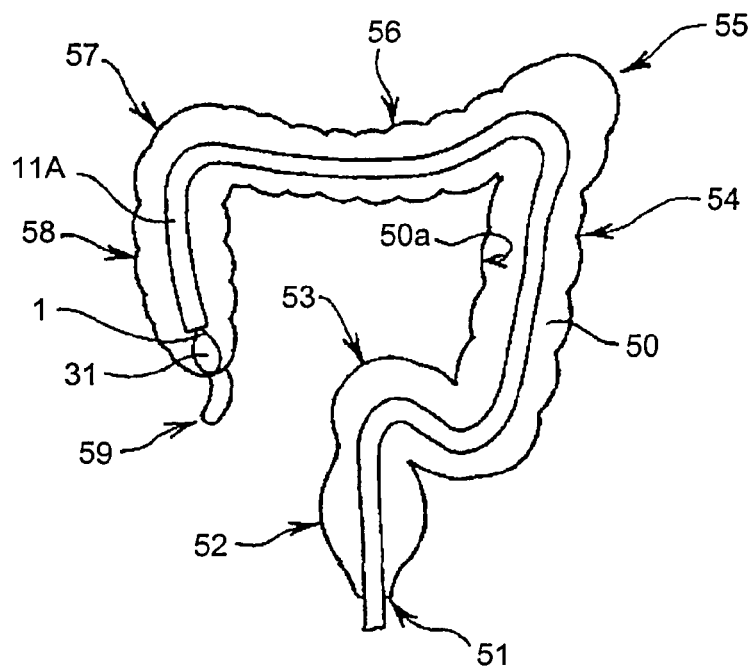
FIG. 37 illustrates the another operation of the modification of the first embodiment of the present invention, and shows the inserted shape detecting probe and the insertion portion of the endoscope both inserted inside the large intestine and the intestinal canal thereof.
Figure 38:
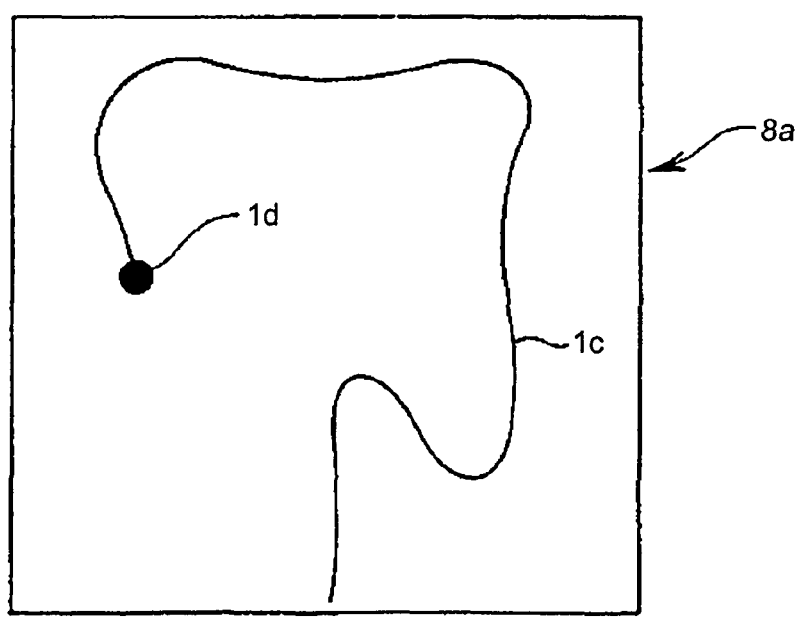
FIG. 38 illustrates how the inserted shape of the inserted shape detecting probe is displayed on the display screen of the monitor of the inserted shape detecting apparatus when the inserted shape detecting probe is at a position shown in FIG. 37.

FIG. 33 shows the state where the distal end portion of the insertion portion 11A moves from the descending colon 54 up to the splenic flexure 55. FIG. 34 shows an image displayed on the display screen 8a of the monitor 8 corresponding to the state shown in FIG. 33. FIG. 35 shows the state where the distal end portion of the insertion portion 11A moves from the transverse colon 56 through the hepatic flexure 57, up to the ascending colon 58. FIG. 36 shows an image displayed on the display screen 8a of the monitor 8 corresponding to the state shown in FIG. 35. FIG. 37 shows a state where the distal end portion of the insertion portion 11A reaches the appendix 59. FIG. 38 shows an image displayed on the display screen 8a of the monitor 8 corresponding to the state shown in FIG. 37.

Thus, the inserted shape detecting probe 1 and the insertion portion 11A are arranged at a desired position inside the body cavity, e.g., the position next to the appendix 59 as described above. In this state, the balloon 31 is turned into the contracted state (see FIG. 3) through the similar procedure as described above. Then the inserted shape detecting probe 1 is pulled inside the treatment instrument insertion channel 15. Thus, the preparation is completed for the observation and examination with the insertion portion 11A of the endoscope 3.

As described above, according to the modification of the first embodiment, the same advantages as those obtained in the first embodiment can be obtained. In addition, the inserted shape detecting apparatus system can be realized in which; the endoscope insertion portion has the distal end portion position detecting unit 45 for detection of the position of the distal end portion of the insertion portion 11A; the position of the distal end portion of the insertion portion 11A is displayed on the monitor 8 along with the inserted shape of the inserted shape detecting probe 1; and the operator can safely and securely insert and advance the insertion portion 11A of the endoscope 3 inside the intestinal canal 50 inside the body cavity while referring to the display screen 8a.

According to the first embodiment described above, the balloon 31 is provided at the distal end portion of the inserted shape detecting probe 1 as the endoscope insertion assistant probe, so that the inserted shape detecting probe 1 can be smoothly inserted inside the intestinal canal at the time of insertion. The structure of the distal end portion of the inserted shape detecting probe 1, however, is not limited to the structure with the balloon 31 as in the first embodiment. Various alternative structures are conceivable. Some of the alternative structures according to other embodiments will be described below.

Figure 39:
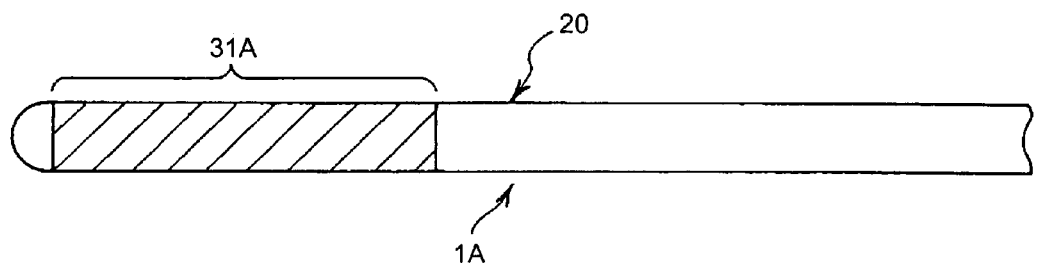
FIG. 39 is an enlarged view of a relevant portion, in particular, a distal end portion of an endoscope insertion assistant probe (inserted shape detecting probe) according to a second embodiment of the present invention.
Figure 40:
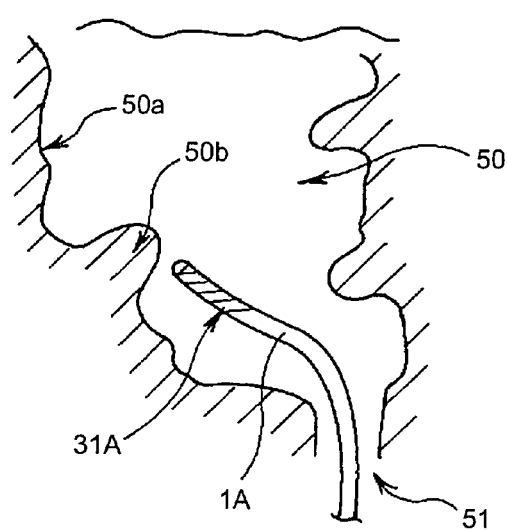
FIG. 40 shows the endoscope insertion assistant probe (inserted shape detecting probe) of FIG. 39 inserted inside the intestinal canal.

FIG. 39 is an enlarged view of a distal end portion of an endoscope insertion assistant probe (inserted shape detecting probe) according to a second embodiment of the present invention. FIG. 40 shows a state of the endoscope insertion assistant probe (inserted shape detecting probe) of FIG. 39 as inserted inside the intestinal canal.

An inserted shape detecting probe 1A which is the endoscope insertion assistant probe of the second embodiment is structured by removing the balloon 31 from the inserted shape detecting probe 1 of the first embodiment. The same elements as those of the first embodiment will not be described again, and different elements alone will be described below.

In the inserted shape detecting probe 1A of the second embodiment, a hydrophilic lubricant coating 31A is applied to a predetermined area of an outer surface of the outer sheath 20, which is provided at the distal end portion, for surface smoothing and improvement in insertability. Thus, the distal end portion of the inserted shape detecting probe 1A functions as the distal end guiding element.

Further, since the probe 1A does not include the balloon 31 of the first embodiment, the probe 1A naturally does not include the plural through holes 1a in the distal end portion of the probe 1. In other respects, the structure of the probe 1A is the same as the structure of the probe 1 of the first embodiment.

Since the hydrophilic lubricant coating 31A is applied to the distal end portion of the inserted shape detecting probe 1A of the second embodiment, the distal end portion easily passes over a bulge 50b or the like of the intestine wall 50a and is not caught in the unevenness of the intestine wall 50a. Therefore, when the inserted shape detecting probe 1A is inserted inside the intestinal canal 50 as shown in FIG. 40, the probe 1A can always advance smoothly.

In the second embodiment, the hydrophilic lubricant coating 31A is applied only in the predetermined area of the distal end portion of the inserted shape detecting probe 1A. The second embodiment, however, is not limiting, and the hydrophilic lubricant coating may be applied to the entire surface of the inserted shape detecting probe as shown in FIG. 41.

Figure 41:
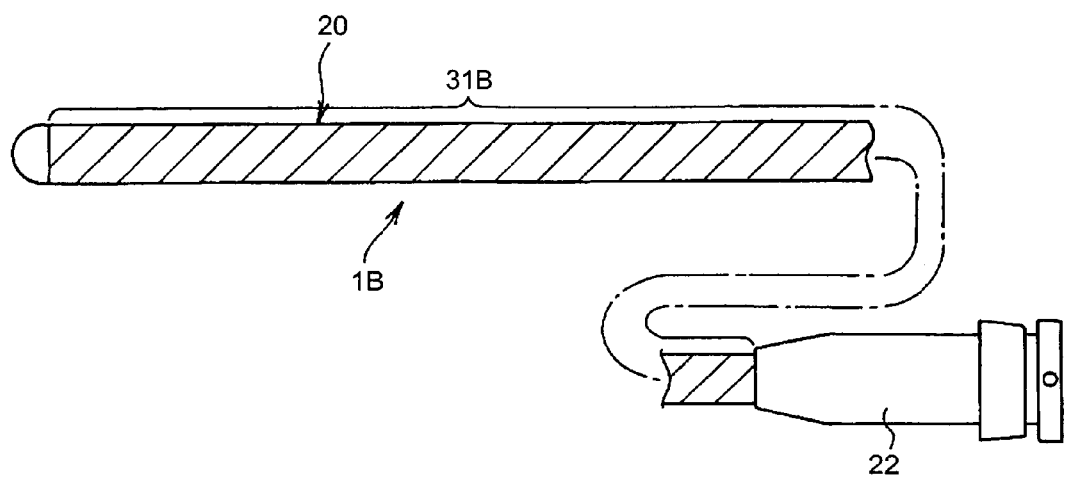
FIG. 41 is an enlarged view of a relevant portion, in particular, a distal end portion and a proximal end portion of an endoscope insertion assistant probe (inserted shape detecting probe) according to one modification of the second embodiment of the present invention.

FIG. 41 shows one modification of the second embodiment of the present invention, and is an enlarged view which primarily shows relevant portions, i.e., the distal end portion and a proximal end portion of an endoscope insertion assistant probe (inserted shape detecting probe).

In an inserted shape detecting probe 1B of the modification, a hydrophilic lubricant coating 31B is applied to an outer surface of the outer sheath 20 from the distal end portion to the connector portion 22 provided in the proximal end portion. Thus, the distal end portion of the inserted shape detecting probe 1B serves as the distal end guiding element. In other respect, the structure of the modification is the same as the structure of the second embodiment.

The modification having the above described structure has the same advantage as that of the second embodiment.

Further, the hydrophilic lubricant coating of the second embodiment may be applied to the outer surface of the balloon 31 of the first embodiment. The hydrophilic lubricant coating, in addition to the substantially spherical shape of the balloon 31, contributes to a further improvement in insertability.

In the second embodiment and the modification thereof described above, the hydrophilic lubricant coating 31A or 31B is applied directly to the outer surface of the outer sheath 20 of the inserted shape detecting probe 1A or 1B. The manner of coating is not limited thereto, and the coating can be applied in a manner as shown in FIG. 42 or FIG. 43.

Figure 42:
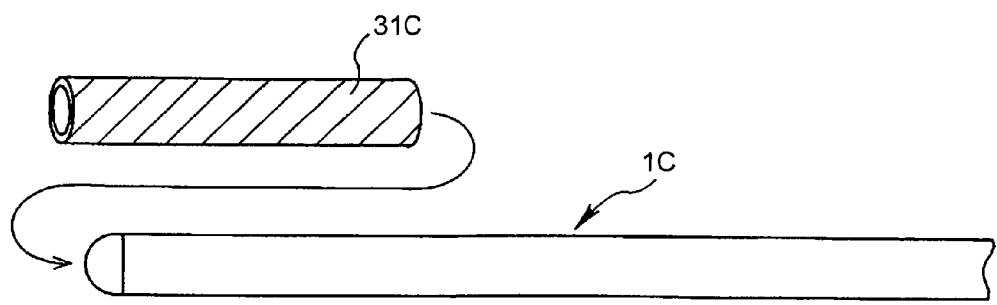
FIG. 42 is an exploded view which separately shows a distal end portion and a cover member attached to the distal end portion of an endoscope insertion assistant probe (inserted shape detecting probe) according to a third embodiment of the present invention.
Figure 43:
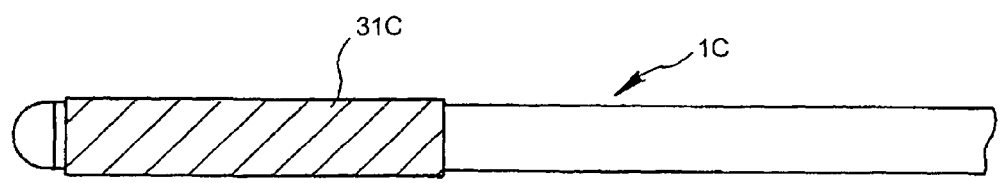
FIG. 43 is an enlarged view of a relevant portion of the endoscope insertion assistant probe (inserted shape detecting probe) of FIG. 42 with the cover member attached to the distal end portion.

FIGS. 42 and 43 are enlarged views of the distal end portion of the endoscope insertion assistant probe (inserted shape detecting probe) of a third embodiment of the present invention. FIG. 42 is an exploded view which shows the distal end portion of the inserted shape detecting probe of the third embodiment and the cover member attached to the distal end portion separately. FIG. 43 is a schematic drawing of the inserted shape detecting probe having the cover member attached to the distal end portion.

An inserted shape detecting probe 1C of the third embodiment includes a cover member 31C that is detachably attached to the distal end portion and covers a predetermined area of the distal end portion. The cover member 31C is made of a thin-film member, and is a tube member which has a substantially cylindrical shape so as to cover the outer surface of the inserted shape detecting probe 1C. A hydrophilic lubricant coating is applied on the outer surface of the cover member 31C. Thus, the distal end portion of the inserted shape detecting probe 1C serves as the distal end guiding element. The probe itself is a general, conventional, inserted shape detecting probe. In other respects, the structure is substantially the same as that of the second embodiment.

The third embodiment with the above-described structure has the same advantage as that of the second embodiment. Further, since the cover member 31C provided to the distal end portion of the inserted shape detecting probe 1C of the third embodiment is detachable, the insertability of the probe 1C itself can be readily improved simply by the attachment of the cover member 31C on the distal end portion of the general, conventional, inserted shape detecting probe. Further, the cover member 31C can be replaced with a new one every time the probe 1C is used. When the cover member 31C is manufactured as a disposable member, a process, such as a process of cleaning the cover member 31C can be simplified.

Figure 44:
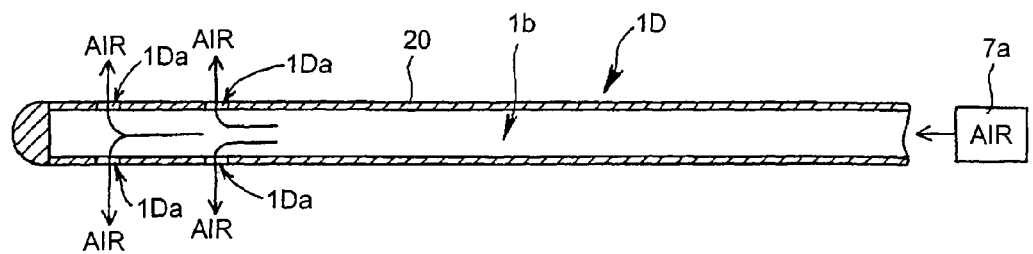
FIG. 44 is a schematic enlarged sectional view of a distal end portion of an endoscope insertion assistant probe (inserted shape detecting probe) according to a fourth embodiment of the present invention.
Figure 45:
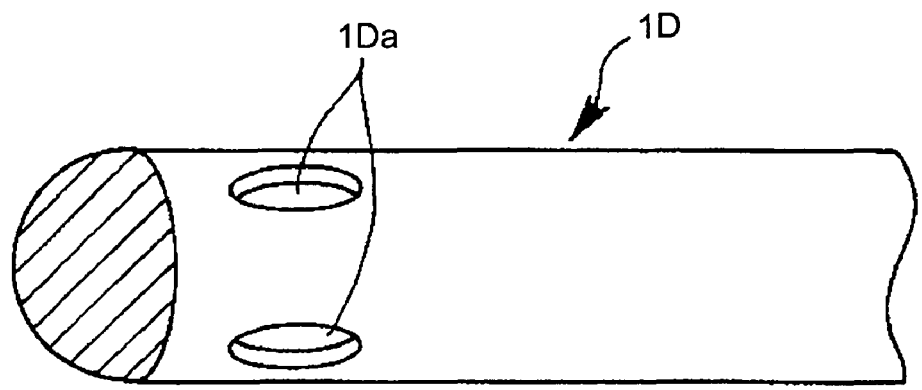
FIG. 45 is an enlarged perspective view of a relevant portion, in particular, the distal end portion of the endoscope insertion assistant probe (inserted shape detecting probe) of FIG. 44.
Figure 46:
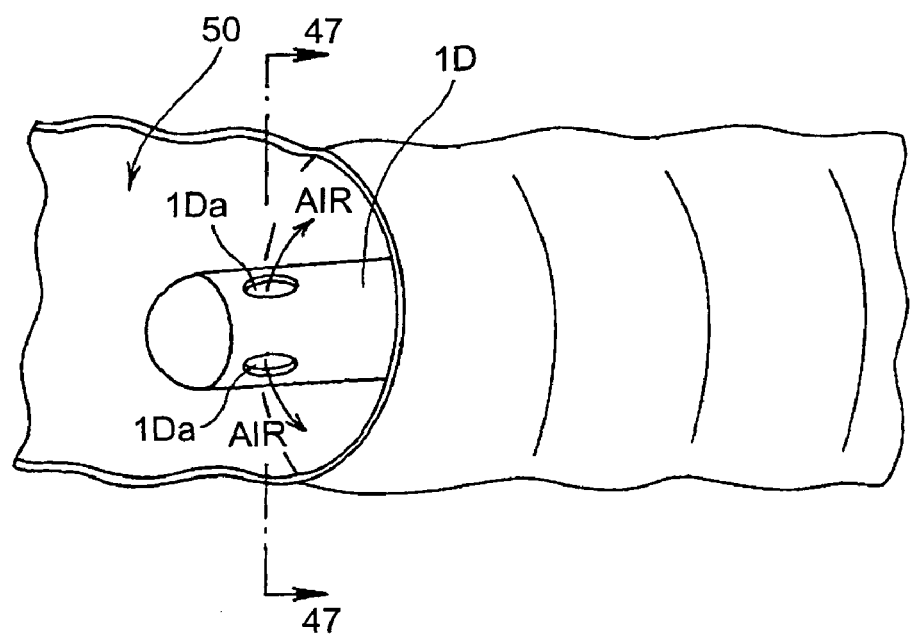
FIG. 46 is a perspective view which shows the endoscope insertion assistant probe (inserted shape detecting probe) of FIG. 44 as inserted inside the intestinal canal.
Figure 47:
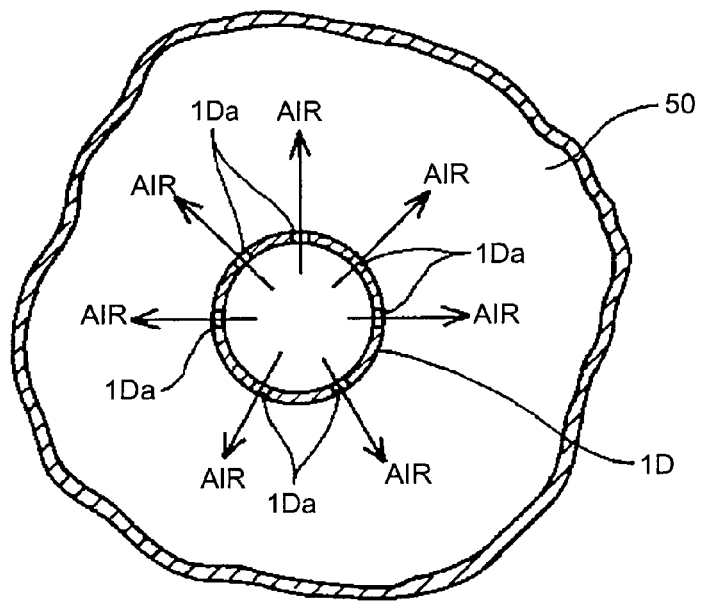
FIG. 47 is a sectional view along line 47-47 of FIG. 46.

FIGS. 44 to 47 show a fourth embodiment of the present invention. Specifically, FIGS. 44 and 45 are enlarged views of a distal end portion of an endoscope insertion assistant probe (inserted shape detecting probe) of the fourth embodiment. More specifically, FIG. 44 is a schematic sectional view of the distal end portion of the inserted shape detecting probe. FIG. 45 is an enlarged perspective view of a relevant portion, in particular, the distal end portion of the inserted shape detecting probe. FIGS. 46 and 47 show a state of the inserted shape detecting probe of the fourth embodiment inserted inside the intestinal canal. Specifically, FIG. 46 is a perspective view and FIG. 47 is a sectional view along line 47-47 of FIG. 46.

The structure of the fourth embodiment is substantially the same as the structure of the first embodiment. The fourth embodiment is different from the first embodiment in that the fourth embodiment does not include the balloon 31 included in the first embodiment. The elements which are common between the fourth embodiment and the first embodiment will be denoted by the same reference characters and the description thereof will not be repeated. Different structural features alone will be described below.

An inserted shape detecting probe 1D, which is the endoscope insertion assistant probe of the fourth embodiment, includes plural through holes 1Da at predetermined positions in the vicinity of the distal end portion thereof as shown in FIGS. 44 and 45. The through holes 1Da are similar to those in the inserted shape detecting probe 1 (see FIG. 3) of the first embodiment and serve as fluid ejecting openings. Between the inner wall surface of the outer sheath 20 and the source coils or the like (not shown; see 21 of FIG. 3) of the inserted shape detecting probe 1D, a slight gap 1b (briefly shown for convenience' sake) is formed. The gap 1b penetrates the inserted shape detecting probe 1D from the distal end portion to the connector portion (not shown; see 22 of FIG. 2) in the proximal end portion.

Similarly to the first embodiment, the inserted shape detecting apparatus 7 (see FIG. 1) is connected to the inserted shape detecting probe 1D through the connector portion 22. The inserted shape detecting apparatus 7 has the pump 7a which delivers a fluid, i.e., gas or liquid, inside the inserted shape detecting probe 1D, the drive controlling circuit for the pump 7a, and the like.

When the inserted shape detecting apparatus 7 drive controls the pump 7a, the fluid, i.e., gas or liquid, is delivered inside the inserted shape detecting probe 1D from the side of the pump 7a through the connector portion 22. The fluid passes through the gap 1b of the inserted shape detecting probe 1D to reach the distal end portion of the inserted shape detecting probe 1D, and eventually is discharged from the plural through holes 1Da. Thus, the inserted shape detecting probe 1D is always held at a position away from the intestine wall 50a, and the smooth advancement of the inserted shape detecting probe 1D inside the intestinal canal 50 can be realized. Thus, the distal end portion of the inserted shape detecting probe 1D serves as the distal end guiding element.

An operation of the insertion of the inserted shape detecting probe 1D of the fourth embodiment inside the body cavity is performed as described below. First, through a predetermined procedure, for example, through the manual operation (see FIGS. 6 to 12 and the description thereof) described in relation to the first embodiment, the inserted shape detecting probe 1D of the fourth embodiment is inserted inside the body cavity (inside the intestinal canal 50) of the subject.

After the inserted shape detecting probe 1D is inserted inside the intestinal canal 50, the inserted shape detecting apparatus 7 drive controls the pump 7a to start the delivery of the fluid, i.e., gas or liquid, inside the inserted shape detecting probe 1D. Then, the fluid passes through the gap 1b of the inserted shape detecting probe 1D and is discharged from the plural through holes 1Da provided at the distal end portion. At this time, the fluid is discharged from the through holes 1Da in a direction towards the intestine wall 50a of the intestinal canal 50 as shown by an arrow, to which the term "AIR" is affixed, in FIGS. 46 and 47. Thus, the inserted shape detecting probe 1D is always kept at a position away from the intestine wall 50a, and advances inside the intestinal canal 50 smoothly.

The fourth embodiment described above has the same advantage as that of the first embodiment. In addition, since the inserted shape detecting probe 1D, after inserted inside the intestinal canal 50, is kept away from the intestine wall 50a by the fluid discharged from the through holes 1Da, the inserted shape detecting probe 1D can advance smoothly along the curved shape of the intestinal canal 50 without causing damages to the intestine wall 50a.

A cover member like the cover member of the third embodiment may be additionally be provided in the inserted shape detecting probe 1D of the fourth embodiment.

Figure 48:
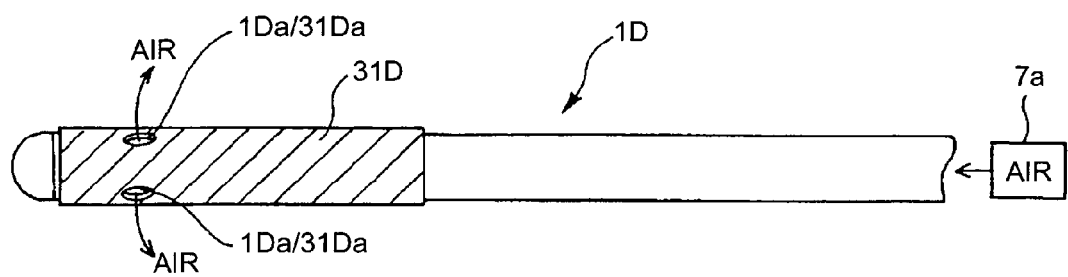
FIG. 48 is an enlarged view of a relevant portion, in particular, a distal end portion of an endoscope insertion assistant probe (inserted shape detecting probe) according to a modification of the fourth embodiment of the present invention.

FIG. 48 is an enlarged view of a distal end portion of an inserted shape detecting probe according to a modification of the fourth embodiment.

The inserted shape detecting probe 1D of the modification of the fourth embodiment has a cover member 31D made from a thin-film member at the distal end portion. The cover member 31D is detachably attached to the distal end portion of the probe 1D as described in relation to the third embodiment above. A hydrophilic lubricant coating is applied on an outer surface of the cover member 31D. Through holes 31Da are formed in the cover member 31D at positions corresponding to the positions of the through holes 1Da of the inserted shape detecting probe 1D, so that through holes 1Da and 31Da face with each other when the cover member 31D is attached to the distal end portion of the inserted shape detecting probe 1D. The through holes 31Da serve as fluid ejecting openings similarly to the through holes 1Da. In other respect, structure of the modification of the fourth embodiment is the same as that of the fourth embodiment.

Since the inserted shape detecting probe 1D of the modification with the above described structure is provided with the detachable cover member 31D at the distal end portion thereof, and the hydrophilic lubricant coating is applied to the outer surface of the cover member 31D, the insertability can be further improved.

In the modification of the fourth embodiment, the cover member 31D with hydrophilic lubricant coating on the outer surface is provided. The manner of coating application is not limited thereto. For example, the hydrophilic lubricant coating may be directly applied to a predetermined area of the outer surface of the distal end portion of the outer sheath of the inserted shape detecting probe; or to the entire outer surface extending from the distal end portion to the proximal end portion of the outer sheath.

An endoscope insertion assistant probe of a fifth embodiment of the present invention will be described below with reference to FIG. 49.

Figure 49:
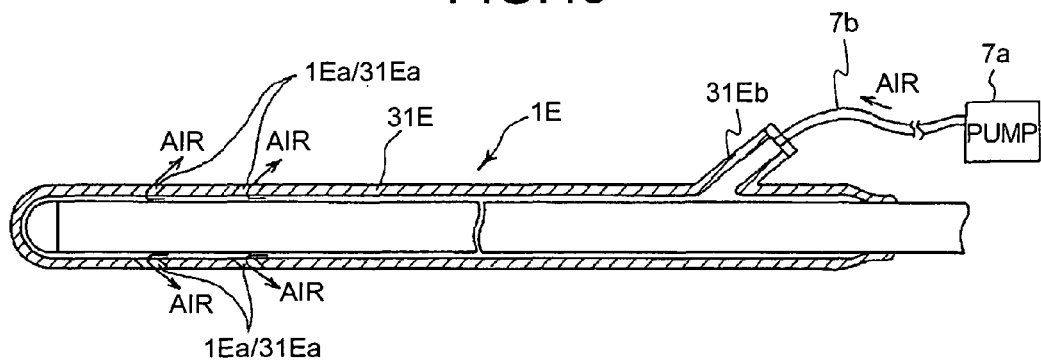
FIG. 49 is an enlarged view of a relevant portion, in particular, a portion of an endoscope insertion assistant probe (inserted shape detecting probe) according to a fifth embodiment of the present invention.

FIG. 49 is an enlarged view of a relevant portion, in particular, a part of the endoscope insertion assistant probe (inserted shape detecting probe) according to the fifth embodiment of the present invention.

The structure of the fifth embodiment is substantially the same as the structure of the fourth embodiment. A difference lies in the shape of the through holes formed at the distal end portion of the inserted shape detecting probe and that an additional fluid passage is provided for discharge of the fluid from the distal end portion. The elements common between the fourth embodiment and the fifth embodiment will be denoted by the same reference characters, and the description thereof will not be repeated. Different elements alone will be described below.

A main body of an inserted shape detecting probe 1E, which is the endoscope insertion assistant probe of the fifth embodiment, includes a general, conventional, existing inserted shape detecting probe as shown in the third embodiment, and a cover member 31E which covers the entire surface of the inserted shape detecting probe from the distal end portion up to the proximal end portion and is fixed thereto.

The cover member 31E is arranged so as to cover the outer surface of the probe main body from the distal end portion up to the proximal end portion as described above. Here, a gap is formed between the outer surface of the probe main body and an inner surface of the cover member 31E, so that the fluid can flow smoothly therethrough. The gap runs form the distal end portion to the vicinity of the proximal end portion of the inserted shape detecting probe 1E.

Further, an opening 31Eb is formed at a predetermined position near the proximal end portion of the cover member 31E. The opening 31Eb is inclined backward forming a sharp angle with an axial direction of the probe main body. A tube 7b, through which the fluid is supplied from the pump 7a of the inserted shape detecting apparatus 7, is connected to the opening 31Eb. The inserted shape detecting apparatus 7 can drive control the pump 7a. For example, the inserted shape detecting apparatus 7 can control the increase and the decrease of a volume of the supplied fluid.

Plural through holes 1Ea are formed in the vicinity of the distal end portion of the cover member 31E. The through hole 1Ea opens in an inclined direction towards the proximal end side of the probe main body with respect to the axial direction of the probe main body. In other words, the through hole 1Ea opens backwards forming a sharp angle with the axial direction of the probe main body.

The fluid is supplied according to the drive control of the pump 7a of the inserted shape detecting apparatus 7, passes through the tube 7b, and the gap formed by the cover member 31E, reaches the distal end portion of the inserted shape detecting probe 1E, and is finally discharged from the through holes 1Ea.

Here, the through holes 1Ea are formed so as to be oriented backward forming a sharp angle as described above. Hence, the fluid discharged from the through holes 1Ea is directed backward from the distal end portion of the inserted shape detecting probe 1E. The force exerted by the discharge of the fluid serves as propulsion to make the inserted shape detecting probe 1E advance. In addition, when the increase or the decrease in the amount of the supplied fluid is controlled through the drive control of the pump 7a by the inserted shape detecting apparatus 7, for example, the discharged amount of the fluid from the through holes 1Ea is also adjusted. Accordingly, a travel distance of the inserted shape detecting probe 1E can be adjusted. Thus, the distal end portion of the inserted shape detecting probe 1E serves as the distal end guiding element. In other respect, the structure of the fifth embodiment is substantially the same as the structure of the fourth embodiment.

The fifth embodiment with the above-described structure has the same advantage as that of the fourth embodiment. In addition, since the fifth embodiment has a separate fluid passage, the flow rate of the fluid can be more surely adjusted, and the discharged amount of the fluid from the through holes 1Ea can be adjusted accordingly. Thus, the travel distance of the inserted shape detecting probe 1E and the like can be surely controlled.

Further, since the through hole 1Ea is inclined backward forming a sharp angle, so that the fluid discharged from the through hole 1Ea is directed backward, the force exerted by the discharge of the fluid can be utilized as propulsion for the inserted shape detecting probe 1E.

Further, when the hydrophilic lubricant coating is directly applied to the outer surface of the cover member 31E, or when a thin-film member whose outer surface is coated by the hydrophilic lubricant is additionally arranged in the fifth embodiment, the insertability can be further improved.

An endoscope insertion assistant probe of a sixth embodiment of the present invention will be described with reference to FIGS. 50 to 52.

Figure 50:
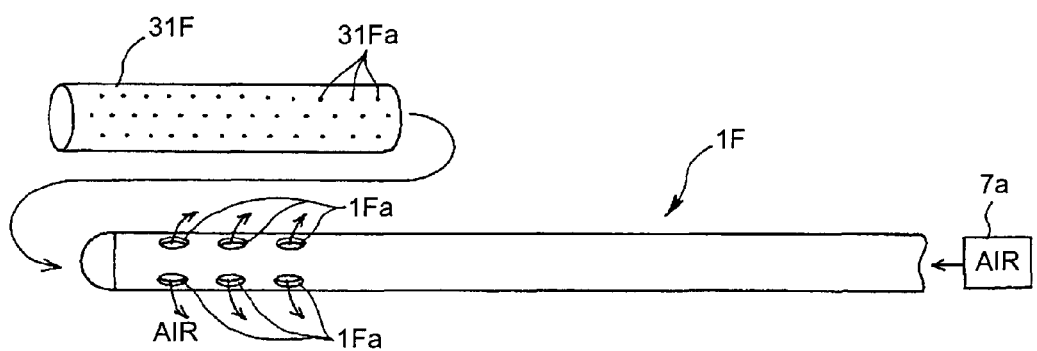
FIG. 50 is an exploded view which separately shows a distal end portion and a cover member attached to the distal end portion of an endoscope insertion assistant probe (inserted shape detecting probe) according to a sixth embodiment of the present invention.
Figure 51:
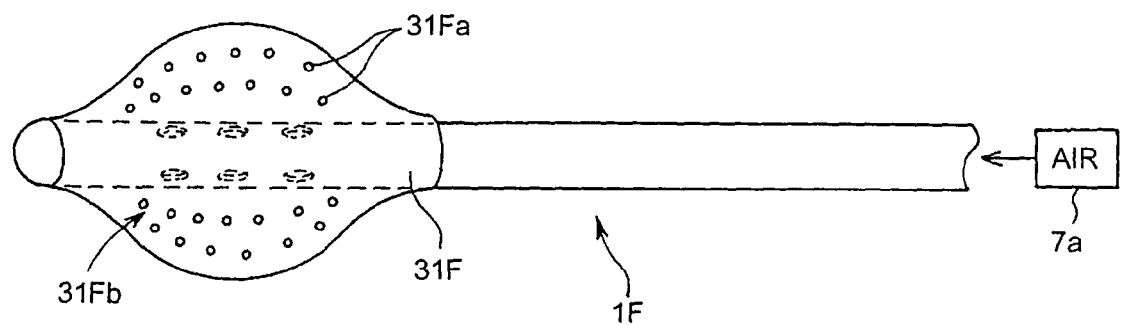
FIG. 51 is a schematic view of the endoscope insertion assistant probe (inserted shape detecting probe) of FIG. 50 with the cover member attached to the distal end portion.
Figure 52:
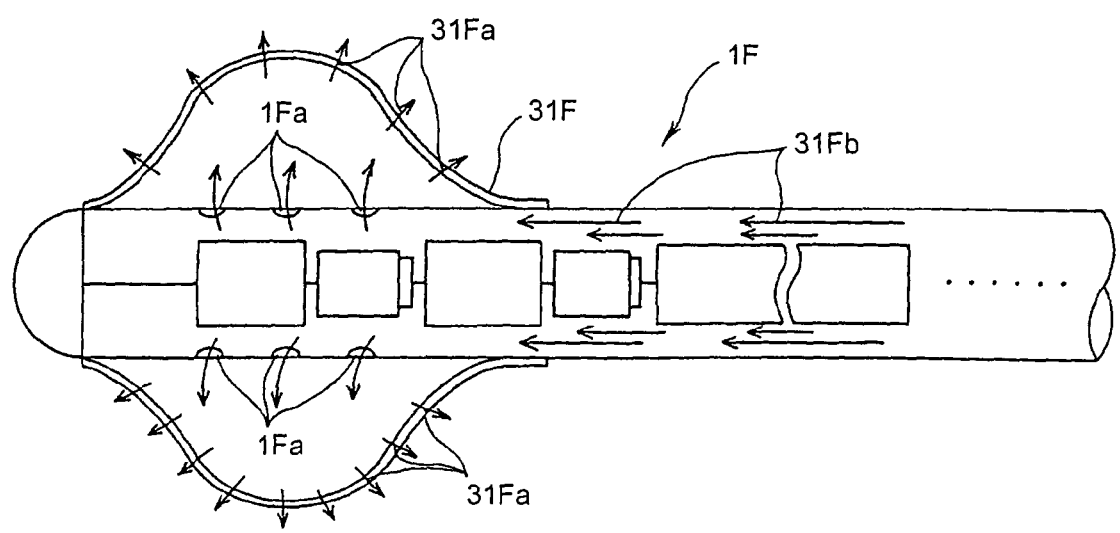
FIG. 52 is a conceptual view illustrating a function of a fluid flowing inside the endoscope insertion assistant probe (inserted shape detecting probe) in the state of FIG. 51.

FIGS. 50 to 52 show the endoscope insertion assistant probe (inserted shape detecting probe) of the sixth embodiment of the present invention, and FIG. 50 is an exploded view which shows a distal end portion of the inserted shape detecting probe of the sixth embodiment and a cover member attached to the distal end portion separately. FIG. 51 is a schematic view showing the inserted shape detecting probe with the cover member attached to the distal end portion. FIG. 52 is a conceptual diagram showing a function of a fluid flowing inside the inserted shape detecting probe in the state of FIG. 51.

The structure of the sixth embodiment is substantially the same as the structure of the first embodiment. Difference lies in that the cover member is attached to the distal end portion of the inserted shape detecting probe in place of the balloon 31, and the fluid flowing inside the inserted shape detecting probe contains lubricant. The elements common between the sixth embodiment and the first embodiment will be denoted by the same reference characters, and the description thereof will not be repeated. Different elements alone will be described below.

As shown in FIG. 51, an inserted shape detecting probe 1F of the sixth embodiment has a cover member 31F which is detachably attached to a distal end portion thereof and covers a predetermined area. The cover member 31F is made of a flexible, expandable, thin-film-like, elastic member, and is formed in a substantially cylindrical shape so as to cover the outer surface of the inserted shape detecting probe 1F. Further, the cover member 31F has plural minute holes 31Fa. When the cover member 31F is in a contracted state (i.e., state shown in FIG. 50), the plural minute holes 31Fa are maintained in a closed state; whereas when the cover member 31F is in an expanded state (i.e., state shown in FIGS. 51 and 52), the plural minute holes 31Fa are in an open state.

The plural through holes 1Fa are formed in the vicinity of the distal end portion of the inserted shape detecting probe 1F. Fluid 31Fb passes inside the inserted shape detecting probe 1F to reach the distal end portion and is discharged through the through holes 1Fa.

Inside the inserted shape detecting probe 1F, a passage for the fluid 31Fb is formed with the gap 1b and runs from the distal end portion up to the connector portion (not shown) of the proximal end portion of the inserted shape detecting probe 1F. The passage communicates to the pump 7a (see FIGS. 50 and 51) of the inserted shape detecting apparatus 7 (see FIG. 1).

When the pump 7a of the inserted shape detecting apparatus 7 is drive controlled, the fluid 31Fa, i.e., gas or liquid, is delivered from the side of the pump 7a toward inside the inserted shape detecting probe 1F. The fluid 31Fb passes through the gap 1b (passage) to reach the distal end portion of the inserted shape detecting probe 1F, and is eventually discharged from the plural through holes 1Fa. The fluid 31Fb discharged from the through holes 1Fa serves to expand the cover member 31F. Accordingly, the cover member 31F is turned from the contracted state of FIG. 50 into a substantially spherical shape shown in FIGS. 51 and 52. Here, when the cover member 31F is in the contracted state shown in FIG. 50, the plural minute holes 31Fa are in the closed state; whereas when the cover member 31F is turned into the substantially spherical shape as shown in FIGS. 51 and 52, the plural minute holes 31Fa become open. When the cover member 31F is in the expanded state, the cover member 31F is filled with the fluid 31Fb inside. The fluid 31Fb gradually seeps out from the plural minute holes 31Fa and covers the outer surface of the cover member 31F.

The fluid 31Fb contains a lubricant having lubricity in addition to a predetermined gas or a predetermined liquid. The lubricant contained in the fluid 31Fb seeps out from the plural minute holes 31Fa of the cover member 31F filled with the fluid 31Fb. The lubricant contained in the fluid 31Fb covers the outer surface of the cover member 31F and contributes to the improvement of the insertability of the inserted shape detecting probe 1F inside the intestinal canal. Thus, the distal end portion of the inserted shape detecting probe 1F serves as the distal end guiding element.

On the other hand, when the fluid inside the inserted shape detecting probe 1F is sucked out to the side of the pump 7a through the drive control of the pump 7a of the inserted shape detecting apparatus 7, the cover member 31F is turned into the contracted state. In other respects, the structure of the sixth embodiment is substantially the same as the structure of the first embodiment.

The sixth embodiment having the above described structure has the same advantage as that of the first embodiment. Further, according to the sixth embodiment, the cover member 31F has the plural minute holes 31Fa, and the fluid 31Fb contains lubricant. Therefore, through the drive control of the pump 7a of the inserted shape detecting apparatus 7, the fluid 31Fb is discharged from the through holes 1Fa provided at the distal end portion of the inserted shape detecting probe 1F, thereby expanding the cover member 31F. Along with the expansion of the cover member 31F, the fluid 31Fb containing the lubricant seeps out from the plural minute holes 31Fa. The seeping lubricant covers the outer surface of the cover member 31F, thereby making the outer surface a smooth surface. Thus, the insertability of the inserted shape detecting probe 1F inside the intestinal canal can be further improved.

An endoscope insertion assistant probe according to a seventh embodiment of the present invention will be described below with reference to FIGS. 53 to 55.

Figure 53:
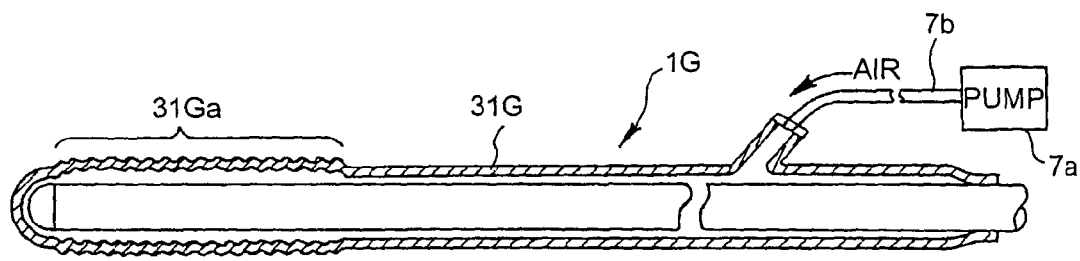
FIG. 53 is an enlarged view of a relevant portion, in particular, a portion of an endoscope insertion assistant probe (inserted shape detecting probe) according to a seventh embodiment of the present invention in a normal state.
Figure 54:
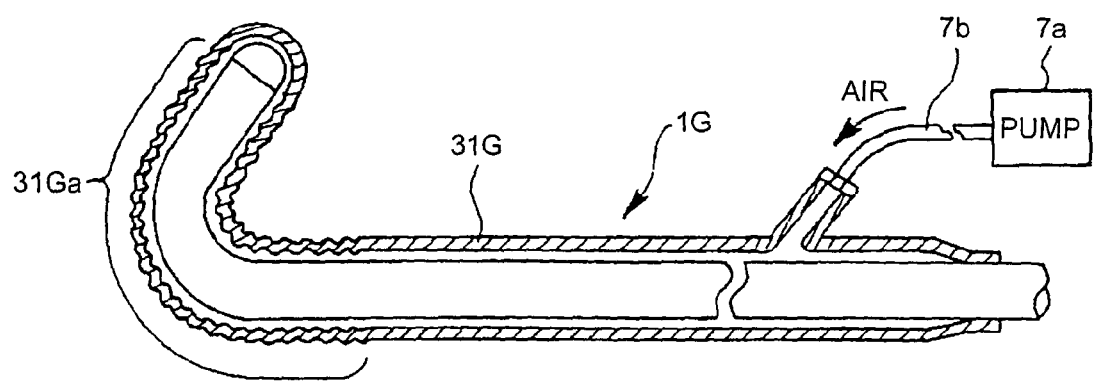
FIG. 54 is an enlarged view of a relevant portion, in particular, a distal end portion of the inserted shape detecting probe of FIG. 53 in a bent state.
Figure 55:
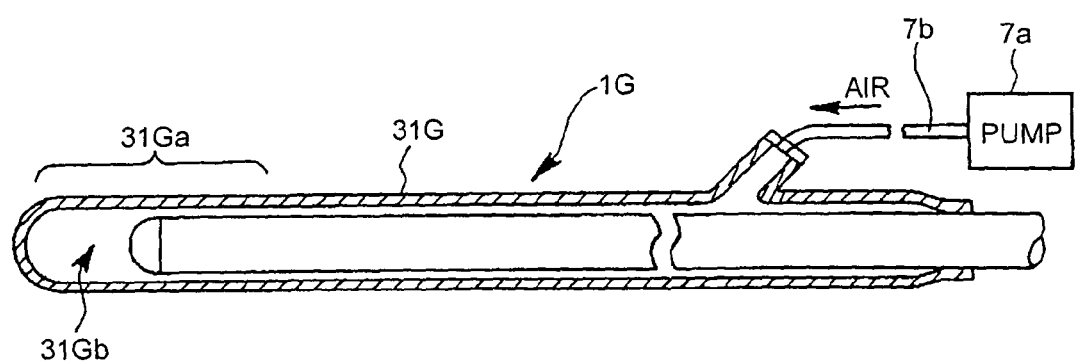
FIG. 55 is an enlarged view of a relevant portion, in particular, the distal end portion of the inserted shape detecting probe of FIG. 53 in an extended state.

FIGS. 53 to 55 each show a part of the endoscope insertion assistant probe (inserted shape detecting probe) according to the seventh embodiment of the present invention. FIG. 53 shows a normal state of the inserted shape detecting probe of the seventh embodiment. FIG. 54 shows the inserted shape detecting probe of the seventh embodiment with a distal end portion in a bent state. FIG. 55 shows the inserted shape detecting probe of the seventh embodiment with the distal end portion in an extended state. FIGS. 53 to 55 are enlarged views of relevant portions.

The structure of the seventh embodiment is substantially the same as the structure of the fifth embodiment. Difference lies in that the cover member does not have the through holes, and instead, the cover member has an accordion-folded portion which is formed in the vicinity of the distal end portion and stretchable. Here, the elements common between the seventh embodiment and the fifth embodiment will be denoted by the same reference characters, and the description thereof will not be repeated. Different elements alone will be described below.

As shown in FIGS. 53 to 55, an inserted shape detecting probe 1G of the seventh embodiment includes, for example, a general, conventional, existing inserted shape detecting probe, and a cover member 31G which is fixed to the inserted shape detecting probe and covers the entire probe from the distal end portion up to the proximal end portion thereof.

The cover member 31G, similarly to the cover member of the fifth embodiment, is arranged so as to cover the outer surface of the probe main body from the distal end portion up to the proximal end portion. Here, a gap is formed between an outer surface of the probe main body and an inner surface of the cover member 31G, so that the fluid can flow smoothly therethrough. The gap runs continuously from the distal end portion up to the vicinity of the proximal end portion of the inserted shape detecting probe 1G.

The cover member 31G itself is made of a flexible material. In addition, an accordion-folded portion 31Ga is formed in the vicinity of the distal end portion of the inserted shape detecting probe 1G. Hence, the inserted shape detecting probe 1G can bend flexibly and can be deformed following small curves inside the intestinal canal.

The fluid supplied by the drive control of the pump 7a of the inserted shape detecting apparatus 7 passes through the tube 7b and the gap formed by the cover member 31G and reaches the distal end portion 31Gb of the inserted shape detecting probe 1G, to extend the accordion-folded portion 31Ga. On the other hand, when the fluid inside the gap of the cover member 31G is sucked to the side of the pump 7a by the drive control of the pump 7a of the inserted shape detecting apparatus 7, the accordion-folded portion 31Ga of the cover member 31G shrinks and recovers an original accordion-like shape. In other respects, the structure of the seventh embodiment is the same as the structure of the fifth embodiment.

According to the seventh embodiment having the above-described structure, the probe main body is covered with the cover member 31G made of a flexible material, and the accordion-folded portion 31Ga is formed in the distal end portion, whereby a more flexible bending operation can be realized. Therefore, following capability of the probe for a small curved region, e.g., a region with a complicated shape such as the sigmoid colon, inside the intestinal canal 50 can be improved. The insertability of the inserted shape detecting probe 1G can be thus further improved. Thus, the distal end portion of the inserted shape detecting probe 1G serves as the distal end guiding element.

On the other hand, the accordion-folded portion 31Ga can be extended by the supply of fluid inside the cover member 31G. Then, the outer shape of the inserted shape detecting probe 1G can be made straight, and a predetermined degree of hardness can be granted to the inserted shape detecting probe 1G. Therefore, the insertability can be secured for deep regions and regions other than the curved region merely by deforming the accordion-folded portion 31Ga into the extended state.

An endoscope insertion assistant probe of an eighth embodiment of the present invention will be described below with reference to FIGS. 56 to 61.

Figure 56:
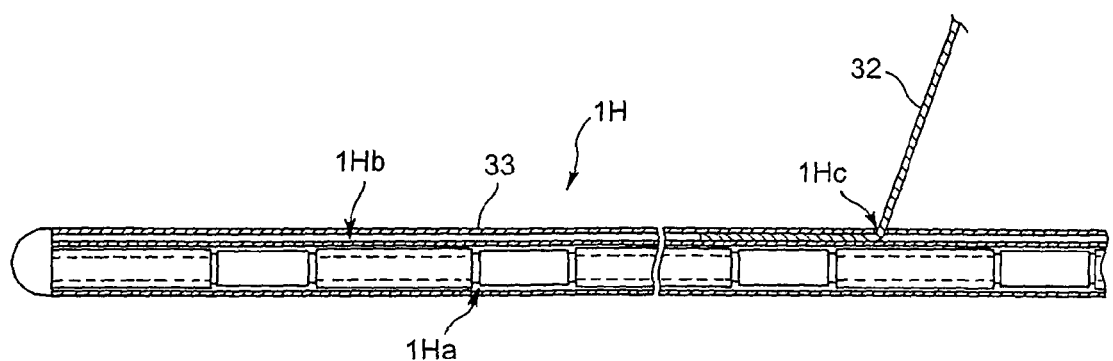
FIG. 56 is a sectional view of an endoscope insertion assistant probe (inserted shape detecting probe) according to an eighth embodiment of the present invention with a metal wire being pulled out.
Figure 57:
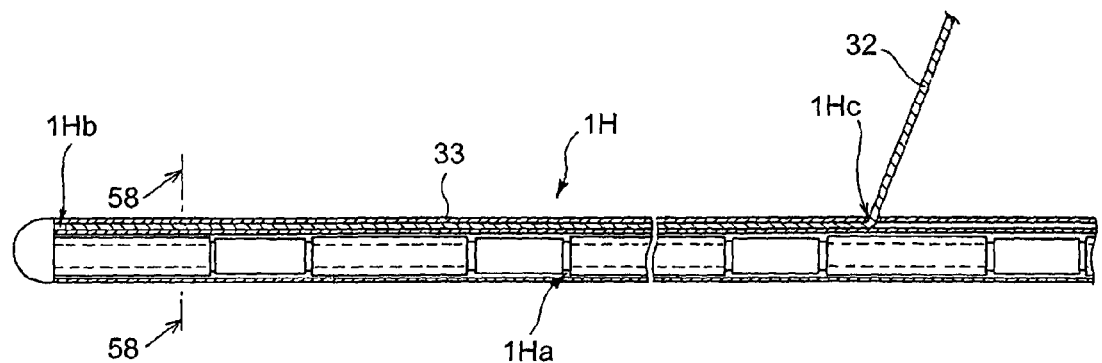
FIG. 57 is a sectional view of the endoscope insertion assistant probe (inserted shape detecting probe) of FIG. 56 with the metal wire penetrating the endoscope insertion assistant probe up to a distal end portion thereof.
Figure 58:
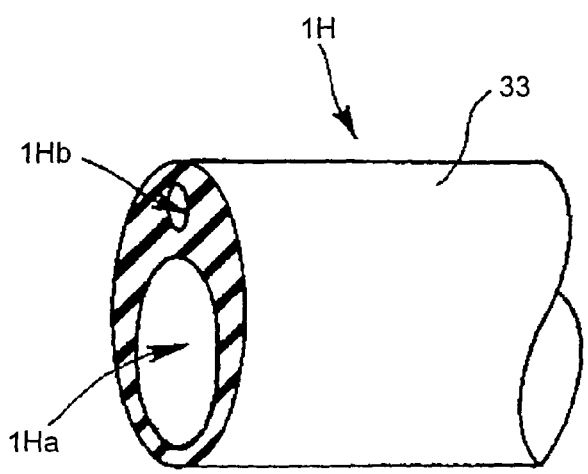
FIG. 58 is an enlarged perspective view of a relevant portion of the endoscope insertion assistant probe showing a section along line 58-58 of FIG. 57.
Figure 59:
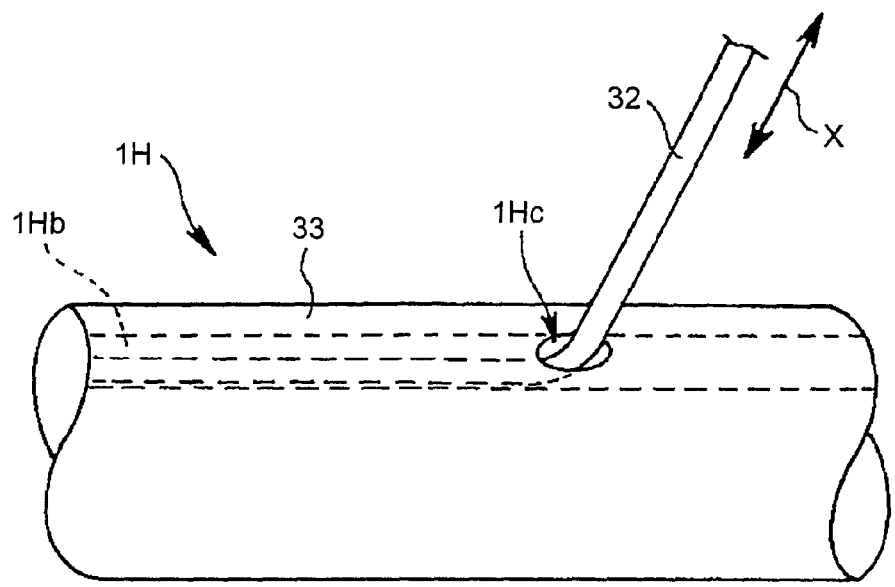
FIG. 59 is an enlarged view of a relevant portion, in particular, a portion around a metal wire insertion opening in the endoscope insertion assistant probe (inserted shape detecting probe) of FIG. 56.
Figure 60:
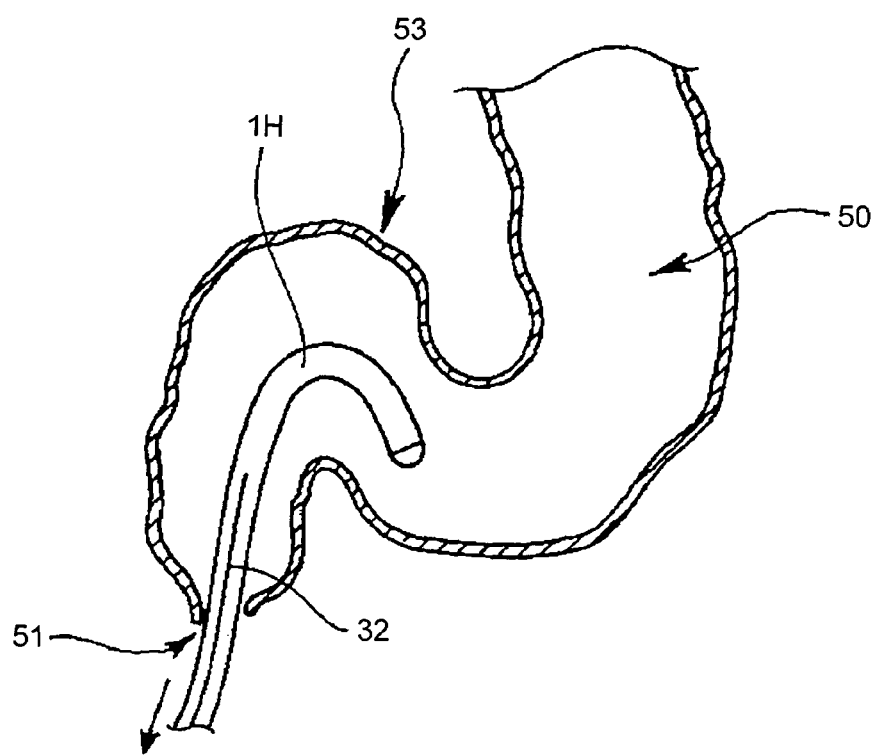
FIG. 60 shows the endoscope insertion assistant probe (inserted shape detecting probe) of FIG. 56 being inserted through a curved portion inside the body cavity.
Figure 61:
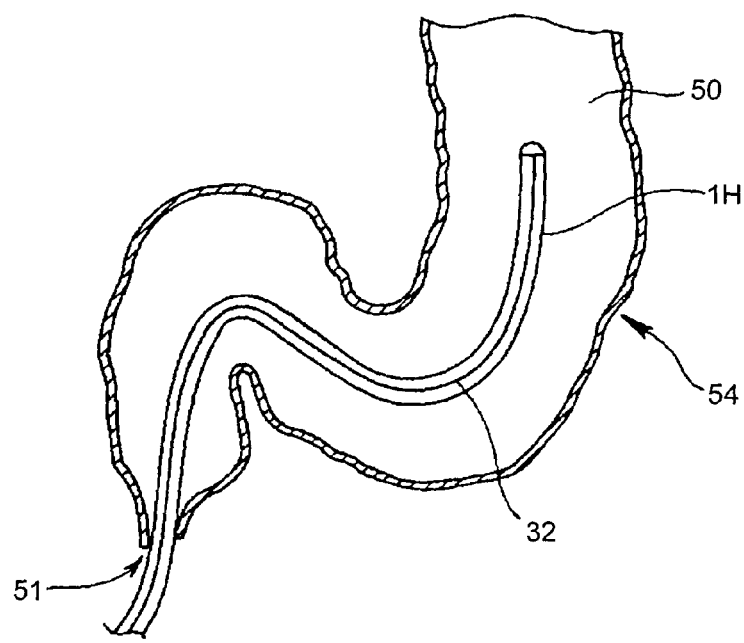
FIG. 61 shows the endoscope insertion assistant probe (inserted shape detecting probe) of FIG. 56 being inserted through a portion other than the curved portion inside the body cavity.

FIGS. 56 to 59 show a part of the endoscope insertion assistant probe (inserted shape detecting probe) according to the eighth embodiment of the present invention. Specifically, FIG. 56 is a sectional view of the endoscope insertion assistant probe (inserted shape detecting probe) according to the eighth embodiment from which a metal wire is pulled out. FIG. 57 is a sectional view of the endoscope insertion assistant probe (inserted shape detecting probe) in which the metal wire is inserted up to the distal end portion. FIG. 58 is an enlarged perspective view showing a relevant portion, in particular, a section along line 58-58 of FIG. 57. FIG. 59 is an enlarged view of a relevant portion, in particular, a portion around a metal wire insertion opening in the endoscope insertion assistant probe (inserted shape detecting probe) according to the eighth embodiment. FIGS. 60 and 61 illustrate an operation of the endoscope insertion assistant probe (inserted shape detecting probe) according to the eighth embodiment. In particular, FIG. 60 shows a state of the inserted shape detecting probe passing through a curved portion inside the body cavity. FIG. 61 shows a state of the inserted shape detecting probe passing through a portion other than the curved portion inside the body cavity.

A basic concept of the eighth embodiment is substantially the same as that of the seventh embodiment. A basic structure of the eighth embodiment is also substantially the same as the structure of each of the embodiments described above.

The basic concept of the eighth embodiment is: for the insertion of the endoscope insertion assistant probe (inserted shape detecting probe) inside the intestinal canal inside the body cavity, the distal end portion of the inserted shape detecting probe is structured so as to flexibly bend when passing through a curved portion of the intestinal canal on the one hand; and the distal end portion of the inserted shape detecting probe is structured so as to have a certain degree of hardness when passing through a portion other than the curved portion on the other hand, whereby the inserted shape detecting probe has a good insertability for any portion inside the intestinal canal. The elements common between the eighth embodiment and other embodiments described above are not shown nor described further, and different elements alone will be described below.

As shown in FIGS. 56 and 57, an inserted shape detecting probe 1H, which is the endoscope insertion assistant probe of the eighth embodiment, has plural lumens in the outer tube. In the eighth embodiment, a so-called multiple-lumen tube 33 made of flexible silicone or the like is employed.

The multiple-lumen tube 33 has a first lumen 1Ha and a second lumen 1Hb as shown in FIG. 58. In the first lumen 1Ha, various elements constituting the inserted shape detecting probe of each embodiment described above are arranged, whereas in the second lumen 1Hb, a metal wire (wire, hard wire) 32 having a predetermined hardness is inserted in an axially movable manner. The second lumen 1Hb penetrates the inserted shape detecting probe 1H from a vicinity of the distal end portion up to a vicinity of the proximal end portion. An opening 1Hc is formed at a predetermined position near the proximal end to allow an entrance of the metal wire 32 into the second lumen 1Hb as shown in FIG. 59. The metal wire 32 is inserted from the opening 1Hc inside the second lumen 1Hb, and moved forward and backward along a direction of an arrow X shown in FIG. 59. With the insertion and movement of the metal wire 32, the hardness of the inserted shape detecting probe 1H can be changed in a portion around the distal end portion. Thus, the distal end portion of the inserted shape detecting probe 1H serves as the distal end guiding element. The basic structure other than those specified above is substantially the same as the structure of other embodiments.

In the eighth embodiment having the above described structure, when the inserted shape detecting probe 1H is inserted inside the body cavity from the anus 51 as shown in FIG. 60 and comes to a curved portion inside the intestinal canal 50 inside the body cavity, for example, the sigmoid colon 53, the metal wire 32 is pulled out by a small amount from inside the second lumen 1Hb, so that the metal wire 32 is retreated from a portion near the distal end portion of the inserted shape detecting probe 1H. Then, the distal end portion of the inserted shape detecting probe 1H can be made flexible and easily bent, whereby a good insertability can be secured for the insertion into the curved portion. Adjusting the amount that the metal wire 32 is pulled out allows the hardness of the portion near the distal end portion of the probe 1H to be adjusted in any desired area.

On the other hand, in the portion other than the curved portion inside the intestinal canal 50 inside the body cavity as shown in FIG. 61, for example, at the portion inside the descending colon 54, the metal wire 32 is inserted up to the vicinity of the distal end portion of the second lumen 1Hb. Then, the distal end portion of the inserted shape detecting probe 1H comes to have a certain degree of hardness. Then, the probe 1H can maintain a good insertability for the portion other than the curved portion as well.

In the eighth embodiment described above, the multiple-lumen tube 33 which has two lumens is employed, and one metal wire 32 is inserted in a retractable manner. The above example is not limiting, however, and the outer tube may be structured to have lumens so that plural metal wires can be inserted. Then, the hardness of the distal end portion of the inserted shape detecting probe 1H can be easily and properly adjusted based on the number of employed metal wires.

Further, plural metal wires may be prepared, each having a different diameter and made from different material. Then the hardness of the distal end portion of the inserted shape detecting probe 1H can be adjusted with the use of various metal wires.

An endoscope insertion assistant probe according to an ninth embodiment of the present invention will be described below with reference to FIG. 62.

Figure 62:
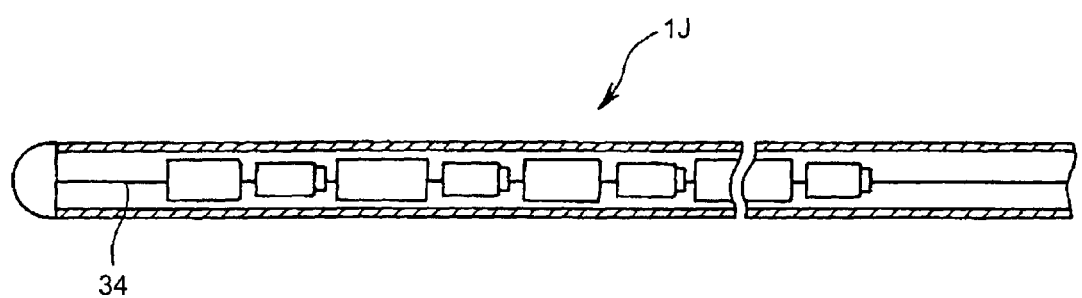
FIG. 62 is a schematic sectional view of an internal structure of a relevant portion, in particular, a portion near a distal end portion of an endoscope insertion assistant probe (inserted shape detecting probe) according to a ninth embodiment of the present invention.

FIG. 62 is a schematic sectional view of an internal structure of a relevant portion, in particular, a portion near the distal end portion of the endoscope insertion assistant probe (inserted shape detecting probe) according to the ninth embodiment of the present invention.

The structure of the ninth embodiment is substantially the same as the structure of the eighth embodiment. In the eighth embodiment, the metal wire 32 is inserted into the second lumen 1Hb of the multiple-lumen tube 33 as a hardness adjuster for the portion near the distal end portion of the inserted shape detecting probe 1H (see FIG. 56, for example). In the ninth embodiment, in place of the metal wire 32, a core (see 23 in FIG. 2 of the first embodiment) made of a shape-memory material is employed in a general inserted shape detecting probe as shown in FIG. 62. The elements common between the ninth embodiment and the eighth embodiment will be denoted by the same reference characters and the description thereof will not be repeated. Different elements alone will be described below.

A basic structure of an inserted shape detecting probe 1J of the ninth embodiment is the same as the structure of the general, conventional, inserted shape detecting probe as shown in FIG. 60. Specifically, the inserted shape detecting probe 1J primarily includes, inside the outer sheath, plural coil units for generation of a magnetic field, a signal line connected to the coil unit, and a core 34 to which the coil unit is securely fixed.

Here, the core 34 of the inserted shape detecting probe 1J is made of a shape memory material which remembers a straight line shape, for example. When the inserted shape detecting probe 1J is inserted inside the body cavity, the distal end portion of the probe 1J is made to flexibly bend to pass through a curved portion when passing through the curved portion such as the region of the sigmoid colon inside the intestinal canal. On the other hand, when the inserted shape detecting probe 1J passes through a portion such as the descending colon other than the curved portion, heat or an electric signal is applied to the core 34, so that the core 34 returns easily to its remembered state (here, straight line state). Thus, the distal end portion of the inserted shape detecting probe 1J serves as the distal end guiding element. The basic structure other than those specified above is substantially the same as that of the seventh embodiment.

The ninth embodiment having the above described structure has the same advantage as that of the eighth embodiment. Further, since a desired effect can be obtained simply by the use of the shape memory material for the core 34 in the inserted shape detecting probe 1J, the probe 1J can be readily manufactured without need of changes to an existing production facility. Thus, the ninth embodiment readily contributes to an improvement in productivity and reduction in manufacturing cost.

In the ninth embodiment described above, the core is made of the shape memory material. The ninth embodiment, however, is not limiting. For example, the outer sheath may be made of a material in which shape memory material is dispersed. One of such modification will be described below with reference to FIG. 63.

Figure 63:
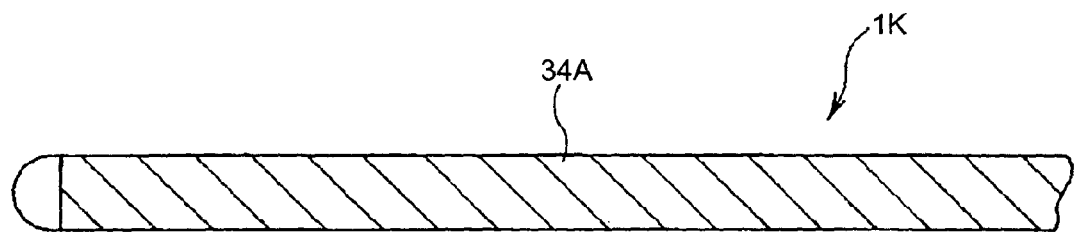
FIG. 63 is a schematic sectional view of an internal structure of a relevant portion, in particular, a portion near a distal end portion of an endoscope insertion assistant probe (inserted shape detecting probe) according to a modification of the ninth embodiment of the present invention.

FIG. 63 is a schematic sectional view of an internal structure of a relevant portion, in particular, a portion near the distal end portion of an endoscope insertion assistant probe (inserted shape detecting probe) according to one modification of the ninth embodiment of the present invention.

A basic structure of an inserted shape detecting probe 1K of the modification is the same as the structure of the inserted shape detecting probe 1J of the ninth embodiment. The core 34 of the inserted shape detecting probe 1J, however, is replaced with a core of, for example, a general, conventional, inserted shape detecting probe.

In the inserted shape detecting probe 1K of the modification, an outer sheath 34A is made of a material containing a shape memory material dispersed. Thus, the distal end portion of the inserted shape detecting probe 1K serves as the distal end guiding element. The basic structure other than those specified above is substantially the same as the structure of the ninth embodiment.

The modification of the ninth embodiment having the above described structure has the same advantage as that of the ninth embodiment.

An endoscope insertion assistant probe according to a tenth embodiment of the present invention will be described below with reference to FIG. 64.

Figure 64:
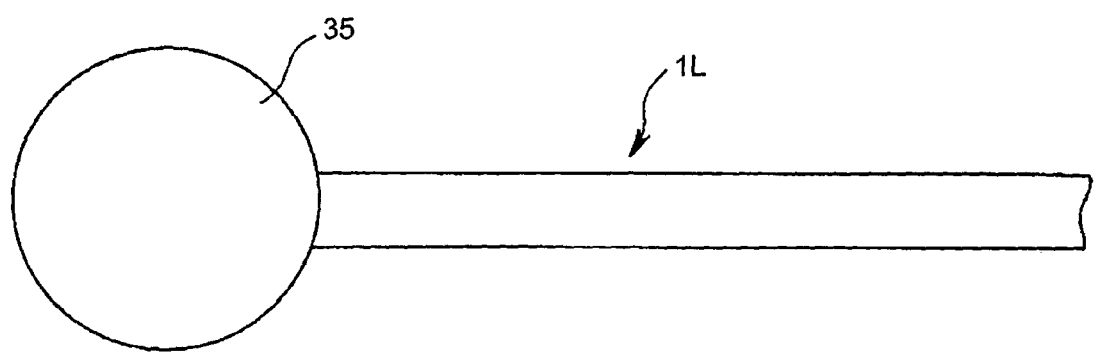
FIG. 64 is an enlarged view of a relevant portion, in particular, a distal end portion of an endoscope insertion assistant probe (inserted shape detecting probe) according to a tenth embodiment of the present invention.

FIG. 64 is an enlarged view of a relevant portion, in particular, a distal end portion of the endoscope insertion assistant probe (inserted shape detecting probe) according to the tenth embodiment of the present invention.

A basic structure of the tenth embodiment is substantially the same as that of the second embodiment. Difference lies in that a spherical member is securely fixed to the distal end portion of the endoscope insertion assistant probe (inserted shape detecting probe). The elements common between the tenth embodiment and the second embodiment will not be described again, and different elements alone will be described below.

As shown in FIG. 64, an inserted shape detecting probe 1L of the tenth embodiment includes a solid spherical member 35 securely attached to the distal end portion thereof as the distal end guiding element. The spherical member 35 has a high surface slidability and is light in weight. The spherical member 35 is made of a material such as Teflon®, Duracon®, polysulfone, and polyphenylsulfone. When a highly transparent material is employed, for example, when acryl, silicone, or the like is employed, the spherical member 35 does not interfere with a visual field of an observation screen when the endoscope (3; see FIG. 1) is used. A diameter of the spherical member 35 is set to be larger than a diameter of the probe main body, for example, the diameter of the spherical member 35 is set approximately 10 to 30 mm ($\phi$=10 to 30 mm), or desirably approximately 10 to 20 mm ($\phi$=10 to 20 mm). The spherical member 35 may be oval rather than a perfect circle as shown in FIG. 64. Alternatively, the distal end guiding element may have a balloon shape as shown in FIG. 4, a shape like a circular cone with a rounded apex, or the like.

The distal end portion of the probe main body is buried into the spherical member 35. Note that the hydrophilic lubricant coating 31A applied on the outer surface of the outer sheath 20 in the inserted shape detecting probe 1A of the second embodiment is not applied to the inserted shape detecting probe 1L of the tenth embodiment. In other respects, the structure of the tenth embodiment is the same as that of the first embodiment.

Since the inserted shape detecting probe 1L of the tenth embodiment includes the spherical member 35 arranged in the distal end portion, the spherical member 35 passes over the unevenness or the like of the intestine wall and moves smoothly without being caught by the uneven portion when the inserted shape detecting probe 1L is inserted into the intestinal canal inside the body cavity.

Figure 65:
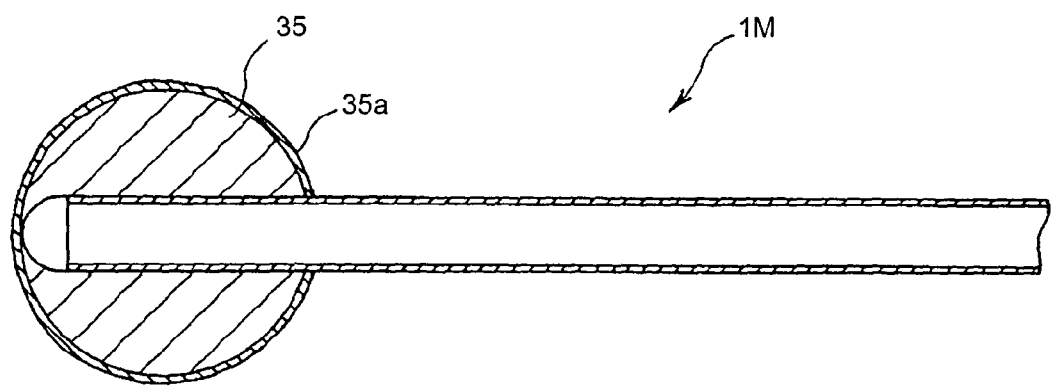
FIG. 65 is an enlarged sectional view of a relevant portion, in particular, a distal end portion of an endoscope insertion assistant probe (inserted shape detecting probe) according to a modification of the tenth embodiment of the present invention.

In the tenth embodiment, a hydrophilic lubricant coating 35a may be applied to an entire outer surface of the spherical member 35 arranged at the distal end portion of the inserted shape detecting probe 1L. For example, as in a modification of FIG. 65, the hydrophilic lubricant coating 35a may be applied to the entire outer surface of the spherical member 35 which is the distal end guiding element that is securely fixed to the distal end portion of an inserted shape detecting probe 1M. When the probe is structured as described above, the hydrophilic lubricant coating 35a can further contribute to facilitate the insertion.

A surface treatment applied to the outer surface of the spherical member 35 is not limited to the hydrophilic lubricant coating 35a of the above modification. For example, the spherical member 35 may be structured so that the lubricant seeps out from inside in a similar manner to the sixth embodiment.

Figure 66:
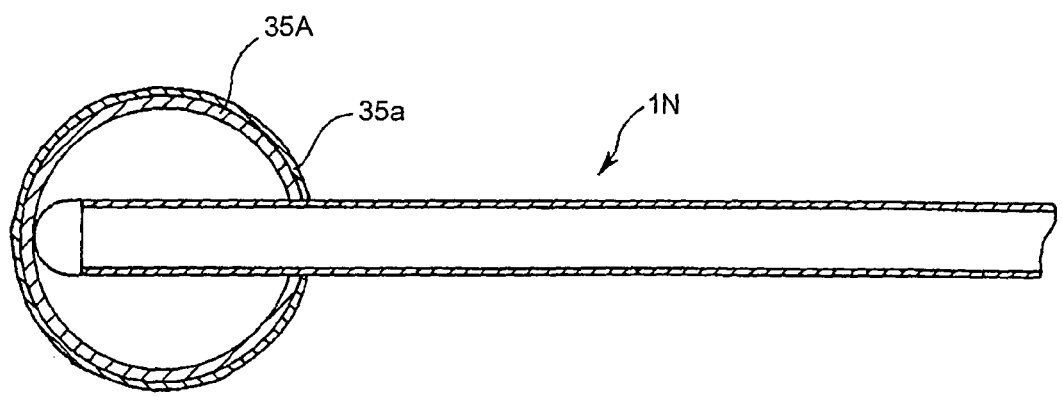
FIG. 66 is an enlarged sectional view of a relevant portion, in particular, a distal end portion of an endoscope insertion assistant probe (inserted shape detecting probe) according to another modification of the tenth embodiment of the present invention.

Alternatively, a hollow spherical member 35A may be provided in place of the solid spherical member 35 as shown as another modification in FIG. 66. The spherical member 35A is the distal end guiding element securely fixed to the distal end portion of an inserted shape detecting probe 1N similarly to the first modification above, and the hydrophilic lubricant coating 35a is applied on the entire outer surface of the solid spherical member 35A. When the probe is structured as described above, the weight of the spherical member 35A is reduced. Thus, the insertability can be readily improved.

An endoscope insertion assistant probe according to an eleventh embodiment of the present invention will be described below with reference to FIGS. 67 and 68.

Figure 67:
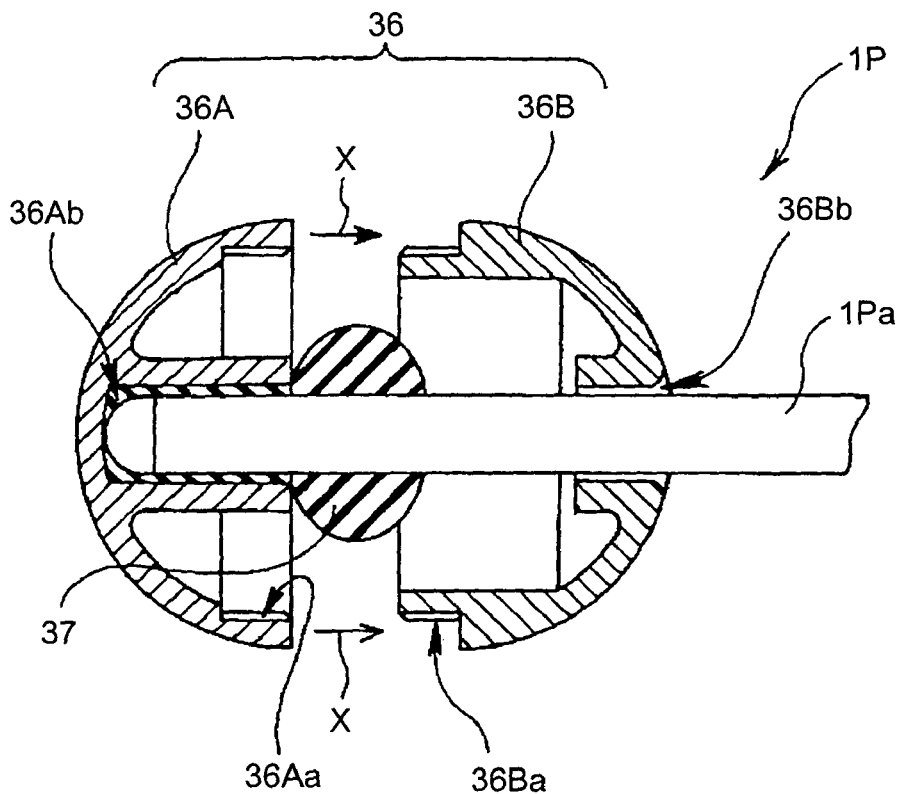
FIG. 67 is a sectional view which shows a spherical member fixed to a distal end portion of an endoscope insertion assistant probe (inserted shape detecting probe) according to an eleventh embodiment of the present invention in a disassembled state.
Figure 68:
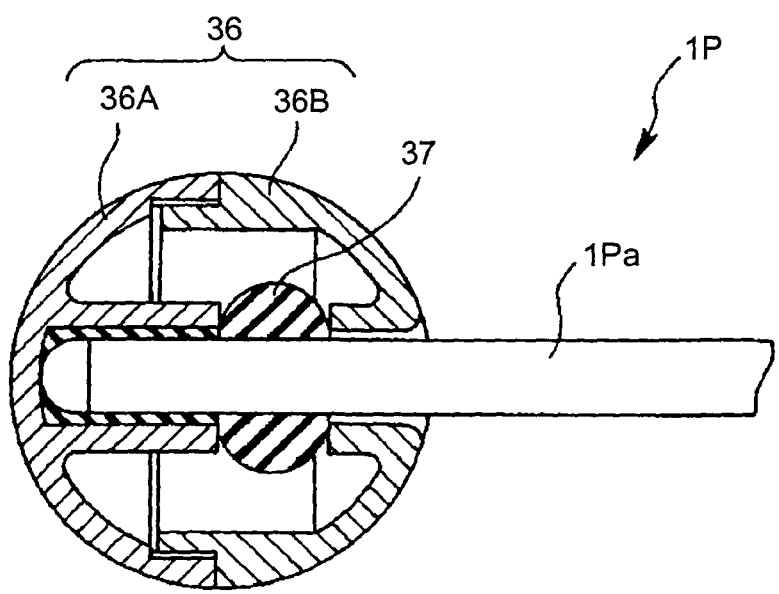
FIG. 68 is a sectional view of the spherical member attached to and securely fixed to the distal end portion of the endoscope insertion assistant probe (inserted shape detecting probe) of FIG. 67.

FIGS. 67 and 68 are enlarged views of a relevant portion, in particular, a distal end portion of the endoscope insertion assistant probe (inserted shape detecting probe) according to the eleventh embodiment of the present invention. Specifically, FIG. 67 is a sectional view showing an exploded state of a spherical member securely fixed to the distal end portion of the inserted shape detecting probe. FIG. 68 is a sectional view showing the spherical member securely fixed to the distal end portion of the inserted shape detecting probe.

A basic structure of the eleventh embodiment is substantially the same as the structure of each of the tenth embodiment and two modifications thereof. The spherical member securely fixed to the distal end portion of the endoscope insertion assistant probe (inserted shape detecting probe) will be described in detail below.

As shown in FIG. 67, an inserted shape detecting probe 1P of the eleventh embodiment has a hollow spherical member 36, which is the distal end guiding element, securely attached to the distal end portion thereof. The spherical member 36 consists of two members, i.e., semi-spherical members 36A and 36B. Two semi-spherical members 36A and 36B respectively have screw portions 36Aa, and 36Ba. Fitting the screw portion 36Ba into the screw portion 36Aa allows the semi-spherical members 36A and 36B to be connected together. The spherical member 36 obtained by the screw coupling of the two semi-spherical members 36A and 36B is as shown in FIG. 68.

A probe main body 1Pa is attached to the spherical member 36 as if the probe main body 1Pa is buried into the spherical member 36. A depression 36Ab is formed on an internal side surface of the semi-spherical member 36A so that the distal end portion of the probe main body 1Pa is fitted therein. Further, a through hole 36Bb is formed in the semi-spherical member 36B so that the distal end portion of the probe main body 1Pa penetrates therethrough. When the two semi-spherical members 36A and 36B are engaged with each other to form the spherical member 36, the depression 36Ab and the through hole 36Bb are arranged on an identical axis.

Further, a anchoring member 37, made of a member such as a heat shrinkable tube, is arranged at a position between the depression 36Ab and the through hole 36Bb. The anchoring member 37 covers around an outer circumferential surface of the probe main body 1Pa, when the probe main body 1Pa penetrates through the through hole 36Bb and fits into the depression 36Ab. When the two semi-spherical members 36A and 36B are engaged with each other to form the spherical member 36, the anchoring member 37 is compressed between the depression 36Ab and the through hole 36Bb. A compression force applied onto the anchoring member 37 works in the axial direction of the probe main body 1Pa so as to prevent the slippage of the probe main body 1Pa in the axial direction.

According to the eleventh embodiment having the above described structure, the spherical member 36 can be securely fixed to the distal end portion of the probe main body 1Pa.

The endoscope insertion assistant probe is inserted inside the body cavity prior to the insertion of the endoscope inside the body cavity. When employed, the endoscope insertion assistant probe is placed inside a forceps channel of the endoscope, for example. After inserting the endoscope insertion assistant probe inside the body cavity of the subject, the operator inserts the endoscope inside the body cavity using the endoscope insertion assistant probe as a guide. Therefore, if the spherical member of the eleventh embodiment always stays within the viewing field of the endoscope, the spherical member might obstruct a display of the observation screen at an examination or an observation of the inside of the body cavity with the endoscope.

Hence, it is convenient if the probe can be structured so that the spherical member and the probe main body can be detached from each other as necessary. A twelfth embodiment of the present invention described below is provided in view of the above.

Figure 69:
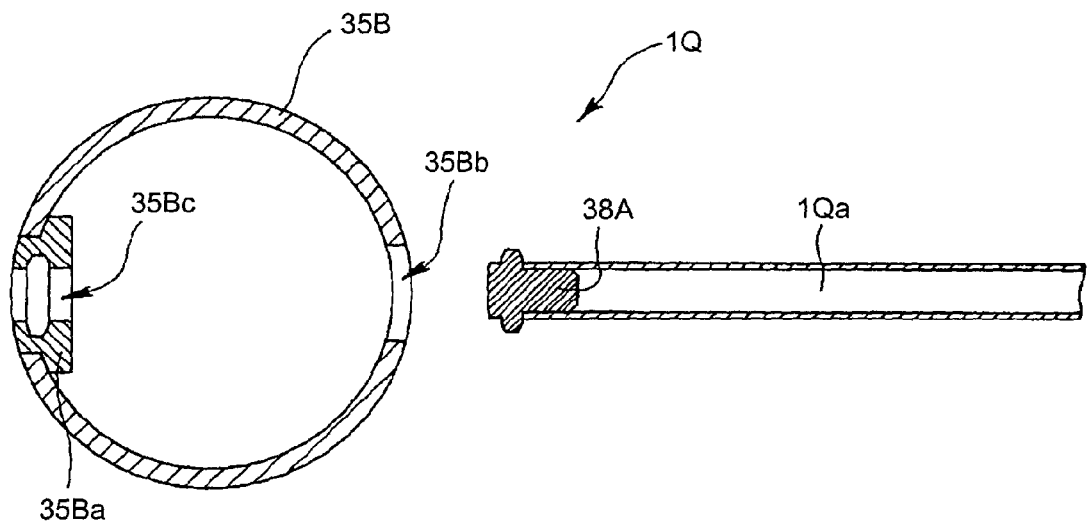
FIG. 69 is a sectional view showing a probe main body and a spherical member securely fixed to a distal end portion of an endoscope insertion assistant probe (inserted shape detecting probe) according to a twelfth embodiment of the present invention in a separated state.
Figure 70:
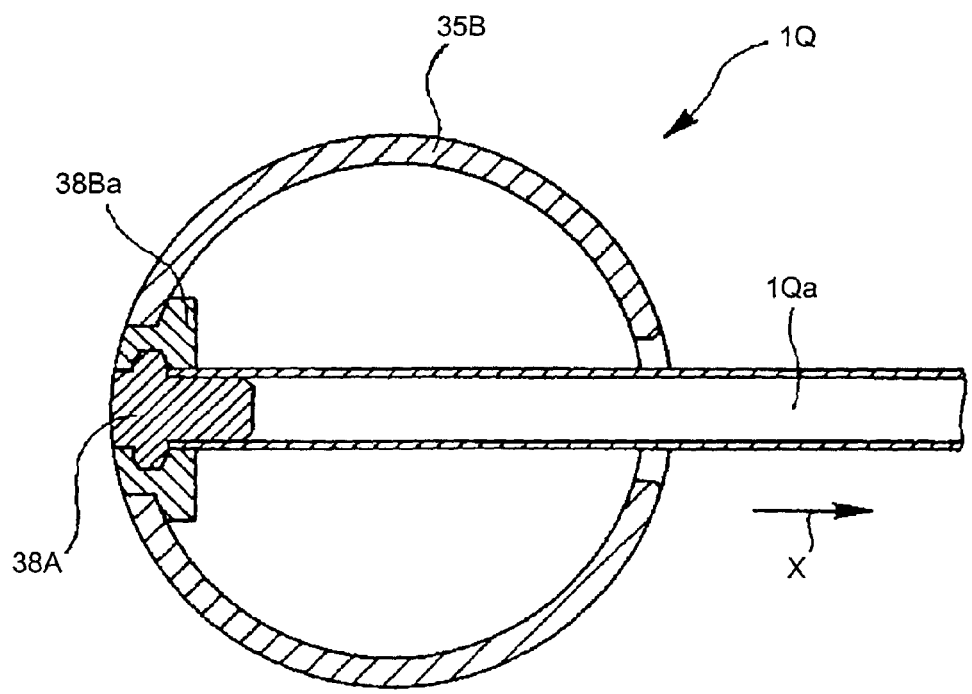
FIG. 70 is a sectional view of the spherical member attached to and securely fixed to the distal end portion of the endoscope insertion assistant probe (inserted shape detecting probe) of FIG. 69.

FIGS. 69 to 70 are enlarged views of a relevant portion, in particular, the distal end portion of the endoscope insertion assistant probe (inserted shape detecting probe) according to the twelfth embodiment of the present invention. Specifically, FIG. 69 is a sectional view showing a detached state of the spherical member which is to be securely fixed to the distal end portion and the probe main body of the inserted shape detecting probe. FIG. 70 is a sectional view showing the spherical member securely fixed to the distal end portion of the inserted shape detecting probe.

A basic structure of the twelfth embodiment is substantially the same as the structure of each of the tenth embodiment and two modifications thereof. The spherical member securely fixed to the distal end portion of the endoscope insertion assistant probe (inserted shape detecting probe) will be described in detail below.

As shown in FIGS. 69 and 70, an inserted shape detecting probe 1Q of the twelfth embodiment includes a probe main body 1Qa and a spherical member 35B which is the distal end guiding element. The probe main body 1Qa has a distal end tip 38A provided at a most distal end portion thereof. The distal end tip 38A is made of an elastic material and has a flange that radially protrudes. On the other hand, the spherical member 35B has a through hole 35Bb formed through an outer wall surface thereof and an elastic member 35Ba securely fixed to an inner wall surface opposite to the through hole 35Bb. The elastic member 35Ba has a fitting hole 35Bc which has substantially the same sectional shape as the distal end tip 38A. When the probe main body 1Qa is inserted through the through hole 35Bb into the spherical member 35B, the distal end tip 38A fits into the fitting hole 35Bc.

Here, a protruding portion of the distal end tip 38A is formed so as to fit into a depression of the fitting hole 35Bc. When engaged, the spherical member 35B and the probe main body 1Qa are integrated. The integrated state is shown in FIG. 70.

When the probe main body 1Qa is pulled in an X direction shown in FIG. 70 relative to the spherical member 35B, the probe main body 1Qa and the spherical member 35B become disengaged and the two members are separated. During this procedure, the spherical member 35B needs to be held by a fixed member. Following is an example.

Assume that the probe main body 1Qa is inserted inside the forceps channel of the endoscope (3; see FIG. 1), and the distal end portion of the probe main body 1Qa slightly protrudes from the distal end of the insertion portion of the endoscope. The spherical member 35B is securely fixed to the distal end portion of the probe main body 1Qa by fitting members as described above.

Assume that the probe is inserted inside the body cavity in the state as described above and that the spherical member 35B is to be removed from the probe main body 1Qa. First, a force is applied to the probe main body 1Qa in a direction to pull out the probe main body 1Qa from the spherical member 35B. Then, the spherical member 35B comes into contact with the most distal end portion of the insertion portion of the endoscope. Thus, the spherical member 35B comes to be fixed with respect to the probe main body 1Qa. If a force is further applied to pull out the probe main body 1Qa, the probe main body 1Qa and the spherical member 35B are disengaged, and become separated, whereby the spherical member 35B falls off. Thus, the spherical member 35B moves out from the distal end portion of the endoscope insertion portion, i.e., from the observation viewing field, and does not obstruct the observation viewing field. The fallen spherical member 35B is naturally discharged from the subject following the peristaltic movement of the body cavity, for example.

In the twelfth embodiment having the above described structure, the probe main body 1Qa and the spherical member 35B in the inserted shape detecting probe 1Q are structured so as to be optionally detachable. Further, the spherical member 35B is formed so that the operator can remove the spherical member 35B from the probe main body 1Qa after inserting the endoscope insertion portion inside the body cavity using the inserted shape detecting probe 1Q as a guide. Therefore, the spherical member 35B does not obstruct the observation viewing field of the endoscope insertion portion, and the subsequent operation of endoscopic observation can securely be performed in a good condition.

In the twelfth embodiment described above, the probe main body 1Qa and the spherical member 35B in the inserted shape detecting probe 1Q are structured to be separable. When the probe main body 1Qa and the spherical member 35B are separated from each other inside the body cavity, the spherical member 35B falls off inside the body cavity and is naturally discharged outside the body cavity.

However, it would be more convenient if the probe main body and the spherical member in the inserted shape detecting probe are structured so as to be separable, though the separation of the probe main body and the spherical member inside the body cavity does not cause falling off of the spherical member, and the spherical member can be immediately recovered. A thirteenth embodiment described below is provided in consideration of the above.

Figure 71:
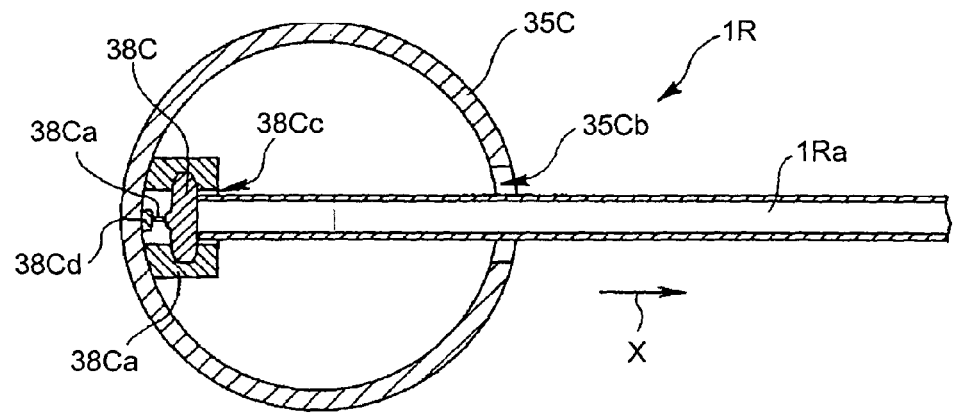
FIG. 71 is a sectional view of a spherical member attached to and securely fixed to a distal end portion of an endoscope insertion assistant probe (inserted shape detecting probe) according to a thirteenth embodiment of the present invention.
Figure 72:
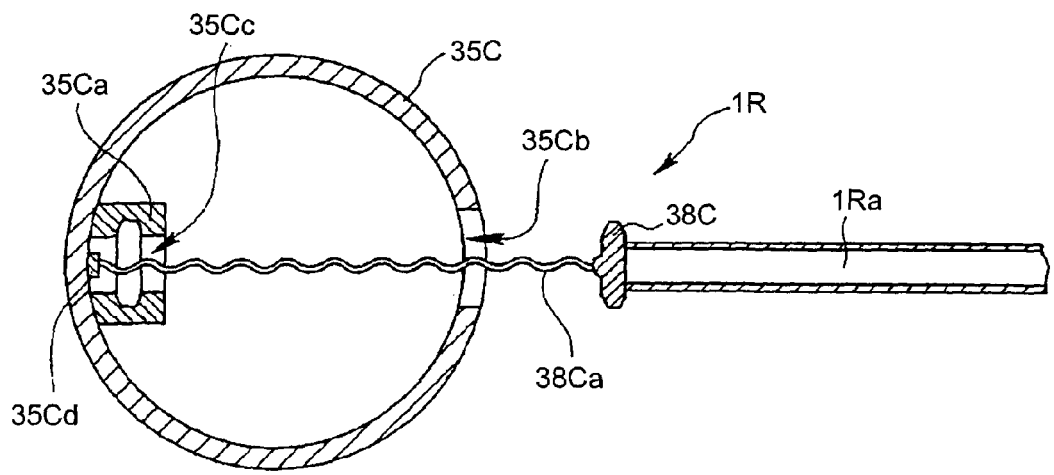
FIG. 72 is a sectional view showing a probe main body and the spherical member securely fixed to the distal end portion of the endoscope insertion assistant probe (inserted shape detecting probe) of FIG. 71 in a separated state.

FIGS. 71 and 72 are enlarged views of a relevant portion, in particular, a distal end portion of an endoscope insertion assistant probe (inserted shape detecting probe) of the thirteenth embodiment of the present invention. Specifically, FIG. 71 is a sectional view showing the spherical member securely fixed to the distal end portion of the inserted shape detecting probe. FIG. 72 is a sectional view showing the spherical member, which is to be securely fixed to the distal end portion of the inserted shape detecting probe, separated from the probe main body.

A basic structure of the thirteenth embodiment is substantially the same as the structure of each of the tenth embodiment and two modifications thereof. The spherical member securely fixed to the distal end portion of the endoscope insertion assistant probe (inserted shape detecting probe) will be described below in detail.

As shown in FIGS. 71 and 72, an inserted shape detecting probe 1R of the thirteenth embodiment includes a probe main body 1Ra and a spherical member 35C which is the distal end guiding element. A distal end tip 38C is securely fixed to the most distal end portion of the probe main body 1Ra. The distal end tip 38C is made of an elastic member and has a flange that protrudes radially. On the other hand, the spherical member 35C has a through hole 35Cb formed in an outer wall surface, and an elastic member 35Ca securely fixed to an inner wall surface opposite to the through hole 35Cb. The elastic member 35Ca has a fitting hole 35Cc which has a substantially the same sectional shape as the distal end tip 38C. When the probe main body 1Ra penetrates through the through hole 35Cb, the distal end tip 38C comes to fit into the fitting hole 35Cc.

Here, the flange of the distal end tip 38C is formed so as to fit to the depression of the fitting hole 35Cc. Hence, when engaged, the spherical member 35C and the probe main body 1Ra are integrated. The integrated state is shown in FIG. 71.

Further, one end portion of a thread member 38Ca is securely fixed to a securing portion 35Cd on an inner wall surface side of the spherical member 35C inside the elastic member 35Ca. Another end portion of the thread member 38Ca is securely fixed to the most distal end portion of the distal end tip 38C. Thus, the spherical member 35C is connected with the probe main body 1Ra by the thread member 38Ca.

When the probe main body 1Ra is pulled in a direction denoted by an arrow X in FIG. 71 relative to the spherical member 35C while the spherical member 35C and the probe main body 1Ra are maintained in the state described above, the probe main body 1Ra and the spherical member 35C are disengaged and separated. However, the probe main body IRa and the spherical member 35 are still connected by the thread member 38Ca as shown in FIG. 72.

Thus, the spherical member 35C becomes disengaged and separated from the distal end portion of the endoscope insertion portion, and does not obstruct the observation viewing field of the endoscope. However, the spherical member 35C disengaged from the probe main body 1Ra is still connected to the probe main body 1Ra by the thread member 38Ca. When the endoscope insertion portion is pulled out from the body cavity during the observation and examination, the spherical member 35C moves together with the insertion portion. Eventually, when the endoscope insertion portion comes outside the body cavity, the spherical member 35C is discharged outside the body cavity together with the insertion portion.

The thirteenth embodiment having the structure as described above has the same advantage as that of the twelfth embodiment. At the same time, since the probe main body 1Ra and the spherical member 35C are connected by the thread member 38Ca, the spherical member 35C can be discharged at the end of the endoscopic observation and examination after the spherical member 35C is separated from the distal end portion of the probe main body 1Ra inside the body cavity.

Figure 73:
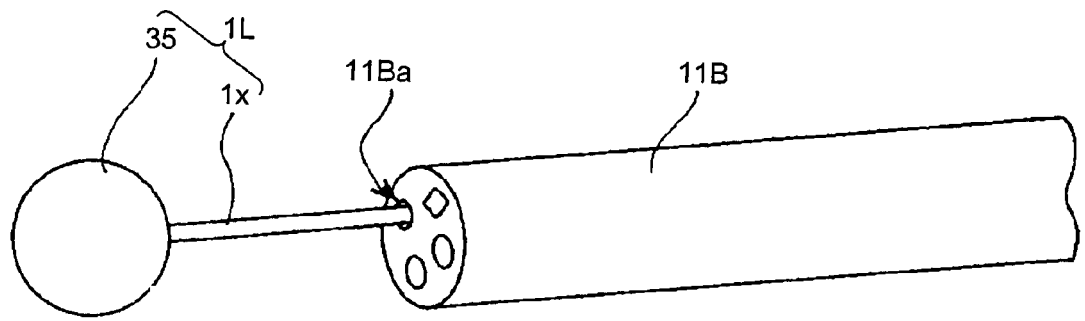
FIG. 73 shows the endoscope insertion assistant probe of FIG. 64 (tenth embodiment) as inserted into a forceps channel of an endoscope for use.
Figure 74:
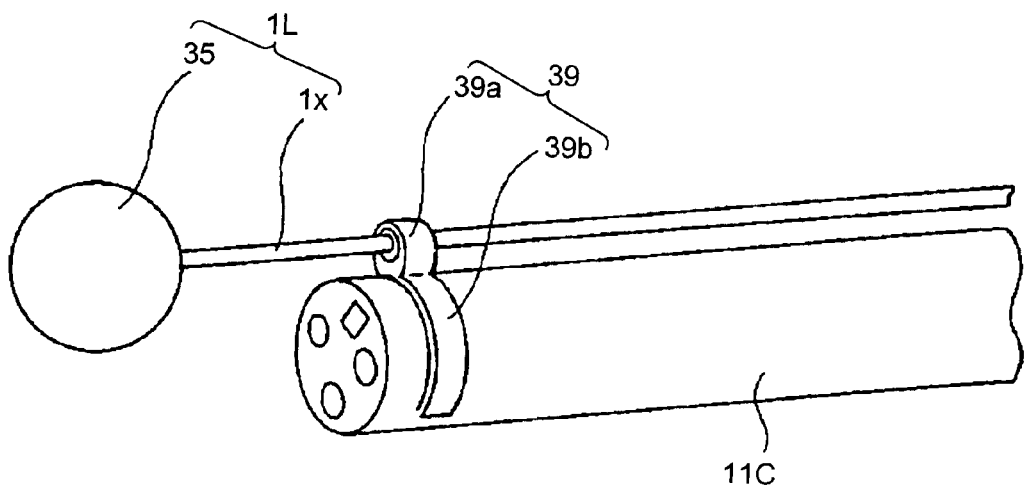
FIG. 74 shows the endoscope insertion assistant probe of FIG. 64 (tenth embodiment) as held outside the insertion portion of the endoscope for use.

The inserted shape detecting probe, i.e., the endoscope insertion assistant probe of each of the tenth to the thirteenth embodiments and the modifications thereof, includes a spherical member at the most distal end portion of the probe main body and can be used in combination with the endoscope insertion portion as shown in FIGS. 73 and 74, for example.

Specifically, FIG. 73 shows how the endoscope insertion assistant probe of the tenth embodiment of FIG. 64 is used while being inserted into the forceps channel of the endoscope.

As shown in FIG. 73, a probe main body 1x of an inserted shape detecting probe 1L, which is the endoscope insertion assistant probe, is inserted inside a forceps channel 11Ba of an endoscope insertion portion 11B, and a portion around a most distal end portion of the probe 1L protrudes from a most distal end portion of the endoscope insertion portion 11B. The spherical member 35 is securely fixed to the most distal end portion of the probe main body 1x.

The endoscope insertion portion 11B in the above described state is inserted from an anus, for example, and the inserted shape detecting probe 1L is pushed inside to advance through the intestinal canal. Eventually, the spherical member 35 provided at the distal end portion of the probe 1L reaches a target region inside the body cavity. Thereafter, the operator moves the endoscope insertion portion 11B through the intestinal canal using the inserted shape detecting probe 1L as a guide up to a position where the spherical member 35 is located. Thus, the preparation is completed for the observation and examination with the endoscope insertion portion 11B.

On the other hand, the inserted shape detecting probe can be employed in a manner as shown in FIG. 74. FIG. 74 shows the endoscope insertion assistant probe of the tenth embodiment shown in FIG. 64 held and used outside the insertion portion of the endoscope.

As shown in FIG. 74, a probe holder 39 is provided around an outer circumferential surface of the endoscope insertion portion 11C near the distal end portion thereof so as to grab and hold the outer circumference of the endoscope insertion portion 11C. The probe holder 39 includes a holder 39a having a through hole through which the probe main body 1x is placed, and an arm 39b holding the endoscope insertion portion 11C from around the outer circumferential surface thereof. The inserted shape detecting probe 1L, which is the endoscope insertion assistant probe, is held in parallel with an axial direction of the endoscope insertion portion 11C by the probe holder 39.

Here, the spherical member 35 provided at the most distal end portion of the probe main body 1x of the inserted shape detecting probe 1L is arranged in front of the distal end portion of the endoscope insertion portion 11C.

The endoscope insertion portion 11C in the above described state is inserted from the anus, for example, and the inserted shape detecting probe 1L is pushed to advance inside the intestinal canal. Eventually, the spherical member 35 at the distal end portion thereof reaches a target region inside the body cavity. Thereafter, the operator moves the endoscope insertion portion 11C inside the intestinal canal using the inserted shape detecting probe 1L as a guide up to a position where the spherical member 35 is located. Thus, the preparation is completed for the observation and examination with the endoscope insertion portion 11C.

In the above described embodiments, various types of the distal end guiding element which is provided at the distal end of the inserted shape detecting probe are illustrated. A specific distal end guiding element is selected and fixed to each of the probe. When the inserted shape detecting probes with different types of distal end guiding elements are needed to be employed according to the manner of examination, plural types of inserted shape detecting probes need to be prepared corresponding to respective types of the distal end guiding elements.

Therefore, it would be convenient if plural types of distal end guiding elements can be attached to one inserted shape detecting probe, and an appropriate distal end guiding element can be selected at each time of the use.

In a fourteenth embodiment of the present invention described below, plural types of distal end guiding elements are prepared and selectively and detachably attached to one inserted shape detecting probe depending on a preference of the operator, difference in the shape of large intestine (depending on the age of the subject, for example), a manner of examination, and the like.

Figure 75:
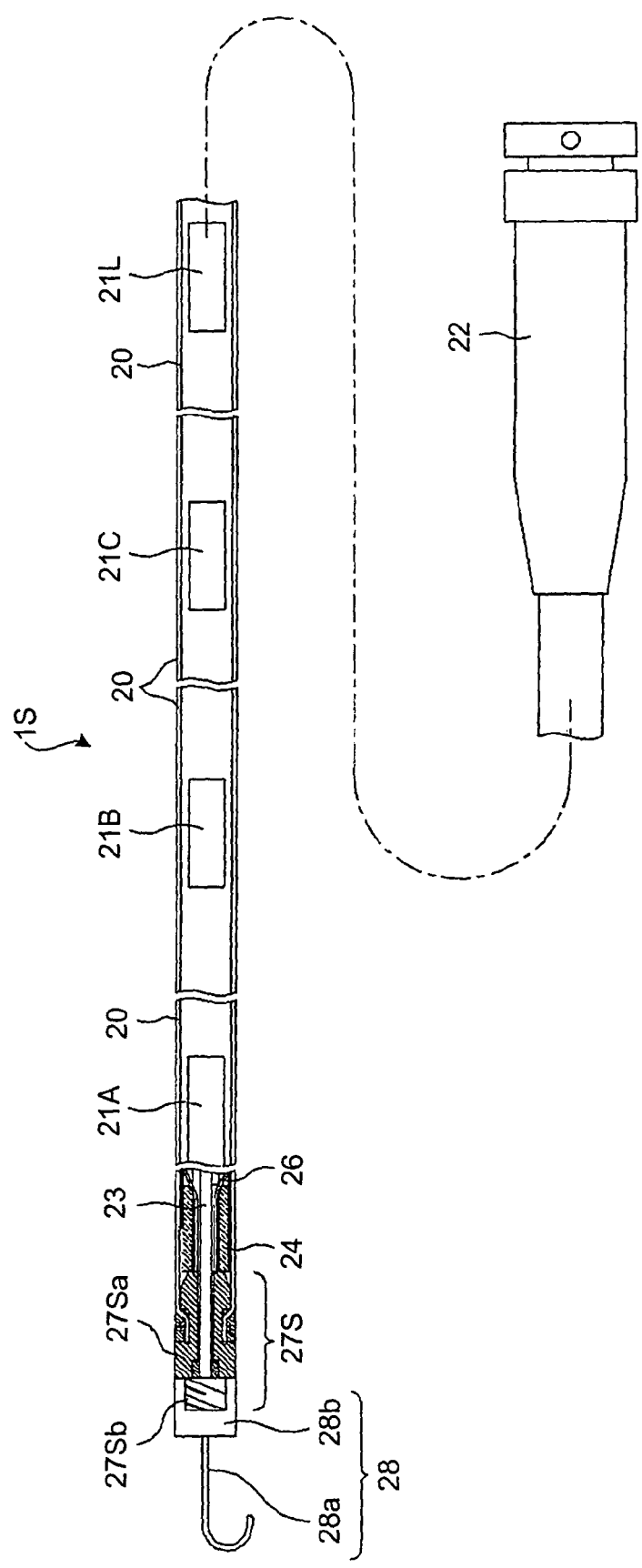
FIG. 75 is a sectional view of an internal structure of a portion near a distal end portion of an inserted shape detecting probe (endoscope insertion assistant probe) in an inserted shape detecting apparatus system of a fourteenth embodiment of the present invention.
Figure 76:
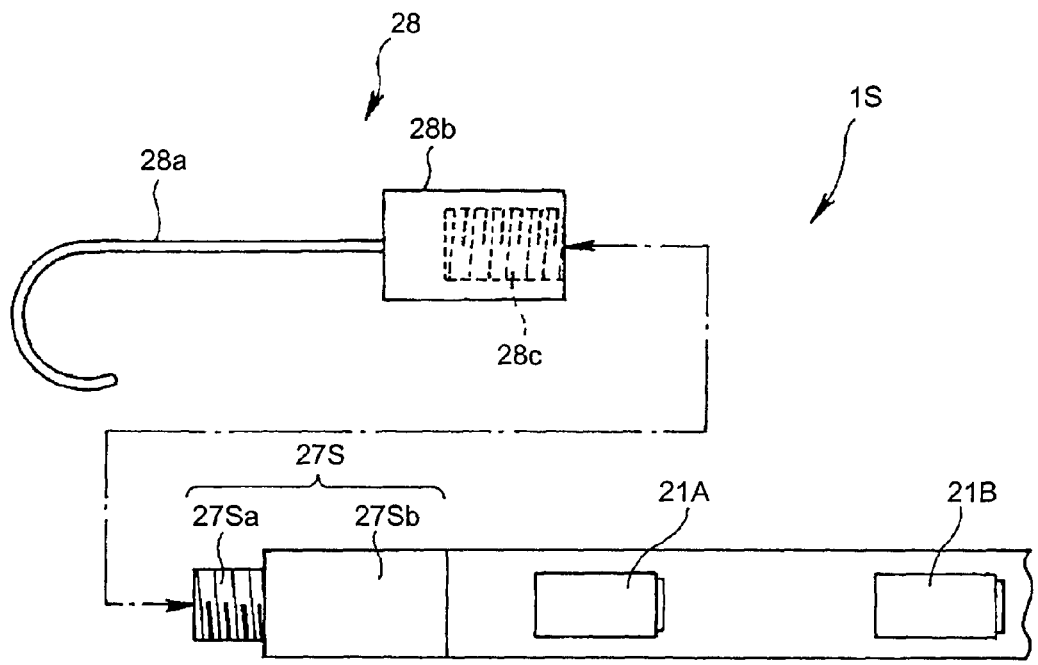
FIG. 76 is an enlarged view of a relevant portion, in particular, a distal end guiding element and an attachment position thereof in a portion near the distal end portion of the inserted shape detecting probe (endoscope insertion assistant probe) of FIG. 75.

FIGS. 75 and 76 show a schematic structure of the inserted shape detecting probe (endoscope insertion assistant probe) in an inserted shape detecting apparatus system of the fourteenth embodiment of the present invention. Specifically, FIG. 75 is a sectional view of an internal structure near a distal end portion of an inserted shape detecting probe (endoscope insertion assistant probe) applied to the fourteenth embodiment. FIG. 76 is an enlarged view of a relevant portion, in particular, a distal end guiding element and an attachment position of the distal end guiding element near the distal end portion of the inserted shape detecting probe (endoscope insertion assistant probe) of FIG. 75.

The inserted shape detecting apparatus system of the fourteenth embodiment is different from the inserted shape detecting apparatus system of the first embodiment shown in FIG. 1 only in the structure near the distal end portion of the inserted shape detecting probe, which is the endoscope insertion assistant probe. Therefore, the elements common between the fourteenth embodiment and the first embodiment will be denoted by the same reference characters, and detailed description thereof will not be repeated. Different elements alone will be described below.

An inserted shape detecting probe 1S of the fourteenth embodiment includes a distal end guiding element 28 provided at a distal end side of a distal end piece 27S which is provided at the distal end portion of the inserted shape detecting probe 1S as shown in FIGS. 75 and 76. The distal end guiding element 28 primarily includes a guiding element base 28b which is coupled to a most distal end portion of the distal end piece 27S of the inserted shape detecting probe 1S and integrated with the distal end piece 27S, and a guide wire 28a protruding forward from a front surface of the guiding element base 28b.

As shown in FIG. 76, a screw portion 28c (female screw, for example) is provided in a substantially central portion of a proximal end of the guiding element base 28b. The screw portion 28c has a depression of a predetermined depth dimension bored towards a distal end side along the axial direction of the inserted shape detecting probe 1S.

On the other hand, a screw portion 27Sa (male screw, for example) corresponding to the screw portion 28c is provided at the most distal end portion of the distal end piece 27S of the inserted shape detecting probe 1S and protrudes outward in the axial direction.

Through a screw coupling of the screw portion 27Sa of the distal end piece 27S and the screw portion 28c of the guiding element base 28b, the distal end piece 27S and the distal end guiding element 28 take an integrated shape. Thus, the inserted shape detecting probe 1S of the fourteenth embodiment is formed. Further, when the screw portion 27Sa of the distal end piece 27S and the screw portion 28c of the guiding element base 28b are disengaged, the distal end guiding element 28 can be easily removed from the distal end piece 27S. In brief, the distal end guiding element 28 is detachably provided with respect to the distal end piece 27S of the inserted shape detecting probe 1S.

Further, the guide wire 28a is set in the distal end of the guiding element base 28b. The guide wire 28a is a core, for example. The guide wire 28a is formed so that a distal end side thereof facilitates a smooth movement of the guide wire 28a in a forward direction. For example, the guide wire 28a has a curved distal end portion protruding toward the forward direction. The guide wire 28a is formed in such shape that the inserted shape detecting probe 1S, to which the distal end guiding element 28 is attached at the distal end portion, can advance smoothly along the intestine wall when inserted inside the intestinal canal, for example. A length of the guide wire 28a is appropriately set in consideration of the use and the like. The structure of the fourteenth embodiment is the same as that of the first embodiment if not specified otherwise above.

In the fourteenth embodiment, the distal end guiding element 28 is detachably attached to the distal end of the distal end piece 27S in the inserted shape detecting probe 1S.

Possible modifications of the distal end guiding element 28 described above are shown in FIGS. 77 and 78, for example.

Figure 77:
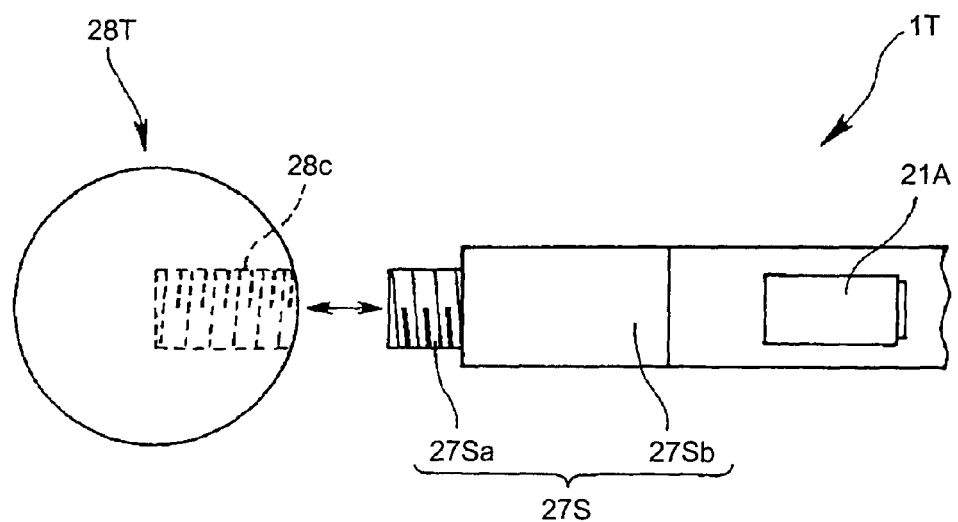
FIG. 77 is an enlarged view of a relevant portion, in particular, one mode of the distal end guiding element and the attachment position thereof as applied to the inserted shape detecting probe (endoscope insertion assistant probe) in the inserted shape detecting apparatus system of FIG. 75.
Figure 78:
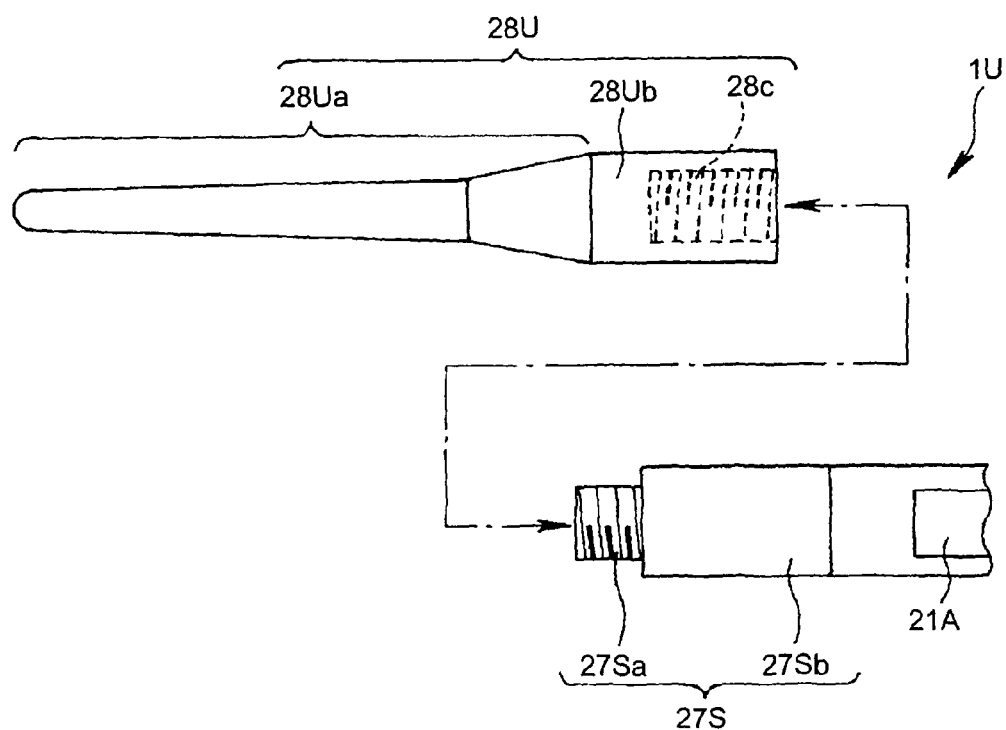
FIG. 78 is an enlarged view of a relevant portion, in particular, another mode of the distal end guiding element and the attachment position thereof as applied to the inserted shape detecting probe (endoscope insertion assistant probe) in the inserted shape detecting apparatus system of FIG. 75.

FIGS. 77 and 78 are enlarged views of respective two modifications of the distal end guiding element and the attachment position of the distal end guiding element, that can be applied to the inserted shape detecting probe (endoscope insertion assistant probe) in the inserted shape detecting apparatus system of the fourteenth embodiment.

A distal end guiding element 28T of a modification shown in FIG. 77 consists of a spherical member whose appearance is substantially the same as the appearance of that in the first embodiment (see FIG. 64), the twelfth embodiment (see FIGS. 69 and 70), and the thirteenth embodiment (see FIGS. 71 and 72), i.e., a spherical member having a perfect circle section, an oval section, or the like.

The distal end guiding element 28T has a highly slidable surface and light in weight. The distal end guiding element 28T is made of a material such as Teflon®, Duracon®, polysulfone, and polyphenylsulfone. A diameter of the distal end guiding element 28T is set larger than the diameter of the probe main body, for example, approximately 10 to 30 mm (φ=10 to 30 mm), or more desirably approximately 10 to 20 mm (φ=10 to 20 mm).

Approximately at the center of the proximal end of the distal end guiding element 28T, the screw portion 28c (female screw, for example) is formed. The screw portion 28c has a depression bored toward the distal end side along the axial direction of the inserted shape detecting probe 1S.

On the other hand, another distal end guiding element 28U shown in FIG. 78, is an elongated axial member having a curved distal end portion. The distal end guiding element 28U includes a guiding element base 28Ub, and an elastic member 28Ua which is integrally coupled to the guiding element base 28Ub and has a smaller diameter than the guiding element base 28Ub and a predetermined length. The elastic member 28Ua of the distal end guiding element 28U is made of the same material as the material of the distal end guiding element 28T described above.

Approximately at the center of the proximal end of the guiding element base 28Ub of the distal end guiding element 28U, a screw portion 28c (female screw, for example) is formed. The screw portion 28c has a depression bored toward the distal end side along the axial direction of the inserted shape detecting probe 1S.

An operation for using the inserted shape detecting probe 1S as the endoscope insertion assistant probe of the fourteenth embodiment is substantially the same as that in the first embodiment.

In addition, in the fourteenth embodiment, one distal end guiding element that has an appropriate shape is selected from the plural types of distal end guiding elements (28, 28T, 28U) as necessary prior to the examination, and is attached to the distal end of the inserted shape detecting probe 1S for use.

As described above, the fourteenth embodiment has substantially the same advantage as that of the first embodiment. In addition, since the distal end guiding element (28, 28T, 28U) is detachably formed with respect to the distal end piece 27S of the inserted shape detecting probe 1S, one distal end guiding element can be selected at will as necessary from the plural types of distal end guiding elements (28, 28T, 28U) and can be attached to the probe 1S for use. Therefore, simply with the preparation of the plural types of distal end guiding elements, the inserted shape detecting probe 1S can be readily implemented as the inserted shape detecting probes with various shapes of distal end portions.

Thus, the distal end guiding element can be selected according to the use, and workload of the manual operation on the operator at the insertion can be alleviated.

In the fourteenth embodiment, the screw portion 28c at the side of the distal end guiding element (28, 28T, 28U) is formed as a female screw, whereas the screw portion 27Sa of the distal end piece 27S of the inserted shape detecting probe 1S is formed as a male screw. Such configuration, however, is not limiting. For example, the screw portion 28c may be a male screw, and the screw portion 27Sa may be a female screw.

In the fourteenth embodiment, the coupling and decoupling between the distal end guiding element (28, 28T, 28U) and the distal end piece 27S of the inserted shape detecting probe 1S are performed by a fastening unit consisting of screws. Such configuration, however, is not limiting. For example, a fitting unit implemented in a manner as shown in the twelfth embodiment (see FIGS. 69 and 70) and the thirteenth embodiment (see FIGS. 71 and 72) can be employed, i.e., one portion may be formed as a protruding part and another portion may be formed as a depressed part, and the two portions may be coupled by fitting (by so-called snapping).

In the twelfth and the thirteenth embodiments, two parts of the fastening unit are elastic members, for example, so as to allow relatively easy decoupling and separating of the parts (i.e., the distal end guiding element and the distal end portion of the probe). Contrarily, in the fourteenth embodiment, the coupling between the two parts (i.e., the distal end guiding element and the distal end portion of the probe) needs to be relatively strong. Therefore, it is desirable to use a material such as a resin member that has a high hardness though elastic.

When the configurations as described above are employed, different units can be easily used to readily engage and disengage the distal end guiding element (28, 28T, 28U) with and from the distal end piece 27S of the inserted shape detecting probe 1S.

The type of the distal end guiding element applied in the fourteenth embodiment is not limited to those shown in FIGS. 76 to 78. Various types of distal end guiding elements can be applied as necessary. For example, the other types of the distal end guiding elements may be a balloon member, a cone member with a rounded apex, or a semi-spherical member whose rounded surface facing the forward direction.

The distal end guiding element of the fourteenth embodiment is readily applicable to the second modification of the tenth embodiment (see FIG. 74) described above.

Another example of the distal end guiding element provided at the distal end of the inserted shape detecting probe (endoscope insertion assistant probe) will be described below.

Figure 79:
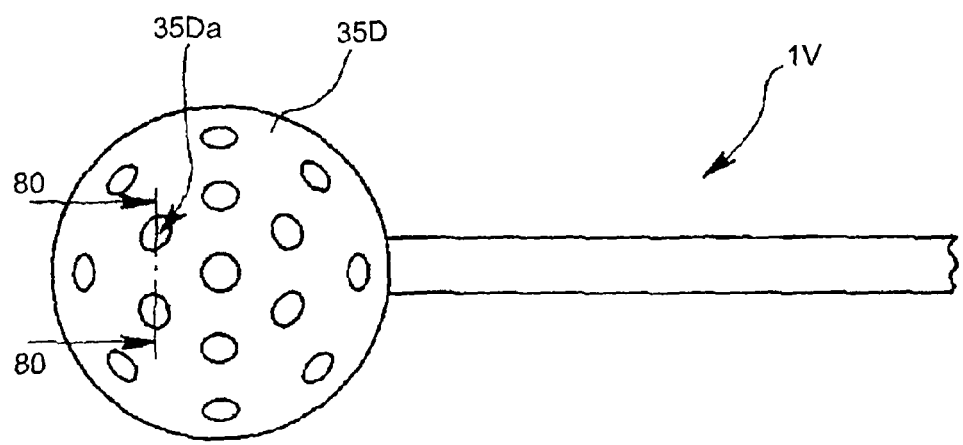
FIG. 79 is a side view of a structure of a portion near a distal end portion of an inserted shape detecting probe (endoscope insertion assistant probe) according to a fifteenth embodiment of the present invention.
Figure 80:
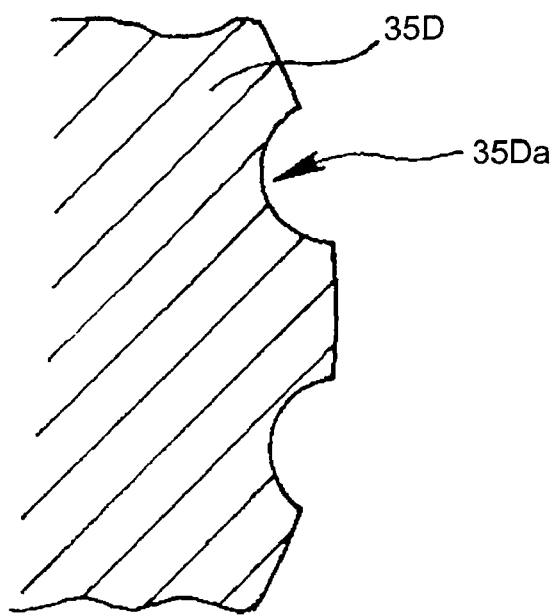
FIG. 80 is an enlarged sectional view of a relevant portion, in particular, a dimple formed on a surface of a distal end guiding element provided near the distal end portion of the inserted shape detecting probe (endoscope insertion assistant probe) of FIG. 79 along line 80-80 of FIG. 79.

FIGS. 79 and 80 show a fifteenth embodiment of the present invention. Specifically, FIG. 79 is a side view showing a structure of an inserted shape detecting probe (endoscope insertion assistant probe) according to the fifteenth embodiment around a distal end portion thereof. FIG. 80 is an enlarged sectional view along line 80-80 of FIG. 79 and shows dimples formed on a surface of a distal end guiding element near the distal end portion of the inserted shape detecting probe (endoscope insertion assistant probe) of FIG. 79.

An inserted shape detecting probe 1V of the fifteenth embodiment includes a distal end guiding element provided at the distal end portion thereof. The distal end guiding element has substantially the same shape as that of each of the tenth embodiment and the modifications thereof, i.e., the spherical member 35D formed as a solid or a hollow sphere. The spherical member 35D has plural dimples 35Da on the surface thereof. The dimple 35Da is formed as a concave surface on the surface of the spherical member 35D as shown in FIG. 80. In other respects, the main structure of the fifteenth embodiment is substantially the same as that of the tenth embodiment.

In the fifteenth embodiment, the plural dimples 35Da formed on the surface of the spherical member 35D, which is the distal end guiding element, contribute to reduce a contact area of the spherical member 35D with the intestinal canal, for example. Therefore, friction resistance generated between the surface of the spherical member 35D and the intestinal canal that contacts therewith can be reduced. In particular, an effect of reduced friction resistance is prominent when the spherical member 35D moves in contact with a smooth wall surface such as the intestine wall. Thus, a force required for the insertion can be reduced particularly when the probe is moved in a portion with a smooth wall surface, whereby the insertability can be improved.

Figure 81:
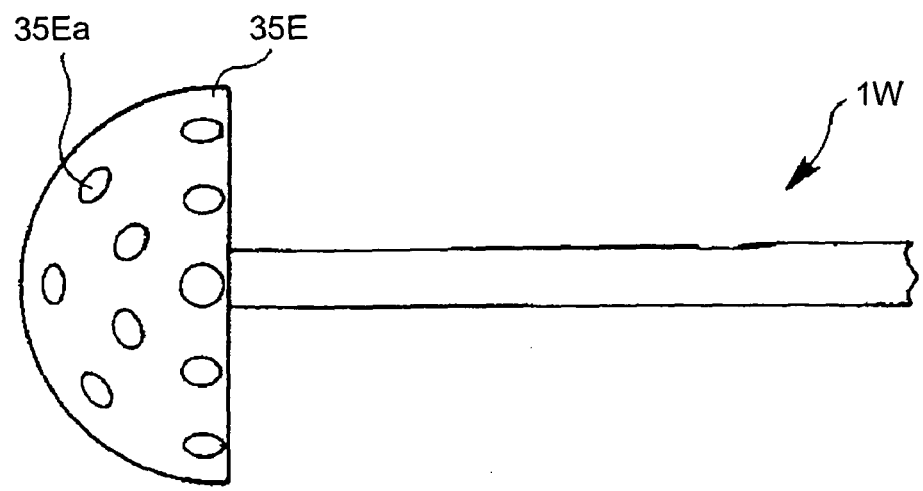
FIG. 81 is a side view of a structure of a portion near a distal end portion of an inserted shape detecting probe (endoscope insertion assistant probe) according to a modification of the fifteenth embodiment of the present invention.

FIG. 81 shows a modification of the fifteenth embodiment described above, and is a side view of a structure near a distal end portion of an inserted shape detecting probe (endoscope insertion assistant probe) according to the modification of the fifteenth embodiment.

As shown in FIG. 81, a distal end guiding element provided in an inserted shape detecting probe 1W of the modification is a semi-spherical member 35E. If the distal end guiding element (spherical member 35D) of the fifteenth embodiment is divided in two along a line passing substantially through a central point thereof, each of two members obtained as a result has the same shape as the semi-spherical member 35E. The semi-spherical member 35E has plural dimples 35Ea on a surface thereof similarly to the spherical member 35D. A sectional shape of the dimple 35Ea is the same as the sectional shape of the dimple 35Da of the spherical member 35D of the fifteenth embodiment (see FIG. 80).

The semi-spherical member 35E is arranged at the distal end portion of the inserted shape detecting probe 1W so that the round surface faces forward. In other respects, the structure of the modification is substantially the same as the structure of each of the tenth and the fifteenth embodiments.

The modification having the above described structure has the same advantage as that of the fifteenth embodiment.

In the fifteenth embodiment and the modification thereof, the dimple (35Da, 35Ea) formed on the surface of the spherical member (35D, 35E) has a concave surface bored on the surface of the spherical member. The shape of the dimple, however, is not limited thereto. For example, the surface of the spherical member itself may be formed from curved surfaces with different curvatures. Alternatively, plural grooves may be formed along a travel direction of the distal end guiding element on the surface of the spherical member itself. Various types of dimple can be employed.

Further, the distal end guiding element (35D, 35E) of the shape as shown in the fifteenth embodiment can be applied as the distal end guiding element of the fourteenth embodiment.

Figure 82:
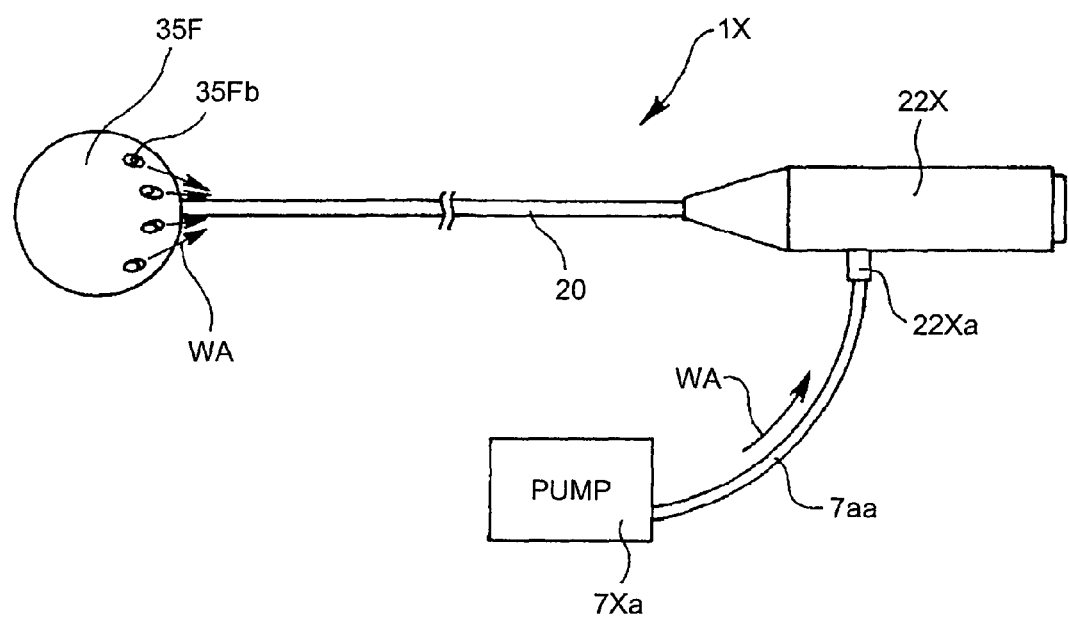
FIG. 82 shows a schematic structure of an endoscope apparatus (inserted shape detecting apparatus system) to which an inserted shape detecting probe (endoscope insertion assistant probe) according to a sixteenth embodiment of the present invention is applied.
Figure 83:
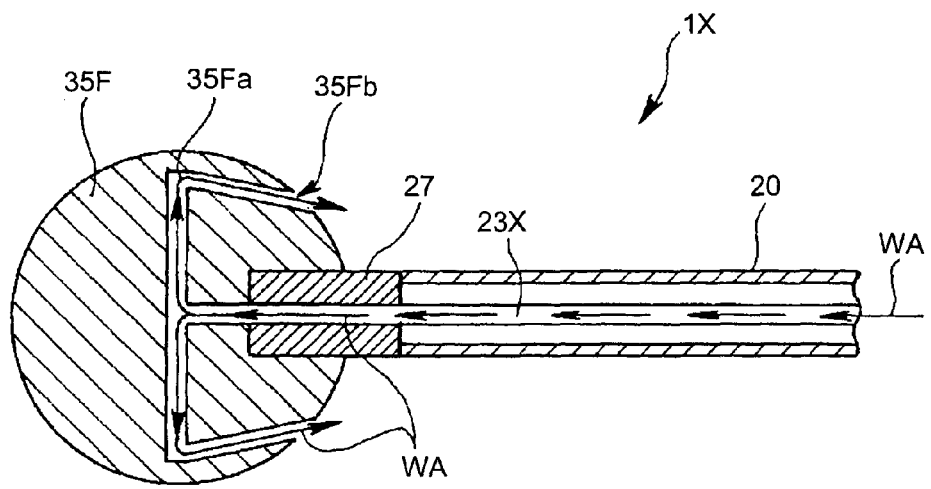
FIG. 83 is a schematic sectional side view of an internal structure of a portion near the distal end portion of the inserted shape detecting probe (endoscope insertion assistant probe) of FIG. 82.

FIGS. 82 and 83 show a sixteenth embodiment of the present invention. Specifically, FIG. 82 shows a schematic structure of an endoscope apparatus (inserted shape detecting apparatus system) to which an inserted shape detecting probe (endoscope insertion assistant probe) of the sixteenth embodiment is applied. Further, FIG. 83 is a schematic sectional side view of an internal structure near a distal end portion of the inserted shape detecting probe (endoscope insertion assistant probe) of FIG. 82.

A basic concept and a structure of the sixteenth embodiment are substantially the same as those of the endoscope insertion assistant probe (inserted shape detecting probe) of the fifth embodiment (see FIG. 49). Difference lies in that a spherical member 35F, which is the distal end guiding element, as shown in FIG. 82 is arranged at a distal end of an inserted shape detecting probe 1X in place of the cover member 31E (see FIG. 49) of the fifth embodiment, to generate propulsion for the spherical member 35F and the inserted shape detecting probe 1X.

The spherical member 35F, which is the distal end guiding element of the sixteenth embodiment, is formed as a solid or a hollow sphere similarly to the tenth and the fifteenth embodiments described above. The spherical member 35F has a through hole 35Fb which serves as a fluid ejecting opening near one side that is connected to the distal end portion of the inserted shape detecting probe 1X. The spherical member 35F has at least one, or plural through holes 35Fb. The through hole 35Fb communicates with a guiding element side fluid pipe 35Fa formed inside the spherical member 35F as shown in FIG. 83.

On the other hand, a probe side fluid pipe 23X communicates with the inserted shape detecting probe 1X. The probe side fluid pipe 23X has an opening (not specifically shown) on a front surface of the distal end portion. Specifically, the probe side fluid pipe 23X is formed inside a hollow member which is employed as the core 23 of the first embodiment, for example. Alternatively, a different tube member may be inserted inside the outer sheath 20 of the inserted shape detecting probe 1X to form the probe side fluid pipe 23X.

The probe side fluid pipe 23X penetrates inside the inserted shape detecting probe 1X from the opening at the front surface of the distal end portion to a water tube connecting portion 22Xa at a connector portion 22X provided near a proximal end portion. The water tube connecting portion 22Xa is further connected to one end of a water tube 7aa. Another end of the water tube 7aa is connected to an outlet of a water pump 7Xa which is a fluid supply unit. Thus, a continuous piping is formed from the water pump 7Xa, the water tube 7aa, the connector portion 22X of the inserted shape detecting probe 1x, the probe side fluid pipe 23X, and to the opening on the front surface of the distal end portion of the inserted shape detecting probe 1X.

When the spherical member 35F and the distal end portion of the inserted shape detecting probe 1X are coupled with each other, a guiding element fluid pipe 35Fa of the spherical member 35F is arranged in a position corresponding to the opening in the front surface of the distal end portion of the inserted shape detecting probe 1X. Thus, the spherical member 35F and the distal end portion of the inserted shape detecting probe 1X become coupled, thereby connecting the above described piping on the side of the inserted shape detecting probe 1X with the guiding element side fluid pipe 35Fa of the spherical member 35F. Then, the fluid supplied from the water pump 7Xa by pressure flows through the above described piping and the guiding element side fluid pipe 35Fa, and is eventually discharged from the through hole 35Fb.

Here, the opening of the through hole 35Fb is directed toward the proximal end side of the inserted shape detecting probe 1X which is attached to the spherical member 35 at the distal end portion. The opening of the through hole 35Fb is oriented toward the outer sheath 20 of the probe 1X. Hence, the fluid discharged backward from the opening of the through hole 35Fb is discharged toward the outer sheath 20 of the inserted shape detecting probe 1X.

The water pump 7Xa supplies a predetermined fluid (water or lubricant, for example) at a predetermined timing in a direction of an arrow WA of FIG. 82 under the drive control by a predetermined inserted shape detecting apparatus (not shown). The fluid is supplied via the above described piping through the inserted shape detecting probe 1X to the spherical member 35F, and is discharged from each of the through holes 35Fb in a predetermined direction. The propulsion generated by the force of discharged fluid is controlled through the adjustment of the amount of discharged fluid under the drive control of the delivery pump 7Xa similarly to the pump 7a of the fifth embodiment (see FIG. 49).

It is more preferable if a hydrophilic lubricant coating is applied to the outer surface of the outer sheath 20, for example. In other respects, the structure of the sixteenth embodiment is substantially the same as the structure of each of the fifth and the tenth embodiments.

According to the sixteenth embodiment having the above described structure, the amount of discharged fluid is adjusted and controlled through the drive control of the water pump 7Xa similarly to the fifth embodiment (see FIG. 49), whereby the amount of advancement of the inserted shape detecting probe 1X or the like can be surely adjusted. Further, since the spherical member 35F is employed as the distal end guiding element, the same advantage as that of the tenth or the fifteenth embodiment can be obtained.

When the hydrophilic lubricant coating is applied on the outer surface of the outer sheath 20 of the inserted shape detecting probe 1X, the fluid discharged backward from the opening of each of the through holes 35Fb of the spherical member 35F makes the outer surface of the outer sheath 20 wet in a portion near the distal end portion, thereby preventing the outer surface from drying. Thus, the fluid contributes to suppress drying of the hydrophilic lubricant coating, thereby suppressing the deterioration of self lubricating characteristic thereof. The outer surface of the outer sheath 20 is thus always maintained in a hydrophilic lubricating state, whereby the insertability is further improved.

In the sixteenth embodiment, similarly to the fifteenth embodiment, the distal end guiding element (spherical member 35F) may have a dimple on the surface thereof.

In the sixteenth embodiment, the water pump 7Xa is employed as the fluid supply unit. Alternatively, a manually operated fluid supply unit can be employed, for example, a syringe.

In the above described embodiments, the inserted shape detecting apparatus system in which the inserted shape detecting probe is applied is described as an example of the endoscope apparatus in which the endoscope insertion assistant probe of the present invention is applied. The inserted shape detecting apparatus system is not a limiting example, and the present invention can be readily applied in a similar manner to a general probe other than the inserted shape detecting probe. Even when the present invention is applied to the general probes, the advantage of the present invention, i.e., the improvement in insertability of both the endoscope insertion assistant probe and the insertion portion of the endoscope can be similarly obtained.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope insertion assistant probe comprising: a flexible, elongated probe that detects an inserted shape of the probe at least when the probe is protruded from a distal end of an insertion portion of an endoscope in an insertion direction, the probe including; plural shape detecting elements for generating or detecting a magnetic field, plural signal lines that are connected to the plural shape detecting elements, an elongated core to which the plural detecting elements are securely fixed at predetermined intervals, and an outer sheath that houses the shape detecting elements, the signal lines and the core; and a distal end guiding element that is arranged at a distal end portion of the probe, the distal end guiding element being made of a thin-film resin member having an outer surface coated with a hydrophilic lubricant and expandable by fluid, the distal end guiding element having a diameter larger than that of the probe and smaller than a minimum diameter of a body cavity when the distal end guiding element is fully expanded; wherein the endoscope insertion assistant probe is inserted into the body cavity prior to insertion of the insertion portion of the endoscope into the body cavity to assist the insertion of the endoscope; and the endoscope is inserted over the flexible, elongated probe.

* * * * *